US012774488B2

(12) United States Patent
Lo et al.

(10) Patent No.: US 12,774,488 B2
(45) Date of Patent: Oct. 27, 2026

(54) EFFICIENT DIGITAL MEASUREMENT OF LONG NUCLEIC ACID FRAGMENTS

(71) Applicant: Centre for Novostics, Shatin (HK)

(72) Inventors: Yuk-Ming Dennis Lo, Homantin (CN); Kwan Chee Chan, Jordan (CN); Peiyong Jiang, Pak Shek Kok (CN); Wanxia Gai, Shenzhen (CN); Cheuk Yin Yu, Ma On Shan (CN)

(73) Assignee: Centre for Novostics, Shatin (HK)

( * ) Notice: Subject to any disclaimer, the term of this patent is extended or adjusted under 35 U.S.C. 154(b) by 0 days.

(21) Appl. No.: 18/658,886

(22) Filed: May 8, 2024

(65) Prior Publication Data

US 2024/0384334 A1 Nov. 21, 2024

Related U.S. Application Data

(60) Provisional application No. 63/465,161, filed on May 9, 2023.

(51) Int. Cl.
*C12Q 1/68* (2018.01)
*C12Q 1/6851* (2018.01)

(52) U.S. Cl.
CPC .................................. *C12Q 1/6851* (2013.01)

(58) Field of Classification Search
None
See application file for complete search history.

(56) References Cited

U.S. PATENT DOCUMENTS

| | | | | |
|---|---|---|---|---|
| 6,331,417 | B1 * | 12/2001 | Emery | A61P 31/22 435/6.12 |
| 10,865,454 | B2 * | 12/2020 | Leying | C12Q 1/706 |
| 2009/0029377 | A1 * | 1/2009 | Lo | C12Q 1/6888 702/20 |
| 2009/0053719 | A1 * | 2/2009 | Lo | C12Q 1/6851 435/6.11 |
| 2011/0318734 | A1 * | 12/2011 | Lo | C12Q 1/6886 435/6.11 |
| 2018/0105864 | A1 * | 4/2018 | Murtaza | C12Q 1/6876 |
| 2019/0010562 | A1 * | 1/2019 | Leying | C12Q 1/6823 |
| 2020/0407794 | A1 * | 12/2020 | Macdonald | C12Q 1/6806 |
| 2021/0166781 | A1 * | 6/2021 | Eberle | G16B 30/10 |

FOREIGN PATENT DOCUMENTS

| | | | | | |
|---|---|---|---|---|---|
| CN | 107868816 | A | | 4/2018 | |
| CN | 109355380 | A | | 2/2019 | |
| CN | 112654713 | A | | 4/2021 | |
| WO | 2009019455 | A2 | | 2/2009 | |
| WO | 2010112316 | A1 | | 10/2010 | |
| WO | 2011054936 | A1 | | 5/2011 | |
| WO | 2012028746 | A1 | | 3/2012 | |
| WO | 2013132305 | A1 | | 9/2013 | |
| WO | 2016116033 | A1 | | 7/2016 | |
| WO | 2018081130 | A1 | | 5/2018 | |
| WO | 2018137685 | A1 | | 8/2018 | |
| WO | WO-2019169043 | A1 | * | 9/2019 | C12Q 1/6806 |
| WO | 2023056884 | A1 | | 4/2023 | |
| WO | WO-2024027961 | A1 | * | 2/2024 | C12Q 1/701 |
| WO | WO-2024230768 | A1 | * | 11/2024 | C12Q 1/6806 |

OTHER PUBLICATIONS

Lun et al., 2008. Noninvasive prenatal diagnosis of monogenic diseases by digital size selection and relative mutation dosage on DNA in maternal plasma. P.N.A.S., 105(50), pp. 19920-19925. (Year: 2008).*

Han et al., 2019. Application of digital PCR for assessing DNA fragmentation in cytotoxicity response. Biochimica et Biophysica Acta (BBA)—General Subjects, 1863(8), pp. 1235-1242. (Year: 2019).*

International Search Report and Written Opinion of the International Searching Authority mailed Aug. 6, 2024 in International Patent Application No. PCT/CN2024/091880. 7 pages.

Chan, K.C. Allen et al.; "Size Distributions of Maternal and Fetal DNA in Maternal Plasma"; Clinical Chemistry; 2004; vol. 50, No. 1; pp. 88-92.

Ellinger, Jörg et al.; "Cell-free Circulating DNA: Diagnostic Value in Patients with Testicular Germ Cell Cancer"; The Journal of Urology; Jan. 2009; vol. 181, No. 1; pp. 363-371.

Fan, H. Christina et al.; "Analysis of the Size Distributions of Fetal and Maternal Cell-Free DNA by Paired-End Sequencing"; Clinical Chemistry; 2010; vol. 56, No. 8; pp. 1279-1286.

Hao, T.B. et al.; "Circulating cell-free DNA in serum as a biomarker for diagnosis and prognostic prediction of colorectal cancer"; British Journal of Cancer; 2014; vol. 111, No. 8; p. 1482-1489.

Lun, Fiona M.F. et al.; "Noninvasive prenatal diagnosis of monogenic diseases by digital size selection and relative mutation dosage on DNA in maternal plasma"; PNAS; Dec. 16, 2008; vol. 105, No. 50; pp. 19920-19925.

Madhavan, Dharanija et al.; "Plasma DNA integrity as a biomarker for primary and metastatic breast cancer and potential marker for early diagnosis"; Breast Cancer Research and Treatment; 2014; vol. 146, No. 1; pp. 163-174.

(Continued)

*Primary Examiner* — Gary Benzion
*Assistant Examiner* — Olayinka A Oyeyemi
(74) *Attorney, Agent, or Firm* — Kilpatrick Townsend & Stockton LLP

(57) ABSTRACT

Methods and systems are described herein that include using multiplexed digital amplification reactions to measure the sizes of a plurality of nucleic acid molecules. In various embodiments, the digital amplification reactions use multiple pairs of separate forward and reverse primer pairs to amplify targeted regions of the nucleic acid molecules, where the targeted regions are separated by a specified number of base pairs. In other embodiments, the digital amplification reactions use multiple primer pairs that share a common pair to amplify targeted regions that overlap with one another. The methods and systems are particularly useful for determining the size distributions of the nucleic acid molecules, or classifying a pathology of a subject from whom the nucleic acid molecules are sampled. Advantageously, the methods and systems can measure the sizes of long nucleic acid molecules without relying on inefficient amplification of very long amplicons.

19 Claims, 20 Drawing Sheets

Specification includes a Sequence Listing.

(56) References Cited

OTHER PUBLICATIONS

Mouliere. Florent et al.; "High Fragmentation Characterizes Tumour-Derived Circulating DNA"; PLoS ONE; Sep. 2011; vol. 6, Issue 9; e23418; pp. 1-10.

* cited by examiner

PET group Control group

Single molecule sequencing (e.g. SMRT-seq or nanopore sequencing) for plasma cell-free DNA Simulate digital PCR readouts
- different amplicon sizes
- different number of molecules

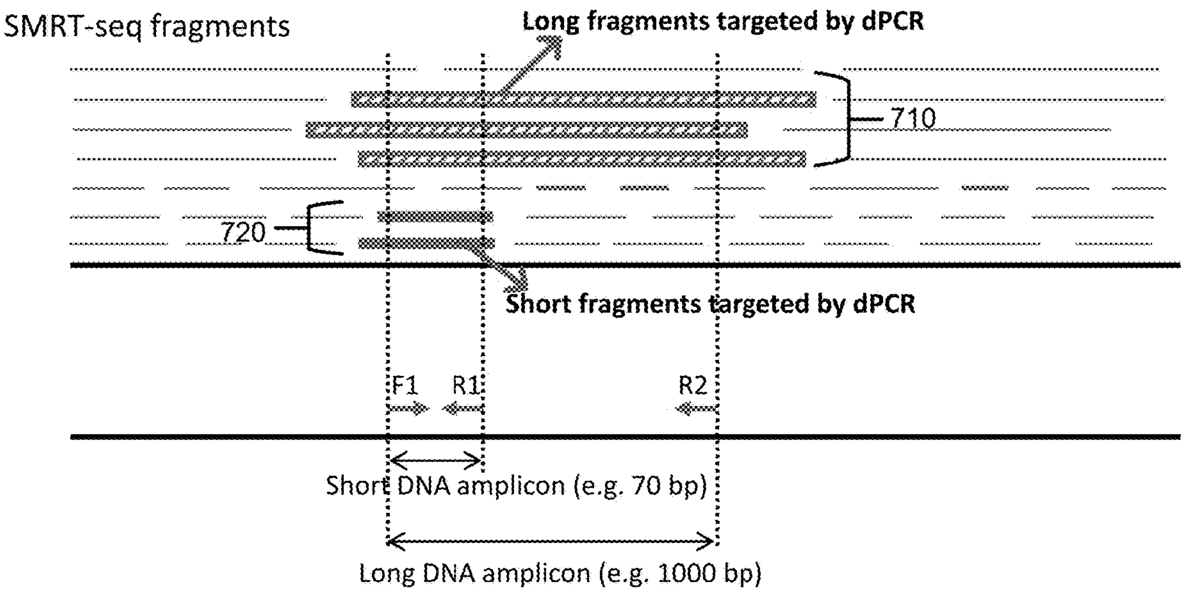

Inferring the percentage long DNA fragments (%), denoted by L%

Comparing L% values between the two groups
Determining the optimal sizes for the short and long amplicons and the least no. of fragments required

FIG. 7A

EFFICIENT DIGITAL MEASUREMENT OF LONG NUCLEIC ACID FRAGMENTS

CROSS-REFERENCES TO RELATED APPLICATIONS

The present application claims priority from and is a nonprovisional application of U.S. Provisional Application No. 63/465,161, entitled "Efficient Digital Measurement of Long Nucleic Acid Fragments," filed May 9, 2023, the entire contents of which are herein incorporated by reference for all purposes.

SEQUENCE LISTING

The instant application contains a Sequence Listing which has been submitted electronically in XML format and is hereby incorporated by reference in its entirety. Said XML copy, created on Jul. 3, 2024, is named 108473-8007US1-1441092_SL.xml and is 12,512 bytes in size.

BACKGROUND

Digital polymerase chain reaction (PCR) allows absolute quantification of target DNA in a sample. In digital PCR, a DNA sample is partitioned into compartments such that a separate PCR reaction can be carried out in each individual partition (Saiki, et al. 1988, Science, 239 (4839): 487-91; Vogelstein & Kinzler. 1999, Proc. Natl. Acad. Sci. USA, 96, 9236-9241). Conventionally, one would use a single primer pair to amplify a target region of a certain size (referred to as an amplicon size, i.e., a size defined by an intra-primer-pair distance) from among the molecules of interest within a reaction partition. A fluorescently labelled, target-specific probe which recognizes a specific sequence within the amplicon could then be used to detect the target amplicons within each reaction partition. Those reaction partitions with a detectable fluorescence signal would contain at least one copy of the target DNA.

A digital PCR or quantitative PCR assay using a single primer pair does not, however, provide any information related to the size distribution of DNA in a sample. In this regard, previous studies developed PCR assays targeting amplicons of different sizes to analyze the size distribution of DNA molecule in a sample. For example, Chan et al. analyzed the fraction of plasma DNA molecules exceeding certain sizes using real-time PCR with a panel of primer pairs, including one forward primer and several reverse primers, each of which produces an amplicon of a different size (Chan, et al. 2004, Clin. Chem., 50 (1), 88-92). Alcaide et al. employed a similar design using a digital PCR platform instead of a real-time PCR platform, enabling the multiplex amplification of different-sized amplicons in a single digital PCR reaction (Alcaide et al. 2020, Sci. Rep., 10 (1): 12564). Obstacles remain, though, in applying these and similar approaches. For example, the use of longer amplicons (e.g., those of greater than 1 kb) to analyze the size distribution of DNA would be limited by the amplification efficiency of the DNA polymerase which usually does not favor the amplification of target DNA above 1 kb.

BRIEF SUMMARY

Various embodiments are provided for using multiplexed digital amplification reactions, e.g., digital PCR, to analyze the size of nucleic acid molecules, e.g., cell-free DNA, within a biological sample. One example purpose is determining a size distribution of the nucleic acid molecules in the biological sample. Various sets of amplification primers and probes can be used for this purpose. Certain combinations of primer sets useful for this purpose include separate forward and reverse primers for each set, such that a forward primer of one primer set is downstream of a reverse primer of another primer set. Such a configuration of primer sets can enable simultaneous measurement of various sizes of cell-free DNA fragments, including long DNA fragments, e.g., fragments having a size greater than 400 bp or other size described herein. Other combinations of primer sets useful for this purpose include those with a shared primer that is common among each set.

Another example purpose is determining a pathology of a subject using a biological sample including nucleic acid molecules, e.g., cell-free DNA. An example of such a pathology is preeclampsia for a subject that is pregnant with a fetus (e.g., a single fetus or multiple fetuses). Various sets of amplification primers and probes can be used for this purpose. A classification of a subject pathology may be determined based on relative amounts of amplification reactions that are positive for the different probes in the multiplexed digital reactions. Certain combinations of primer sets useful for this purpose include separate forward and reverse primers for each set, such that a forward primer of one primer set is downstream of a reverse primer of another primer set. Other combinations of primer sets useful for this purpose include those with a shared primer that is common among each set.

These and other embodiments of the disclosure are described in detail below. For example, other embodiments are directed to systems, devices, and computer readable media associated with methods described herein.

Reference to the remaining portions of the specification, including the drawings and claims, will realize other features and advantages of the present disclosure. Further features and advantages of the present disclosure, as well as the structure and operation of various embodiments of the present disclosure, are described in detail below with respect to the accompanying drawings. In the drawings, like reference numbers can indicate identical or functionally similar elements.

BRIEF DESCRIPTION OF THE DRAWINGS

FIG. 7A presents a schematic illustration of an exemplary simulation using long DNA sequencing data to guide digital amplification reaction design in accordance with a provided embodiment.

TERMS

Figure 1A:
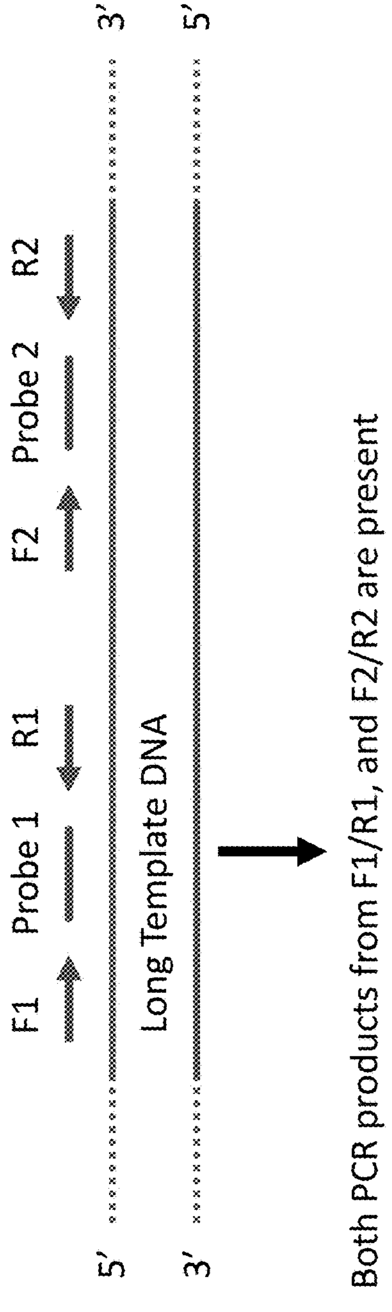
FIG. 1A presents a schematic illustration of an exemplary digital assay with two separate primer pairs for deducing the size of a relatively long template nucleic acid molecule in accordance with a provided embodiment.

A "biological sample" refers to any sample that is taken from a subject (e.g., a human or other animal), such as a pregnant woman, a person with cancer or other disorder, or a person suspected of having cancer or other disorder, an organ transplant recipient or a subject suspected of having a disease process involving an organ (e.g., the heart in myocardial infarction, or the brain in stroke, or the hematopoietic system in anemia) and contains one or more nucleic acid molecule(s) of interest (e.g., DNA and/or RNA). The biological sample can be a bodily fluid, such as blood, plasma, serum, urine, vaginal fluid, fluid from a hydrocele (e.g., of the testis), vaginal flushing fluids, pleural fluid, ascitic fluid, cerebrospinal fluid, saliva, sweat, tears, sputum, bronchoalveolar lavage fluid, discharge fluid from the nipple, aspiration fluid from different parts of the body (e.g., thyroid, breast), intraocular fluids (e.g., the aqueous humor), amniotic fluid, etc. Stool samples can also be used. In various embodiments, the majority of DNA in a biological sample (e.g., that has been enriched for cell-free DNA, such as a plasma sample obtained via a centrifugation protocol) can be cell-free, e.g., greater than 50%, 60%, 70%, 80%, 90%, 95%, or 99% of the DNA can be cell-free. A centrifugation protocol for enriching cell-free DNA from a biological sample can include, for example, centrifuging the biological sample at 1,600 g×10 minutes, obtaining the fluid part of the centrifuged sample, and re-centrifuging at for example, 16,000 g for another 10 minutes to remove residual cells. As part of an analysis of a biological sample, a statistically significant number of cell-free DNA molecules can be analyzed (e.g., to provide an accurate measurement) for a biological sample. In some embodiments, at least 1,000 cell-free DNA molecules are analyzed. In other embodiments, at least 10,000 or 50,000 or 100,000 or 500,000 or 1,000,000 or 5,000,000 cell-free DNA molecules, or more, can be analyzed. At least a same number of sequence reads can be analyzed. Any amount described herein can be any of the numbers listed above. Examples sizes of a sample can include 30, 50, 100, 200, 300, 500, 1,000, 5,000, or 10,000 or more nanograms, or 1, 2, 3, 4, 5, 6, 7, 8, 9, or 10 ml.

A "nucleic acid molecule" or "polynucleotide" (also referred to as a nucleic acid fragment) refers to deoxyribonucleic acids (DNA) or ribonucleic acids (RNA) and polymers thereof in either single- or double-stranded form. A fragment can refer to a portion of a polynucleotide or polypeptide sequence that comprises at least 3 consecutive nucleotides. A nucleic acid fragment can retain the biological activity and/or some characteristics of the parent polypeptide. Unless specifically limited, the term encompasses nucleic acids containing known nucleotide analogs or modified backbone residues or linkages, which are synthetic, naturally occurring, and non-naturally occurring, that have similar binding properties as the reference nucleic acid and are metabolized in a manner similar to reference nucleotides. Examples of such analogs include, without limitation, phosphorothioates, phosphoramidates, methyl phosphonates, chiral-methyl phosphonates, 2-O-methyl ribonucleotides, and peptide nucleic acids (PNAs). A nucleic acid fragment can be a linear fragment or a circular fragment.

Non-limiting examples of polynucleotides or nucleic acid molecules include DNA, RNA, coding or noncoding regions of a gene or gene fragment, intergenic DNA, loci (locus) defined from linkage analysis, exons, introns, messenger RNA (mRNA), transfer RNA (tRNA), ribosomal RNA (rRNA), short interfering RNA (siRNA), short-hairpin RNA (shRNA), micro-RNA (miRNA), small nucleolar RNA (snoRNA), ribozymes, deoxynucleotides (dNTPs), or dideoxynucleotides (ddNTPs). Polynucleotides can also include complementary DNA (cDNA), which is a DNA representation of mRNA, usually obtained by reverse transcription of messenger RNA (mRNA) or by amplification. Polynucleotides can also include DNA molecules produced synthetically or by amplification, genomic DNA (gDNA), recombinant polynucleotides, branched polynucleotides, plasmids, vectors, isolated DNA of any sequence, isolated RNA of any sequence, nucleic acid probes, or primers. A polynucleotide can comprise modified nucleotides, such as methylated nucleotides and nucleotide analogs. If present, modifications to the nucleotide structure can be imparted before or after assembly of the polymer. The sequence of nucleotides can be interrupted by non-nucleotide components. A polynucleotide can be further modified after polymerization, such as by conjugation with a labeling component. Polynucleotide sequences, when provided, are listed in the 5' to 3' direction, unless stated otherwise.

Nucleic acid molecules or polynucleotides can be double- or triple-stranded nucleic acids, as well as single-stranded molecules. In double- or triple-stranded nucleic acids, the nucleic acid strands need not be coextensive, for example, a double-stranded nucleic acid need not be double-stranded along the entire length of both strands.

A "primer" refers to an oligonucleotide that can be used in an amplification method, such as a polymerase chain reaction (PCR), to amplify a predetermined target nucleotide sequence or region. In a typical PCR, at least one set of primers, one forward primer and one reverse primer, are needed to amplify a target polynucleotide sequence or region.

Conventionally, when a target DNA sequence consisting of a (+) strand and a (−) strand is amplified, a forward primer is an oligonucleotide that can hybridize to the 3' end of the (−) strand under the reaction condition and can therefore initiate the polymerization of a new (+) strand; whereas a reverse primer is an oligonucleotide that can hybridize to the 3' end of the (+) strand under the reaction condition and can therefore initiate the polymerization of a new (−) strand. As an example, a forward primer may have the same sequence as the 5' end of the (+) strand, and a reverse primer may have the same sequence as the 5' end of the (−) strand.

The abbreviation "bp" refers to base pairs. In some instances, "bp" may be used to denote a length of a DNA fragment, even though the DNA fragment may be single stranded and does not include a base pair. In the context of single-stranded DNA, "bp" may be interpreted as providing the length in nucleotides.

The terms "size profile" and "size distribution" generally relate to the sizes of DNA fragments in a biological sample. A size profile may be a histogram that provides a distribution of an amount of DNA fragments at a variety of sizes. Various statistical parameters (also referred to as size parameters or just parameter) can distinguish one size profile to another. One parameter is the percentage of DNA fragment of a particular size or range of sizes relative to all DNA fragments or relative to DNA fragments of another size or range.

The term "parameter" as used herein means a numerical value that characterizes a quantitative data set and/or a numerical relationship between quantitative data sets. For example, a ratio (or function of a ratio) between a first amount of a first nucleic acid sequence and a second amount of a second nucleic acid sequence is a parameter. The parameter can be used to determine any classification described herein, e.g., with respect to fetal, cancer, or transplant analysis.

A "separation value" corresponds to a difference or a ratio involving two values, e.g., two fractional contributions or two methylation levels. A separation value is an example of a parameter. The separation value could be a simple difference or ratio. As examples, a direct ratio of $x/y$ is a separation value, as well as $x/(x+y)$. Other examples are $y/x$ and $y/(x+y)$. The separation value can include other factors, e.g., multiplicative factors. As other examples, a difference or ratio of functions of the values can be used, e.g., a difference or ratio of the natural logarithms (ln) of the two values. A separation value can include a difference and a ratio, e.g., $(x-y)/(x+y)$. A separation value can be compared to a threshold to determine whether the separation between the two values is statistically significant. A separation value is an example of a relative amount.

The terms "cutoff" and "threshold" refer to predetermined numbers used in an operation. For example, a cutoff size can refer to a size above which fragments are excluded. As another example, a threshold value may be a value above or below which a particular classification applies. Either of these terms can be used in either of these contexts. A cutoff or threshold may be "a reference value" or derived from a reference value that is representative of a particular classification or discriminates between two or more classifications. A cutoff may be predetermined with or without reference to the characteristics of the sample or the subject. For example, cutoffs may be chosen based on the age or sex of the tested subject. A cutoff may be chosen after and based on output of the test data. For example, certain cutoffs may be used when the sequencing of a sample reaches a certain depth. As another example, reference subjects with known classifications of one or more conditions and measured characteristic values (e.g., a methylation level, a statistical size value, or a count) can be used to determine reference levels to discriminate between the different conditions and/or classifications of a condition (e.g., whether the subject has the condition). A reference value can be selected as representative of one classification (e.g., a mean) or a value that is between two clusters of the metrics (e.g., chosen to obtain a desired sensitivity and specificity). As another example, a reference value can be determined based on statistical simulations of samples. Any of these terms can be used in any of these contexts. Such a reference value can be determined in various ways, as will be appreciated by the skilled person. For example, metrics can be determined for two different cohorts of subjects with different known classifications, and a reference value can be selected as representative of one classification (e.g., a mean) or a value that is between two clusters of the metrics (e.g., chosen to obtain a desired sensitivity and specificity). As another example, a reference value can be determined based on statistical simulations of samples. A particular value for a cutoff, threshold, reference, etc. can be determined based on a desired accuracy (e.g., a sensitivity and specificity).

The term "classification" as used herein refers to any number(s) or other characters(s) that are associated with a particular property of a sample. For example, a "+" symbol (or the word "positive") could signify that a sample is classified as having deletions or amplifications, or as being derived from a subject having a pathology. The classification can be binary (e.g., positive or negative) or have more levels of classification (e.g., a scale from 1 to 10 or 0 to 1), including probabilities. Different techniques for determining a classification can be combined to obtain a final classification from the initial or intermediate classification for each of the different techniques, e.g., by majority vote or a requirement that all initial/intermediate classifications are the same (e.g., positive).

A "level of a pathology" can refer to an amount, degree, or severity of a pathology associated with an organism. A heathy state of a subject can be considered a classification of no pathology.

The terms "about" and "approximately" can mean within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, up to 10%, up to 5%, or up to 1% of a given value. Alternatively, particularly with respect to biological systems or processes, the term "about" or "approximately" can mean within an order of magnitude, within 5-fold, and more preferably within 2-fold, of a value. Where particular values are described in the application and claims, unless otherwise stated the term "about" meaning within an acceptable error range for the particular value should be assumed. The term "about" can have the meaning as commonly understood by one of ordinary skill in the art. The term "about" can refer to +10%. The term "about" can refer to +5%.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within embodiments of the present disclosure. The upper and lower limits of these smaller ranges may independently be included or excluded in the range, and each range where either, neither, or both limits are included in the smaller ranges is also encompassed within the present disclosure, subject to any specifically excluded limit in the stated range. Where the stated range includes one or both of the limits, ranges excluding either or both of those included limits are also included in the present disclosure.

Standard abbreviations may be used, e.g., bp, base pair(s); kb, kilobase(s); pi, picoliter(s); s or see, second(s); min, minute(s); h or hr, hour(s); aa, amino acid(s); nt, nucleotide(s); and the like.

Unless defined otherwise, all technical and scientific terms used herein have the same meaning as commonly understood by one of ordinary skill in the art to which this disclosure belongs. Although any methods and materials similar or equivalent to those described herein can be used in the practice or testing of the embodiments of the present disclosure, some potential and exemplary methods and materials may now be described.

DETAILED DESCRIPTION

Before the present invention is described in greater detail, it is to be understood that this invention is not limited to particular embodiments described, as such may vary. It is also to be understood that the terminology used herein is for the purpose of describing particular embodiments only, and is not intended to be limiting, since the scope of the present invention will be limited only by the appended claims. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric.

The present disclosure provides multiplexed digital amplification reactions, e.g., multiplex digital PCR assays, where each of the amplification reactions contains two or more primer pairs that can be annealed to a template DNA. In some embodiments, a desired and predetermined nucleotide distance (i.e., an inter-primer-pair spanning distance) exists between the amplicons associated with each primer pair. In some embodiments, the length (i.e., an intra-primer-pair distance) of the amplicon associated with each of the two or more primer pairs can be relatively small, such that the amplicon can be effectively amplified, e.g., to generate fluorescent signals using a probe for detecting the amplicon. In this way, the simultaneous positive detection of two or more short-sized amplicons within one reaction partition of the multiplexed digital reactions (i.e., a colocalization of signals) can be translated to the detection of a long DNA molecule.

As a nonlimiting example, primer pairs with an inter-primer-pair spanning distance of 1000 bp can be used. Each primer pair can be coupled with a different type of probe which emits a different fluorescence light. A template DNA with a size of 1000 bp or above would be determined to be present in this example when two primer pairs initiate amplifications resulting in emission of the two types of detectable fluorescence signals from two different probes (e.g., forming a mixed-color light) in a reaction partition. In contrast, a template DNA with a size of less than 1000 bp would be determined to be present in this example when only one of two primer pairs could initiate amplification resulting in emission of only one type of detectable fluorescence signal in a reaction partition.

In other embodiments, the amplicons associated with the two or more primer pairs overlap, such that a smaller amplicon associated with a first primer pair corresponds to a subsequence of a larger amplicon associated with a second primer pair. In some such embodiments, one primer of the first primer pair is identical to one primer of the second primer pair. The simultaneous positive detection of both amplicons within one reaction partition of the multiplexed digital reactions can therefore be translated to the detection of a longer DNA molecule, whereas the positive detection of only the smaller amplicon within one reaction partition can be translated into detection of a smaller DNA molecule.

The present disclosure thus advantageously provides methods and related compositions and systems useful for measuring the sizes of nucleic acid molecules without the greater expense or time required by other procedures, such as sequencing. The provided materials and methods are particularly beneficial in allowing for straightforward and inexpensive determinations of the sizes or size distributions of long DNA molecules, e.g., long cell-free DNA molecules. Additional benefits provided by the disclosure relate to improvements for determining a pathology classification for a subject, where the classification is related to a size distribution of nucleic acid molecules in a sample from the subject. The disclosure further provides improved techniques for designing digital amplification reactions with enhanced ability to differentiate nucleic acid molecules of different sizes, and to distinguish different classifications or levels of various pathologies such as preeclampsia.

Before the present invention is described in greater detail, it is to be understood that this invention is not limited to particular embodiments described, as such may vary. It is also to be understood that the terminology used herein is for the purpose of describing particular embodiments only, and is not intended to be limiting, since the scope of the present invention will be limited only by the appended claims. Efforts have been made to ensure accuracy with respect to numbers used (e.g, amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric.

I. Multiplex Digital Amplification Reactions

The present disclosure generally relates to methods for analyzing nucleic acid molecules, e.g., cell-free nucleic acid molecules from a biological sample, using multiplexed digital amplification reactions. Digital amplification refers to a process of amplifying a small amount of nucleic acid molecules to generate a larger number of identical copies for analysis, where a sample of the nucleic acid molecules is first compartmentalized or partitioned into many individual amplification reactions. The resulting amplification products can then be analyzed to determine the number of positive and negative reactions from among the many individual reactions. This number can be used to precisely quantify the number of target molecules in the original sample. Since the compartments are typically very small and contain a limited amount of sample, the method has high sensitivity and can detect very low levels of target nucleic acids in a sample.

Multiplexed digital amplification refers to a digital amplification method involving the simultaneous detection of multiple targets within each individual compartmentalized amplification reaction. This technique generally requires two or more probes that can be distinguished from one another and detected simultaneously. For example, a multiplexed digital amplification reaction can use two or more fluorescently labeled probes, one for each target amplicon of the amplification reaction, where each probe emits fluorescence light having a different wavelength. As an individual target amplicon is amplified in a particular compartmentalized reaction, light emitted from that compartment and having the wavelength of the probe associated with that amplicon will increase. Signals associated with various combinations of the probes can be identified by the simultaneous detection of emitted fluorescence light having different corresponding combinations of wavelengths. In this way, the detection of multiple signals from a single compartment of the multiplexed amplification reaction can be used to determine that the single compartment includes positive reactions amplifying multiple amplicons associated with the multiple detected signals.

The embodiments provided herein advantageously use multiplexed amplification reactions to simultaneously detect amplicons of different regions from the same template nucleic acid. The multiplexed reactions can thus provide information about, for example, the size distribution of template nucleic acid molecules in a sample, or the classification of a pathology related to the relative amounts of the different amplicon regions present in the template nucleic acid molecule. This contrasts with more general uses for multiplexed amplification reactions, which instead typically detect amplicons representing different alleles at the same locus, or amplicons representing different loci, e.g., different genes on different chromosomes.

In some embodiments, the amplification reaction within each of the compartmentalized digital amplification reactions is a polymerase chain reaction (PCR). In some embodiments, the multiplexed digital amplification reactions are compartmentalized using a microfluidics system. A "microfluidics system" refers to a system, typically an automated system, that can manipulate very small volume of fluid samples with required precision. A microfluidics system suitable for use with the provided methods is one capable of accurately taking one or more aliquots from a fluid sample and distributing the aliquots into separate, individually defined compartments. In some embodiments, the compartments aliquoted by a microfluidic system are volumes within individual wells of a multi-well microplate. In some embodiments, the compartments aliquoted by a microfluidic system are individual droplets, and the digital amplification reactions are droplet digital PCR reactions. The volume of each aliquot can be, for example, in the range of nanoliters ($10^{-9}$ liter) to picoliters ($10^{-12}$ liter).

In some embodiments, the multiplexed digital amplification reactions use polony PCR. In some embodiments, the partitioning of the multiplexed digital amplification reactions uses beads or surfaces (e.g., partitioning on glass or in a flow cell). In some embodiments, the multiplexed digital amplification reactions are emulsion polymerase chain reactions. An "emulsion polymerase chain reaction" refers to a polymerase chain reaction in which the reaction mixture, an aqueous solution, is added into a large volume of a second liquid phase that is water-insoluble, e.g., oil. The suspension can be emulsified prior to the amplification process, so that the aqueous droplets of the reaction mixture act as micro-reactors and therefore achieve a higher concentration for a target nucleic acid in at least some of the micro-reactors.

"BEAMing" (beads, emulsions, amplification, and magnetics) refers to a modified emulsion PCR process suitable for use with the provided methods. In this process, at least one of the PCR primers is conjugated with a molecule that is a partner of a known binding pair. For example, a biotin moiety may be conjugated to a forward primer used in the PCR. In each reaction compartment, one or more metal beads coated with the other member of the binding pair, e.g., streptavidin, are provided. Upon completion of the amplification step, the amplicon from the labeled primer is adsorbed to the coated bead(s), which in turn can be concentrated and isolated by magnetic beads. For more description of BEAMing, see, e.g., Diehl et al., Nat. Methods. 3, (2006): 551.

In some embodiments, the nucleic acid molecules analyzed using the provided multiplexed digital amplification reactions are DNA molecules. In some embodiments, the nucleic acid molecules are RNA molecules, and the digital amplification reactions include a reverse transcriptase enzyme in an amount effective to reverse transcribe the RNA molecules to complementary DNA (cDNA) molecules, which can then be amplified, e.g., by PCR. In some embodiments, the partitioning or compartmentalizing of the nucleic acid molecules results in the plurality of the multiplexed digital amplification reactions having an average of one nucleic acid molecule per digital amplification reaction.

II. Measuring Size Using Separate Primer Sets

In some aspects, the present disclosure provides methods for measuring the sizes of nucleic acid molecules, e.g., a plurality of cell-free nucleic acid molecules from a biological sample, where the methods involve amplifying two or more separate and non-overlapping regions of a reference sequence, at least a portion of which is present in or complementary to the nucleic acid molecules. Positive amplification of more than one of these targeted regions from a nucleic acid molecule indicates that the nucleic acid molecule has a sequence length at least long enough to cover or include each of the successfully amplified regions. Positive amplification of fewer targeted regions, e.g., only one targeted region, indicates that the nucleic acid molecule instead has a length insufficiently long enough to cover or include each region targeted for amplification. For each region targeted for amplification, the multiplexed amplification reactions include a different and distinctly observable probe, e.g., a fluorescent probe, and complete separate pairs of amplification primers, e.g., a forward and a reverse PCR primer. These provided methods preferably involve multiplexed digital PCR and cannot be operated using real-time PCR. The provided methods are particularly advantageous for measuring the size of relatively long nucleic acid molecules, without needing to rely on the frequently inefficient amplification of relatively long amplicons.

A. Two Primer Sets

FIG. 1 provides a schematic illustration of a disclosed multiplexed digital amplification assay for measuring the size of a nucleic acid molecule using two separate sets of PCR primer pairs. Each amplification reaction of the multiplexed digital assay includes, among other necessary enzymes, reagents, buffers, and additional components of PCR amplification, four PCR primers. Two of these four primers are forward (F1) and reverse (R1) primers targeting amplification of a first region of the nucleic acid molecule. The other two of the four primers are forward (F2) and reverse (R2) primers targeting amplification of a second region of the nucleic acid molecule. The sequence of each of the primers can be determined based on a reference sequence, at least a portion of which may be present on or complementary to the nucleic acid molecule. For example, the F1 and R1 primers can be designed to correspond to, e.g., be complementary to, the sequence of the first region as it appears in the reference sequence. The F2 and R2 primers can likewise be designed to correspond to, e.g., be complementary to, the sequence of the second region as it appears in the reference sequence.

As shown in the illustration of FIG. 1, the second forward primer (F2) is downstream from the first reverse primer (R1). In this way, the second region targeted by the second forward (F2) and reverse (R2) primers is separate from, and does not overlap with, the first region targeted by the first forward (F1) and reverse (R1) primers. The first and second primer pairs can be designed or configured such that the second region is located a specified number of bases from the first region in the reference sequence. For example, the specified number of bases between the first region and the second region can be less than about 5 kilobases, e.g., less than about 3000 bp, less than about 2000 bp, less than about 1500 bp, less than about 1000 bp, less than about 800 bp, less than about 600 bp, less than about 500 bp, less than about 400 bp, less than about 300 bp, less than about 250 bp, or less than about 200 bp. In terms of lower limits, the specified number of bases between the first region and the second region can be, for example, greater than about 150 bp, e.g., greater than about 200 bp, greater than about 250 bp, greater than about 300 bp, greater than about 400 bp, greater than about 500 bp, greater than about 600 bp, greater than about 800 bp, greater than about 1000 bp, greater than about 1500 bp, greater than about 2000 bp, or greater than about 3000 bp.

The selection of the specified distance between the first and second regions targeted, respectively, by the first (F1/R1) and second (F1/R1) primer sets of the digital amplification reactions can determine what size of nucleic acid molecules can be measured using the provided method. For example, FIG. 1A illustrates a compartmentalized amplification reaction in which the nucleic acid molecule, i.e., template DNA, is a relatively long nucleic acid molecule spanning the entire targeted first and second regions and the specified distance between the regions. Accordingly, the amplification reaction of this compartment will produce PCR products corresponding to both the first and the second regions, and the compartment will be identified as including a nucleic acid molecule that is at least the specified number of bases in length and that covers both the first and second target regions. In this way, the specified distance between the first and second regions relates to the length of nucleic acid molecules that can be measured.

Figure 1B:
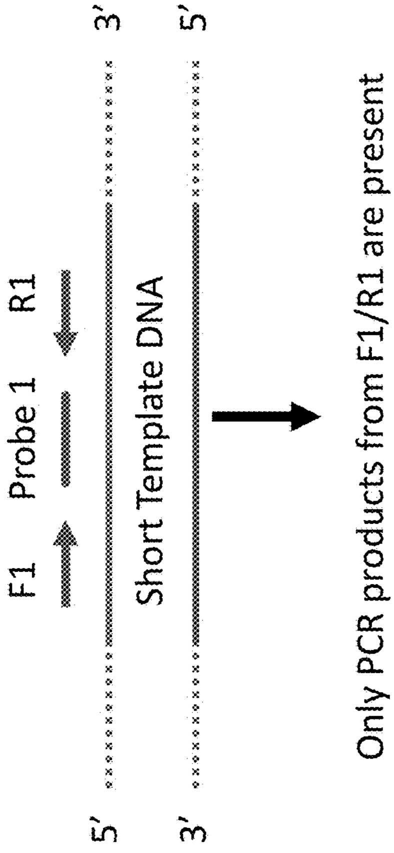
FIG. 1B presents a schematic illustration of an exemplary digital assay with two separate primer pairs for deducing the size of a relatively short template nucleic acid molecule in accordance with a provided embodiment.

FIG. 1B illustrates another compartmentalized amplification reaction containing a nucleic acid molecule, i.e., template DNA, that is a relatively short nucleic acid molecule spanning the entire targeted first region but lacking the targeted second region. The amplification reaction of this compartment will produce PCR products corresponding to the first region, but not to the second region. The compartment will therefore be identified as not including a nucleic acid molecule that is at least the specified number of bases in length and that covers both the first and second target regions.

The first and second primer sets of the multiplexed digital amplification reactions can individually be designed or configured to target amplicons that are relatively short in length. The use of short amplicons in the provided analytical method can in at least some instances beneficially increase the accuracy and efficiency of the method, because PCR reactions are generally more effective in amplifying shorter regions than larger regions. The provided methods can therefore advantageously improve the accuracy and efficiency of using amplifications to measure the size of relatively long nucleic acid molecules, because the methods require amplification of multiple relatively short regions of the molecules, rather than a single larger region representative of the overall length of the relatively long molecule. Each region, e.g., the first region and the second region, targeted for amplification can independently have a length that is, for example, less than about 1000 bp, e.g., less than about 900 bp, less than about 800 bp, less than about 700 bp, less than about 600 bp, less than about 500 bp, less than about 400 bp, less than about 300, bp, less than about 250 bp, less than about 200 bp, less than about 150 bp, less than about 100 bp, or less than about 70 bp. In terms of lower limits, each region targeted for amplification can independently have a length that is, for example, greater than about 50 bp, e.g., greater than about 70 bp, greater than about 100 bp, greater than about 150 bp, greater than about 200 bp, greater than about 250 bp, greater than about 300 bp, greater than about 400 bp, greater than about 500 bp, greater than about 600 bp, greater than about 700 bp, greater than about 800 bp, or greater than about 900 bp.

As also shown in FIGS. 1A and 1B, each amplification reaction of the multiplexed digital assay also includes a first probe or reporter (Probe 1) and a second probe or reporter (Probe 2). The first probe corresponds to the first region targeted for amplification by the first forward (F1) and first reverse (R1) primers of the first primer set. The second probe corresponds to the second region targeted for amplification by the second forward (F2) and second reverse (R2) primers of the second primer set. The first probe of the first primer set produces a detectable signal that is distinguishable from a different detectable signal produced by the second probe of the second primer set. In this way, a first signal from the first probe can be quantifiably detected simultaneously with the quantifiable detection of a second signal from the second probe. The signal strengths emitted from the probes in a compartmentalized reaction are generally proportionate to the amount of amplification products produced in that reaction. For example, flowing the amplification reaction illustrated in FIG. 1A, PCR amplification products associated with both the F1/R1 primers and the F2/R2 primers are present. As a result, signals from both Probe 1 and Probe 2 can be detected from this compartmentalized reaction. Following the amplification reaction illustrated in FIG. 1B, only PCR amplification products associated with the F1/R1 primers are present. As a result, only the signal from Probe 1 can be detected from this compartmentalized reaction. In some embodiments, the first probe and the second probe each independently include a different fluorescent reporter. In some embodiments, the first signal and the second signal each independently include a fluorescence emission light having a different wavelength.

In some embodiments, the measuring of the size of nucleic acid molecules as illustrated in FIGS. 1A and 1B includes determining which of the plurality of multiplexed digital amplification reactions includes a nucleic acid molecule sufficiently long enough to include the first region, the second region, and the specified distance between the first and second regions. For example, after completing the amplification reactions, the number of compartments, e.g., droplets, emitting the first signal from the first probe and the second signal from the second probe can be counted. In some embodiments, the measuring of the size of nucleic acid molecules as illustrated in FIGS. 1A and 1B further includes determining which of the plurality of multiplexed digital amplification reactions included a nucleic acid molecule only long enough to include one of the first region or the second region. For example, after completing the amplification reactions, the number of compartments, e.g., droplets, emitting only one of the first signal from the first probe and the second signal from the second probe can be counted. In some embodiments, the count of compartments emitting both the first and second signals is related to the count of compartments emitting only one of the first and second signals. For example, the two different counts can be used to calculate a ratio of long template DNA to short template DNA among the compartmentalized reactions, or a ratio of short template DNA to long template DNA among the reactions. These ratios, or other derived parameters, can be used to determine, for example, the relative size distribution of nucleic acid molecules in the original sample that comprised the molecules.

B. More than Two Primers Sets

Figure 2:
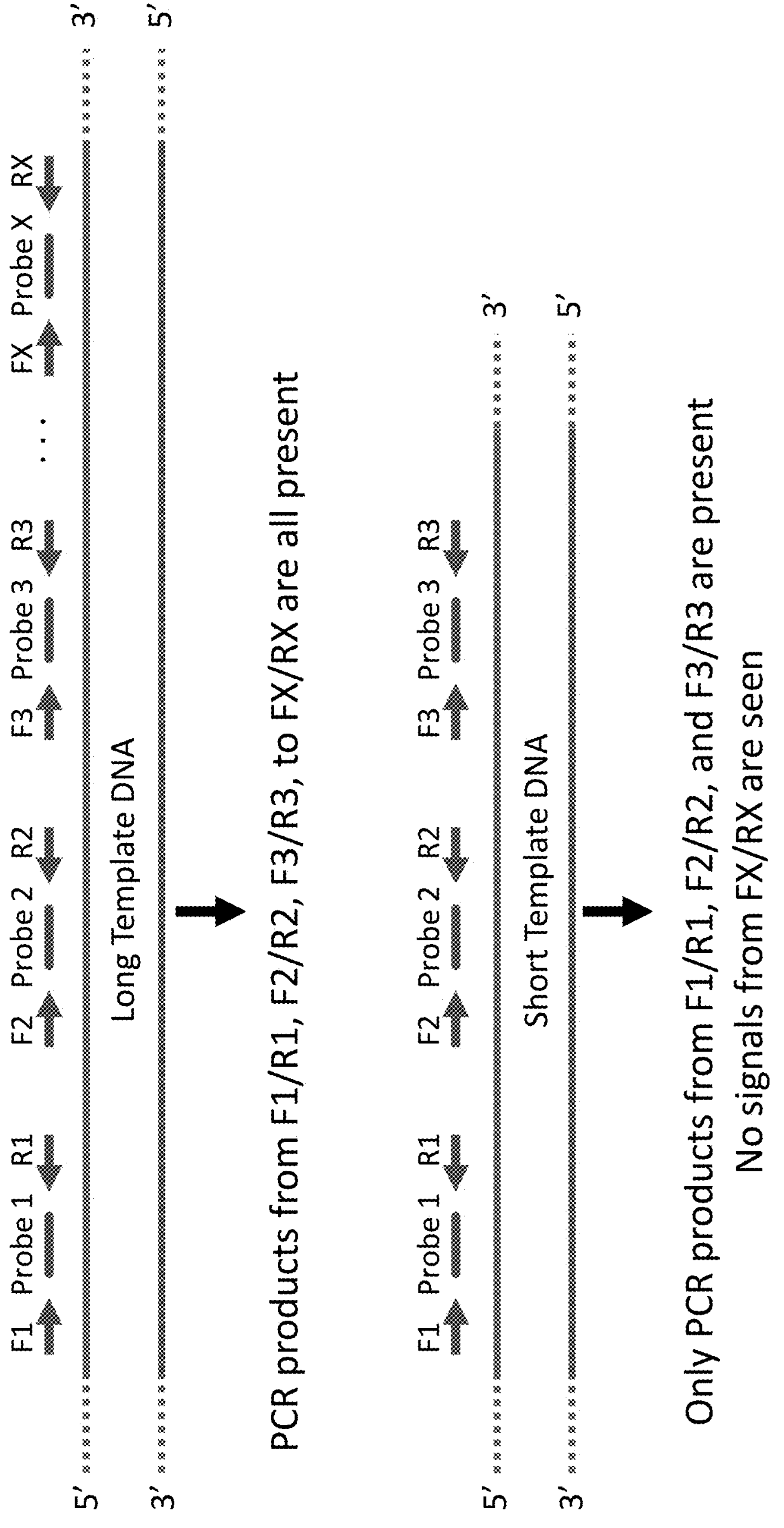
FIG. 2 presents a schematic illustration of an exemplary digital assay with more than two separate primer pairs for deducing multiple sizes of nucleic acids in accordance with a provided embodiment.

FIG. 2 provides an illustration of another configuration of this method useful for measuring two or more different sizes of nucleic acid molecules. This configuration of the method uses three or more separate sets of PCR primer pairs. For example, and as illustrated in FIG. 2, first forward (F1) and reverse (R1) primers can target a first region of the nucleic acid molecule. Second forward (F1) and reverse (R2) primers can target a second region of the nucleic acid molecule. Third forward (F1) and reverse (R3) primers can target a third region of the nucleic acid molecule. Additional primer pairs, e.g., up to and including the FX and RX primers depicted in FIG. 2, can likewise be used to target additional regions of the nucleic acid molecule. The sequence of each of the primers can be determined based on a reference sequence, at least a portion of which may be present on or complementary to the nucleic acid molecule. For example, the F1 and R1 primers can be designed to correspond to, e.g., be complementary to, the sequence of the first region as it appears in the reference sequence. The F2 and R2 primers can be designed to correspond to, e.g., be complementary to, the sequence of the second region as it appears in the reference sequence. The F3 and R3 primers can be designed to correspond to, e.g., be complementary to, the sequence of the third region as it appears in the reference sequence.

As shown in the illustration of FIG. 2, the second forward primer (F2) is downstream from the first reverse primer (R1). In this way, the second region targeted by the second forward (F2) and reverse (R2) primers is separate from, and does not overlap with, the first region targeted by the first forward (F1) and reverse (R1) primers. In the example illustrated by FIG. 2, the third region targeted by the third forward (F3) and reverse (R3) primers is separate from, does not overlap with, and is downstream of, the first region and the second region. Accordingly, the third forward primer (F3) of this example configuration is downstream from the second reverse primer (R2). The three or more different primer pairs can be designed or configured such that the region, i.e., the last region, targeted by the FX and RX primers is located a specified number of bases from the first region in the reference sequence. For example, the specified number of bases between the first region and the last region can be less than about 5 kilobases, e.g., less than about 3000 bp, less than about 2000 bp, less than about 1500 bp, less than about 1000 bp, less than about 800 bp, less than about 600 bp, less than about 500 bp, less than about 400 bp, less than about 300 bp, less than about 250 bp, or less than about 200 bp. In terms of lower limits, the specified number of bases between the first region and the last region can be, for example, greater than about 150 bp, e.g., greater than about 200 bp, greater than about 250 bp, greater than about 300 bp, greater than about 400 bp, greater than about 500 bp, greater than about 600 bp, greater than about 800 bp, greater than about 1000 bp, greater than about 1500 bp, greater than about 2000 bp, or greater than about 3000 bp.

The selection of the specified distances between each of the three or more regions targeted by the three or more primer sets of the digital amplification reactions can determine what two or more different sizes of nucleic acid molecules can be measured using the provided method. For example, FIG. 1A illustrates a compartmentalized amplification reaction in which the nucleic acid molecule, i.e., template DNA, is a relatively long nucleic acid molecule spanning the entirety of all targeted regions and the specified distances between each adjacent pair of these regions. Accordingly, the amplification reaction of this compartment will produce PCR products corresponding to all regions targeted for amplification, and the compartment will be identified as including a nucleic acid molecule that is at least the specified number of bases in length between the first and last regions, and that covers all targeted regions. In this way, the specified distance between the first and last regions relates to one length of nucleic acid molecules that can be measured.

FIG. 1B illustrates another compartmentalized amplification reaction containing a nucleic acid molecule, i.e., template DNA, that is a relatively short nucleic acid molecule spanning the entire targeted first, second, and third regions but lacking the other targeted regions, including the last region. The amplification reaction of this compartment will produce PCR products corresponding to the first, second, and third regions, but not to any other region. The compartment will therefore be identified as including a nucleic acid molecule that is has a length sufficient to cover the first, second, and third targeted regions, and to also include the specified distances between the first and second regions and between the second and third regions, but insufficient to also cover a fourth targeted region.

Nucleic acid molecules which are shorter than the size spanning the outermost primer pairs will thus produce only a subset of the potential amplicons in a multiplexed digital amplification reaction, suggesting the presence of shorter template molecules. For example, in the case where X of FIG. 2 is five, then five different regions of the nucleic acid molecule will be targeted by first (F1/R1), second (F2/R2), third (F3/R3), fourth (F4/R4), and fifth (F5/R5) primer sets of the digital amplification reactions. Depending on the length of the template nucleic acid molecule present in a compartmentalized reaction, and the targeted regions present on that molecule, the amplification reaction in the compartment will produce amplification products targeted by F1/R1; by F2/R2; by F3/R3; by F4/R4; by F5/R5; by F1/R1 and F2/R2; by F2/R2 and F3/R3; by F3/R3 and F4/R4; by F4/R4 and F5/R5; by F1/R1, F2/R2, and F3/R3; by F2/R2, F3/R3, and F4/R4; by F3/R3, F4/R4, and F5/R5; by F1/R1, F2/R2, F3/R3, and F4/R4; by F2/R2, F3/R3, F4/R4, and F5/R5; or by F1/R1, F2/R2, F3/R3, F4/R4, and F5/R5, depending on the length of the fragment. In some embodiments, the measuring of the size of nucleic acid molecules as illustrated by FIG. 2 includes determining which of the plurality of multiplexed digital amplification reactions includes each of these subsets of potential amplicons. With knowledge of the length of each targeted region, and the specified distances between each adjacent region, the length of the template nucleic acid molecule in each of the plurality of multiplexed digital amplification reactions can then be estimated or determined.

Each of the three or more primer sets of the multiplexed digital amplification reactions can be designed or configured to target amplicons that are relatively short in length. The use of short amplicons in the provided analytical method can in at least some instances beneficially increase the accuracy and efficiency of the method, because PCR reactions are generally more effective in amplifying shorter regions than larger regions. The provided methods can therefore advantageously improve the accuracy and efficiency of using amplifications to measure the size of relatively long nucleic acid molecules, because the methods require amplification of multiple relatively short regions of the molecules, rather than a single larger region representative of the overall length of the relatively long molecule. Each region targeted for amplification can independently have a length that is, for example, less than about 1000 bp, e.g., less than about 900 bp, less than about 800 bp, less than about 700 bp, less than about 600 bp, less than about 500 bp, less than about 400 bp, less than about 300, bp, less than about 250 bp, less than about 200 bp, less than about 150 bp, less than about 100 bp, or less than about 70 bp. In terms of lower limits, each region targeted for amplification can independently have a length that is, for example, greater than about 50 bp, e.g., greater than about 70 bp, greater than about 100 bp, greater than about 150 bp, greater than about 200 bp, greater than about 250 bp, greater than about 300 bp, greater than about 400 bp, greater than about 500 bp, greater than about 600 bp, greater than about 700 bp, greater than about 800 bp, or greater than about 900 bp.

As also shown in FIG. 2, each amplification reaction of the multiplexed digital assay can also include a separate probe or reporter corresponding to each region targeted for amplification by the forward and reverse primers of each primer set. The probe of each primer set produces a detectable signal that is distinguishable from a different detectable signal produced by the probes of each other primer set. In this way, a signal from one probe of the amplification reaction can be quantifiably detected simultaneously with the quantifiable detection any one or more other signals from one or more other probes of the reaction. The signal strengths emitted from the probes in a compartmentalized reaction are generally proportionate to the amount of amplification products produced in that reaction. For example, flowing the amplification reaction illustrated in the upper portion of FIG. 2, PCR amplification products associated with each pair of forward and revers primers are present. As a result, signals from Probe 1, Probe 2, Probe 3, and all other probes up to and including Probe X can be detected from this compartmentalized reaction. Following the amplification reaction illustrated in the lower portion of FIG. 2, only PCR amplification products associated with the F1/R1, F2/R2, and F3/R3 primers are present. As a result, only the signals from Probe 1, Probe 2, and Probe 3 can be detected from this compartmentalized reaction. In some embodiments, the different probes each independently include a different fluorescent reporter. In some embodiments, the different probe signals each independently include a fluorescence emission light having a different wavelength.

In some embodiments, the measuring of the size of nucleic acid molecules as illustrated in FIG. 2 includes determining which of the plurality of multiplexed digital amplification reactions includes detectable signals from various subsets of the probes present in the reaction. For example, in the case where X of FIG. 2 is five, after completing the amplification reactions, the number of compartments, e.g., droplets, emitting signals associated with the following combinations of probes can be counted: Probe 1; Probe 2; Probe 3; Probe 4; Probe 5; Probe 1 and Probe 2; Probe 2 and Probe 3; Probe 3 and Probe 4; Probe 4 and Probe 5; Probe 1, Probe 2, and Probe 3; Probe 2, Probe 3, and Probe 4; Probe 3, Probe 4, and Probe 5; Probe 1, Probe 2, Probe 3, and Probe 4; Probe 2, Probe 3, Probe 4, and Probe 5; and Probe 1, Probe 2, Probe 3, Probe 4, and Probe 5. In some embodiments, the count of compartments emitting one combination of signals is related to the count of compartments emitting another combination of signals, or to the count of compartments emitting all other combinations of signals. For example, the different counts can be used to calculate various ratios of template nucleic acid molecules of different lengths among the compartmentalized reactions. These ratios, or other derived parameters, can be used to determine, for example, the relative size distribution of nucleic acid molecules in the original sample that comprised the molecules.

Method Using Two or More Primer Sets

Figure 3:
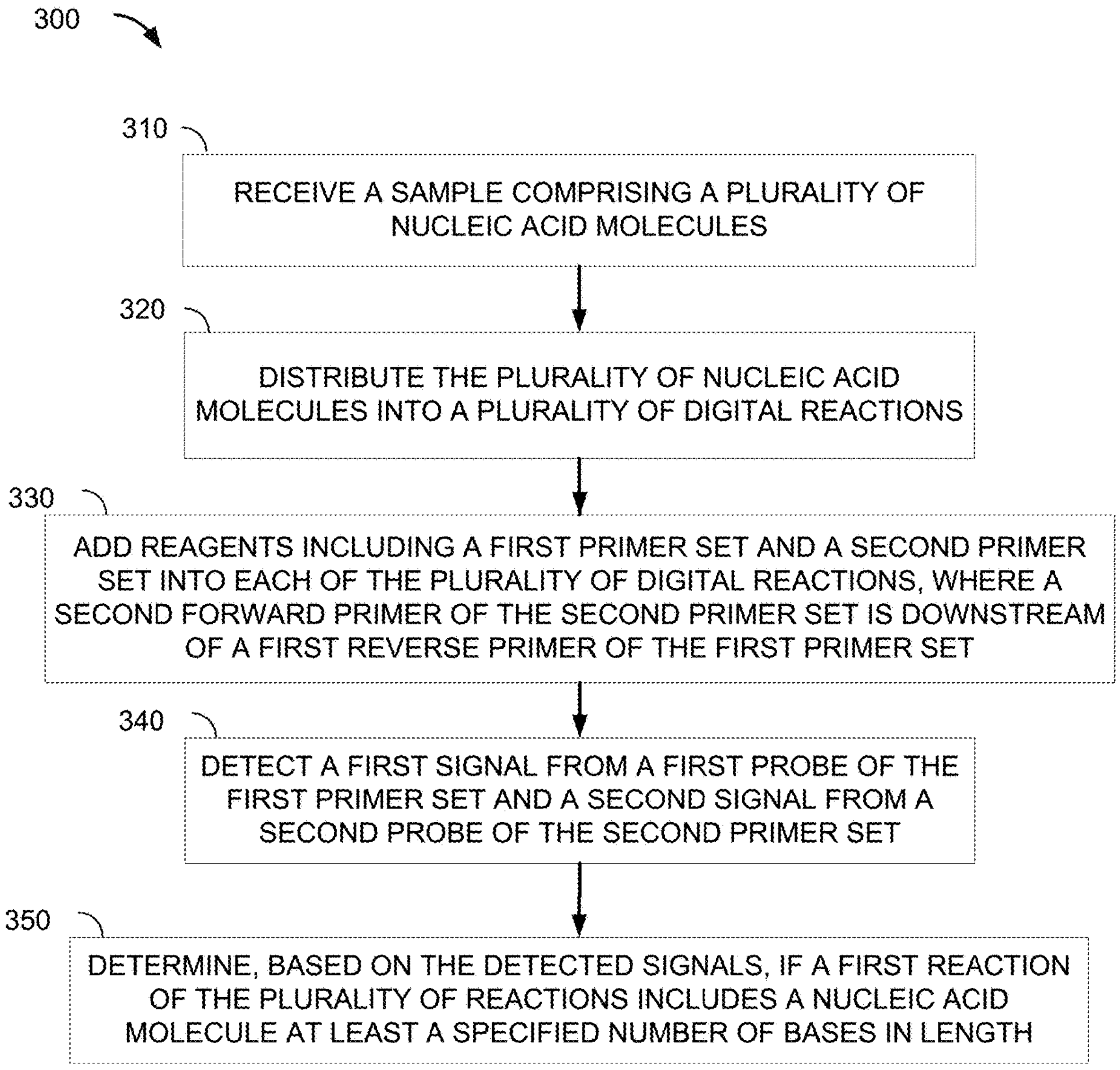
FIG. 3 presents a flowchart of a method for determining nucleic acid fragment sizes using digital amplification reactions with separate primers in accordance with a provided embodiment.

FIG. 3 presents a flowchart of a method 300 for analyzing a biological sample from a subject to measure the size of nucleic acid molecules in the sample using separate primer sets according to embodiments of the present disclosure. Various examples of method 300 are described above. Method 300 can be performed partially or entirely using a computer system.

At block 310, a sample comprising a plurality of nucleic acid molecules is received. In some embodiments, the sample is a biological sample taken from a subject. In some embodiments, the plurality of nucleic acid molecules includes or consists of a plurality of DNA molecules. In some embodiments, the plurality of nucleic acid molecules includes or consists of a plurality of RNA molecules. In some embodiments, the plurality of nucleic acid molecules includes or consists of a plurality of cell-free nucleic molecules, e.g., a plurality of cell-free DNA molecules.

In some embodiments, the plurality of nucleic acid molecules consists of between about 100 nucleic acid molecules and about 500,000 nucleic acid molecules, e.g., between about 100 nucleic acid molecules and about 17,000 nucleic acid molecules, between about 230 nucleic acid molecules and about 39,000 nucleic acid molecules, between about 550 nucleic acid molecules and about 91,000 nucleic acid molecules, between about 1300 nucleic acid molecules and about 210,000 nucleic acid molecules, or between 3000 nucleic acid molecules and about 500,000 nucleic acid molecules. In terms of upper limits, the plurality of nucleic acid molecules can consist of, for example, less than about 500,000 nucleic acid molecules, e.g., less than about 210,000 nucleic acid molecules, less than about 91,000 nucleic acid molecules, less than about 39,000 nucleic acid molecules, less than about 17,000 nucleic acid molecules, less than about 7000 nucleic acid molecules, less than about 3000 nucleic acid molecules, less than about 1300 nucleic acid molecules, less than about 550 nucleic acid molecules, or less than about 230 nucleic acid molecules. In terms of lower limits, the plurality of nucleic acid molecules can consist of, for example, greater than about 100 nucleic acid molecules, e.g., greater than about 230 nucleic acid molecules, greater than about 550 nucleic acid molecules, greater than about 1300 nucleic acid molecules, greater than about 3000 nucleic acid molecules, greater than about 7000 nucleic acid molecules, greater than about 17,000 nucleic acid molecules, greater than about 39,000 nucleic acid molecules, greater than about 91,000 nucleic acid molecules, or greater than about 210,000 nucleic acid molecules. Larger numbers of nucleic acid molecules, e.g., greater than 500,000 nucleic acid molecules, and smaller numbers of nucleic acid molecules, e.g., less than 100 nucleic acid molecules, are also contemplated.

At block 320, the plurality of nucleic acid molecules is distributed into a plurality of digital reactions. The digital reactions can be any of those disclosed herein. In some embodiments, each of the plurality of digital reactions is a digital polymerase chain reaction. In some embodiments, each of the plurality of digital reactions is a droplet digital polymerase chain reaction. In some embodiments, the distribution of the plurality of nucleic acid molecules into the plurality of digital reactions results in the plurality of digital reactions having an average of one nucleic acid molecule per digital reaction.

At block 330, reagents are added into each of the plurality of digital reactions. The reagents for each of the plurality of reactions include a first primer set targeting a first region of a reference sequence, and a second primer set targeting a second region of the reference sequence. At least a portion of the plurality of nucleic acid molecules include at least a portion of the reference sequence, or at least a portion of a sequence complementary to the reference sequence. The second region is within a specified number of bases from the first region in the reference sequence. The specified number of bases can be any of those disclosed herein. For example, in some embodiments, the specified number of bases is about 5 kilobases or less. In some embodiments, the specified number of bases is about 500 bases or more.

The first primer set includes a first forward primer, a first reverse primer, and a first probe. The second primer set includes a second forward primer, a second reverse primer, and a second probe. The second forward primer and the second reverse primer are each downstream from the first reverse primer in the reference sequence. The first region and the second region can each independently have any of the sizes disclosed herein. For example, in some embodiments, the first region and the second region each independently have a length that is less than about 500 bp.

The first probe and the second probe can be any of those disclosed herein. In some embodiments, the first probe and the second probe each independently comprise a fluorescent label. In some embodiments, the reagents for each of the plurality of digital reactions further include a reverse transcriptase enzyme.

In some embodiments, the reagents for each of the plurality of reactions further include a third primer set targeting a third region of the reference sequence. The third primer set includes a third forward primer, a third reverse primer, and a third probe. In some embodiments, the third region is located between the first region and the second region in the reference sequence, such that the third forward primer and the third reverse primer are each downstream from the first reverse primer in the reference sequence, and the third forward primer and the third reverse primer are each upstream from the second forward primer in the reference sequence.

At block 340, a first signal from the first probe is detected for a first digital reaction of the plurality of digital reactions, and a second signal from the second probe is also detected for the first digital reaction. In some embodiments, method 300 further includes an operation of detecting a third signal from the third probe, when present, in the first digital reaction. The signals can be any of those disclosed herein. In some embodiments, the signals each independently comprise a fluorescence emission light having a different wavelength from that of the other signals.

At block 350, based on the detecting of the first signal and the second signal in block 340, the first reaction is determined to include a nucleic acid molecule of the plurality of nucleic acid molecules that is at least the specified number of bases in length and that covers the first region and the second region.

In some embodiments, method 300 includes an operation of detecting a first number of the plurality of digital reactions that are positive for only one of the first signal and the second signal. This first number represents the count of digital reactions containing a nucleic acid molecule, e.g., a relatively short nucleic acid molecule, that includes only one of the first targeted region and the second targeted region. In some embodiments, method 300 includes an operation of detecting a second number of the plurality of digital reactions that are positive for both of the first signal and the second signal. This second number represents the count of digital reactions containing a nucleic acid molecule, e.g., a relatively long nucleic acid molecule, that includes both the first targeted region and the second targeted region.

Method 300 can include determining a parameter using the first number and the second number, where the parameter measures a relative amount between the first number and the second number. The parameter can be a separation value between the first number and the second number. As one example, determining the parameter can comprise dividing the first number by the second number or by a sum of the first number and the second number. As another example, determining the parameter can comprise dividing the second number by the first number or by a sum of the first number and the second number. As another example, determining the parameter can comprise subtracting the first number from the second number, and optionally dividing the subtraction result by the first number, by the second number, or by a sum of the first number and the second number. As another example, determining the parameter can comprise subtracting the second number from the first number, and optionally dividing the subtraction result by the first number, by the second number, or by a sum of the first number and the second number.

Method 300 can also include a step for detecting combinations of signals indicating that the template nucleic acid molecule of a reaction is long enough to include one of two outer regions targeted for amplification, as well as a region between the two outer regions, but not long enough to include all three of these regions. For example, method 300 can include a step for detecting a third number of the plurality of digital reactions that are positive for the third signal from the third probe, when present in the digital reactions, and that also are positive for only one of the first signal and the second signal. This third number represents the count of digital reactions containing a nucleic acid molecule that includes either the first region and the adjacent third region, or the second region and the adjacent third region.

When method 300 includes a step of detecting this third number of digital reactions, method 300 can further include an operation of determining a second parameter using the first number and the third number, where the parameter measures a relative amount between the first number and the third number. The second parameter can be a separation value between the first number and the third number. As one example, determining the second parameter can comprise dividing the first number by the third number. As another example, determining the second parameter can comprise dividing the third number by the first number or by a sum of the first number and the second number. As another example, determining the second parameter can comprise subtracting the first number from the third number, and optionally dividing the subtraction result by the first number, by the third number, or by a sum of the first number and the third number. As another example, determining the second parameter can comprise subtracting the third number from the first number, and optionally dividing the subtraction result by the first number, by the third number, or by a sum of the first number and the third number.

Alternatively, when method 300 includes a step of detecting the third number of digital reactions, method 300 can include an operation of determining a second parameter using the second number and the third number, where the second parameter measures a relative amount between the second number and the third number. The second parameter can be a separation value between the second number and the third number. As an example, determining the second parameter can comprise dividing the second number by the third number. As another example, determining the second parameter can comprise dividing the third number by the second number or by a sum of the first number and the second number. As another example, determining the second parameter can comprise subtracting the second number from the third number, and optionally dividing the subtraction result by the second number, by the third number, or by a sum of the second number and the third number. As another example, determining the second parameter can comprise subtracting the third number from the second number, and optionally dividing the subtraction result by the second number, by the third number, or by a sum of the second number and the third number.

Method 300 can also include an operation of determining a size distribution of the plurality of nucleic acid molecules in the sample. The size distribution can be determined, for example, using the first parameter and the second parameter.

III. Measuring Size Using Shared Primers

In other aspects, the present disclosure provides methods for measuring the sizes of nucleic acid molecules, e.g., a plurality of cell-free nucleic acid molecules from a biological sample, by amplifying two or more overlapping regions of a reference sequence, at least a portion of which is present in or complementary to the nucleic acid molecules. Positive amplification of more than one of these targeted overlapping regions from a nucleic acid molecule indicates that the nucleic acid molecule has a sequence length at least long enough to cover or include each of the successfully amplified regions. Positive amplification of fewer targeted overlapping regions, e.g., only one targeted region, indicates that the nucleic acid molecule instead has a length insufficiently long enough to fully cover or include each region targeted for amplification. For each region targeted for amplification, the multiplexed amplification reactions include a different and distinctly observable probe, e.g., a fluorescent probe, and pair of amplification primers, e.g., a forward and a reverse PCR primer, one of which is commonly shared among the targeted regions. These provided methods preferably involve multiplexed digital PCR and in certain aspects are particularly advantageous for measuring the size of relatively long nucleic acid molecules, without needing to rely on the frequently inefficient amplification of relatively long amplicons.

A. Schematic for Using Shared Primers

Figure 4A:
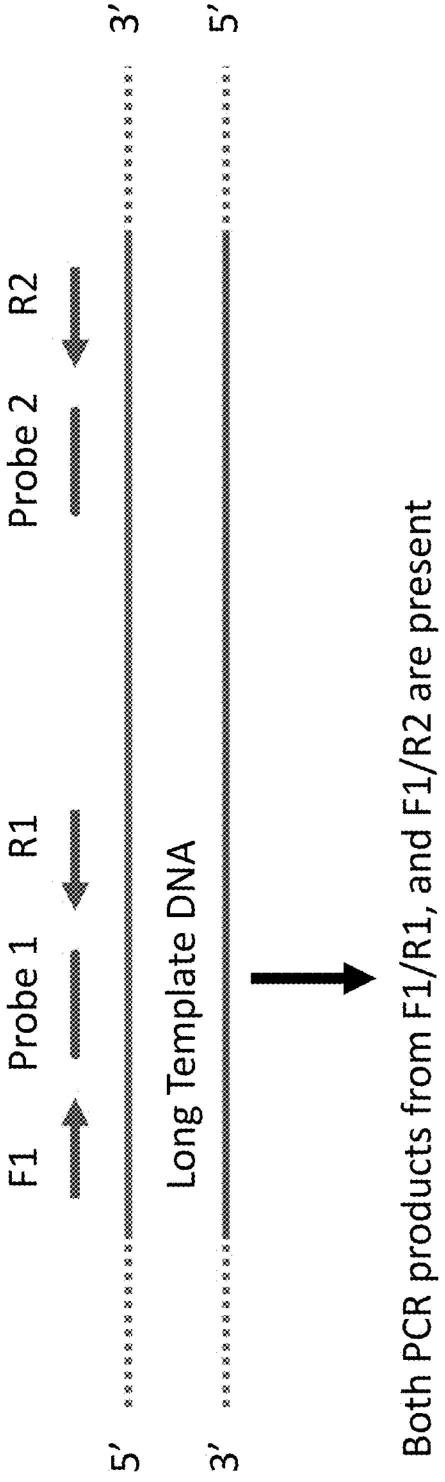
FIG. 4A presents a schematic illustration of an exemplary digital assay with shared primers for deducing the size of a relatively long template nucleic acid molecule in accordance with a provided embodiment.
Figure 4B:
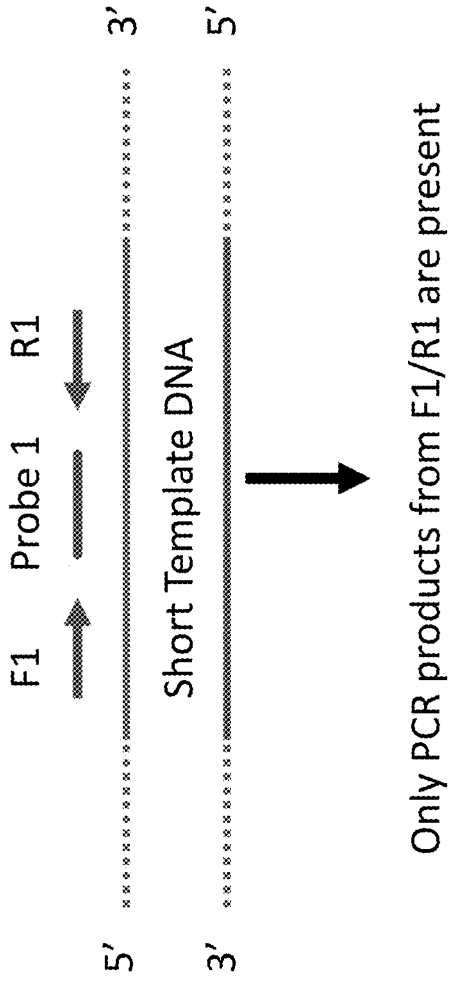
FIG. 4B presents a schematic illustration of an exemplary digital assay with shared primers for deducing the size of a relatively short template nucleic acid molecule in accordance with a provided embodiment.

FIGS. 4A and 4B provide a schematic illustration of a disclosed multiplexed digital amplification reaction for measuring the size of a nucleic acid molecule using two sets of PCR primer pairs that share one common primer. Each amplification reaction of the multiplexed digital assay includes, among other necessary enzymes, reagents, buffers, and additional components of PCR amplification, three PCR primers. Two of these three primers are a first forward (F1) and reverse (R1) primer targeting amplification of a first region of the nucleic acid molecule. The other of the three primers is a second reverse primer (R2) that, together with the first forward primer (F1), targets amplification of a second region of the nucleic acid molecule. The sequence of each of the primers can be determined based on a reference sequence, at least a portion of which may be present on or complementary to the nucleic acid molecule. For example, the F1 and R1 primers can be designed to correspond to, e.g., be complementary to, the sequence of the first region as it appears in the reference sequence. The F1 and R2 primers can likewise be designed to correspond to, e.g., be complementary to, the sequence of the second region as it appears in the reference sequence.

As shown in the illustration of FIGS. 4A and 4B, the second reverse primer (R2) is downstream from the first reverse primer (R1). In this way, and because the first primer set and the second primer set share a common forward primer (F1), the first region targeted by the first forward primer (F1) and the first reverse primer (R1) is a subset of, and thus overlaps with, the second region targeted by the first forward primer (F1) and the second reverse primer (R2). Alternatively, rather than sharing a common forward primer as illustrated in FIGS. 4A and 4B, the first primer set and the second primer set can instead share a common reverse primer. In one example of such a configuration, the second forward primer is upstream from the first forward primer. Accordingly, in this case the first region targeted by the first forward primer and a common shared reverse primer is still a subset of, and overlaps with, the second region targeted by the second forward primer and the common shared reverse primer.

The primers can be designed or configured such that the first region has a specified smaller size that can be, for example, between about 40 bp and about 100 bp, e.g., between about 40 bp and about 76 bp, between about 46 bp and about 82 bp, between about 52 bp and about 88 bp, between about 58 bp and about 94 bp, or between about 64 bp and about 100 bp. In terms of upper limits, the smaller first region can have a size that is, for example, less than about 100 bp, e.g., less than about 94 bp, less than about 88 bp, less than about 82 bp, less than about 76 bp, less than about 70 bp, less than about 64 bp, less than about 58 bp, less than about 52 bp, or less than about 46 bp. In terms of lower limits, the smaller first region can have a size that is, for example, greater than about 40 bp, e.g., greater than about 46 bp, greater than about 52 bp, greater than about 58 bp, greater than about 64 bp, greater than about 70 bp, greater than about 76 bp, greater than about 82 bp, greater than about 88 bp, or greater than about 94 bp. Larger short region sizes, e.g., greater than 100 bp, and smaller short region sizes, e.g., less than about 40 bp, are also contemplated.

The primers can be designed or configured such that the second region has a specified larger size that can be, for example, between about 100 bp and about 1000 bp, e.g., between about 100 bp and about 640 bp, between about 190 bp and about 730 bp, between about 280 bp and about 820 bp, between about 370 bp and about 910 bp, or between about 460 bp and about 1000 bp. The larger second region can have a size that is, for example, between about 100 bp and about 250 bp, e.g., between about 100 bp and about 190 bp, between about 115 bp and about 205 bp, between about 130 bp and about 220 bp, between about 145 bp and about 235 bp, or between about 160 bp and about 250 bp. In terms of upper limits, the larger second region can have a size that is, for example, less than about 1000 bp, e.g., less than about 910 bp, less than about 820 bp, less than about 730 bp, less than about 640 bp, less than about 550 bp, less than about 460 bp, less than about 370 bp, less than about 280 bp, less than about 250 bp, less than about 235 bp, less than about 220 bp, less than about 205 bp, less than about 190 bp, less than about 175 bp, less than about 160 bp, less than about 145 bp, less than about 130 bp, or less than about 115 bp. In terms of lower limits, the larger second region can have a size that is, for example, greater than about 100 bp, e.g., greater than about 115 bp, greater than about 130 bp, greater than about 145 bp, greater than about 160 bp, greater than about 175 bp, greater than about 190 bp, greater than about 205 bp, greater than about 220 bp, greater than about 235 bp, greater than about 250 bp, greater than about 280 bp, greater than about 370 bp, greater than about 460 bp, greater than about 550 bp, greater than about 640 bp, greater than about 730 bp, greater than about 820 bp, or greater than about 910 bp. Larger long region sizes, e.g., greater than about 1000 bp, and smaller long region sizes, e.g., less than about 100 bp, are also contemplated.

The selection of the specified sizes of the smaller targeted first region and the larger targeted second region can determine what sizes of nucleic acid molecules can be measured with the provided method. For example, FIG. 4A illustrates a compartmentalized amplification reaction in which the nucleic acid molecule, i.e., template DNA, is a relatively long nucleic acid molecule spanning the entire targeted first and second regions. Accordingly, the amplification reaction of this compartment will produce PCR products corresponding to both the first and the second regions, and the compartment will be identified as including a nucleic acid molecule that is at least as long as the second region targeted by the second (F1/R2) primer set. In this way, the specified length of the longer second region relates to one length of nucleic acid molecules that can be measured with the method.

FIG. 4B illustrates another compartmentalized amplification reaction containing a nucleic acid molecule, i.e., template DNA, that is a relatively short nucleic acid molecule spanning the entire first targeted region but lacking the binding site for the unique primer of the second targeted region. The amplification reaction of this compartment will produce PCR products corresponding to the first region, but not to the second region. The compartment will therefore be identified as including a nucleic acid molecule that is at least as long as the first region targeted by the first (F1/R1) primer set but may not as long as the second region targeted by the second (F1/R2) primer set. In this way, the specified length of the shorter first region relates to another length of nucleic acid molecules that can be measured with the method.

As also shown in FIGS. 4A and 4B, each amplification reaction of the multiplexed digital assay also includes a first probe or reporter (Probe 1) and a second probe or reporter (Probe 2). The first probe corresponds to the first region targeted for amplification by the first forward (F1) and first reverse (R1) primers of the first primer set. The second probe corresponds to the second region targeted for amplification by the first forward (F1) and second reverse (R2) primers of the second primer set. For example, the second probe can recognize a portion of the second region that is not within the first region. The first probe of the first primer set produces a detectable signal that is distinguishable from a different detectable signal produced by the second probe of the second primer set. In this way, a first signal from the first probe can be quantifiably detected simultaneously with the quantifiable detection of a second signal from the second probe.

The signal strengths emitted from the probes in a compartmentalized reaction are generally proportionate to the amount of amplification products produced in that reaction. For example, flowing the amplification reaction illustrated FIG. 4A, PCR amplification products associated with both the F1/R1 primers and the F1/R2 primers are present. As a result, signals from both Probe 1 and Probe 2 can be detected from this compartmentalized reaction. Following the amplification reaction illustrated in FIG. 4B, only PCR amplification products associated with the F1/R1 primers are present. As a result, only the signal from Probe 1 can be detected from this compartmentalized reaction. In some embodiments, the first probe and the second probe each independently include a different fluorescent reporter. In some embodiments, the first signal and the second signal each independently include a fluorescence emission light having a different wavelength.

In some embodiments, the measuring of the size of nucleic acid molecules as illustrated in FIGS. 4A and 4B includes determining which of the plurality of multiplexed digital amplification reactions includes a nucleic acid molecule sufficiently long enough to include the entire first region and the entire second region. For example, after completing the amplification reactions, the number of compartments, e.g., droplets, emitting the first signal from the first probe and the second signal from the second probe can be counted. In some embodiments, the measuring of the size of nucleic acid molecules as illustrated in FIGS. 4A and 4B further includes determining which of the plurality of multiplexed digital amplification reactions included a nucleic acid molecule only long enough to include the first region. For example, after completing the amplification reactions, the number of compartments, e.g., droplets, emitting only the first signal from the first probe can be counted. In some embodiments, the count of compartments emitting both the first and second signals is related to the count of compartments emitting only the first signal. For example, the two different counts can be used to calculate a ratio of long template DNA to short template DNA among the compartmentalized reactions, or a ratio of short template DNA to long template DNA among the reactions. These ratios, or other derived parameters, can be used to determine, for example, the relative size distribution of nucleic acid molecules in the original sample that comprised the molecules.

Figure 5:
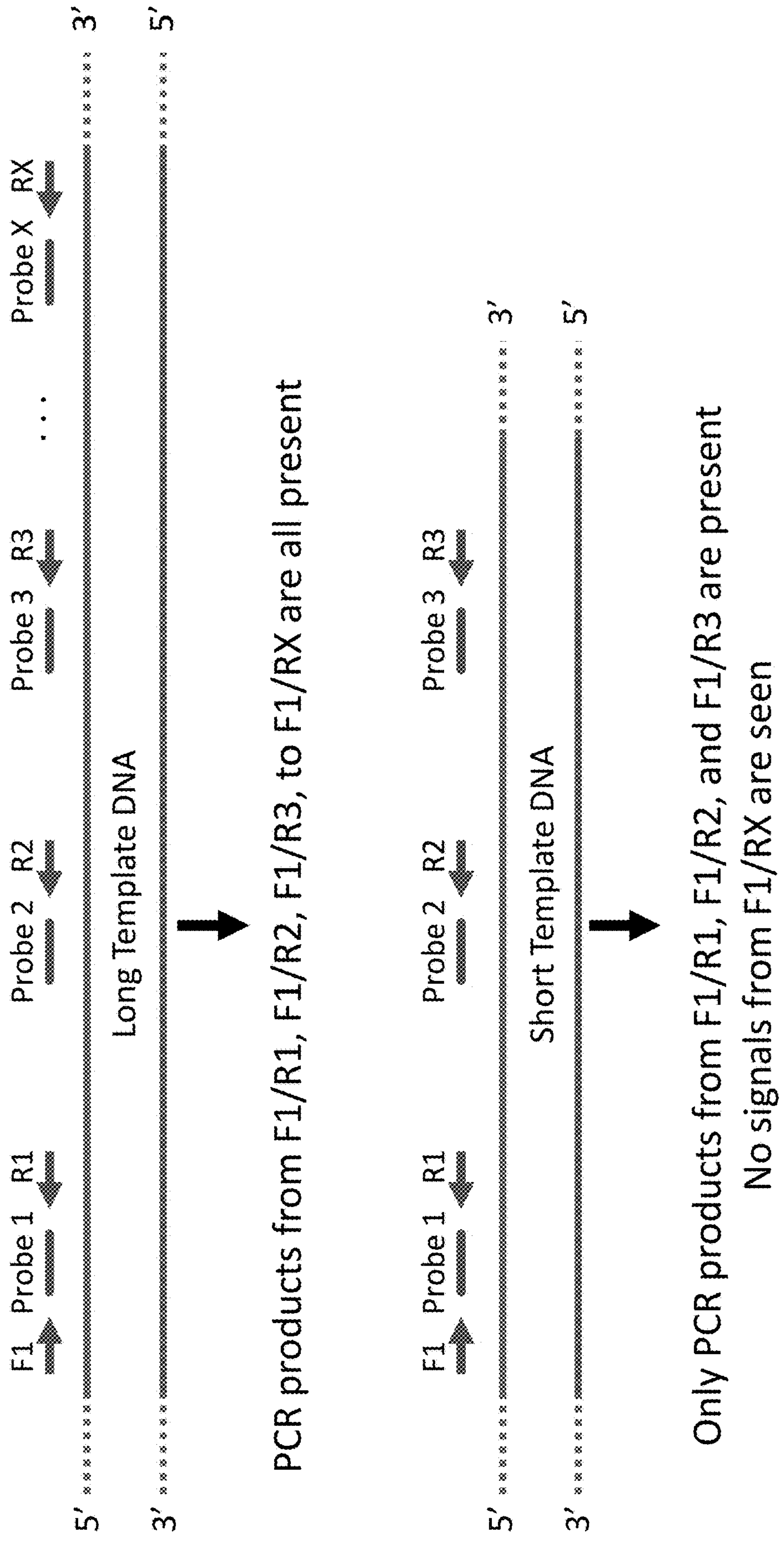
FIG. 5 presents a schematic illustration of an exemplary digital assay with shared primers for deducing multiple sizes of nucleic acids in accordance with a provided embodiment.

As illustrated in FIG. 5, in other configurations of this method useful for measuring more different sizes of nucleic acid molecules, three or more sets of primers can be used, where each set shares the same common primer. In some embodiments, and as shown in FIG. 5, each primer set shares a common forward primer, and multiple reverse primers (e.g., R1, R2, R3, . . . . RX) are used to target X different regions, where the first region is a subset of the second region, the second region is a subset of the third region, and so forth. In some embodiments, each primer set shares a common reverse primer, and multiple forward primers (e.g., F1, F2, F3, . . . . FX) are used to target X different regions, where the first region is a subset of the second region, the second region is a subset of the third region, and so forth.

In such embodiments, nucleic acid molecules which are shorter than the size spanning the outermost primer pair (e.g., F1/RX or FX/R1) will thus produce only a subset of the potential amplicons in a multiplexed digital amplification reaction, suggesting the presence of shorter template molecules. For example, in the case where X is five and the primer sets share a common forward primer, then five different regions of the nucleic acid molecule will be targeted by first (F1/R1), second (F1/R2), third (F1/R3), fourth (F1/R4), and fifth (F1/R5) primer sets of the digital amplification reactions. Depending on the length of the template nucleic acid molecule present in a compartmentalized reaction, and the targeted regions present on that molecule, the amplification reaction in the compartment will produce amplification products targeted by F1/R1; by F1/R1 and F1/R2; by F1/R1, F1/R2, and F1/R3; by F1/R1, F1/R2, F1/R3, and F1/R4; or by F1/R1, F1/R2, F1/R3, F4/R4, and F5/R5. In some embodiments, the measuring of the size of nucleic acid molecules includes determining which of the plurality of multiplexed digital amplification reactions includes each of these subsets of potential amplicons. With knowledge of the length of each targeted region, the length of the template nucleic acid molecule in each of the plurality of multiplexed digital amplification reactions can then be estimated or determined.

B. Method

Figure 6:
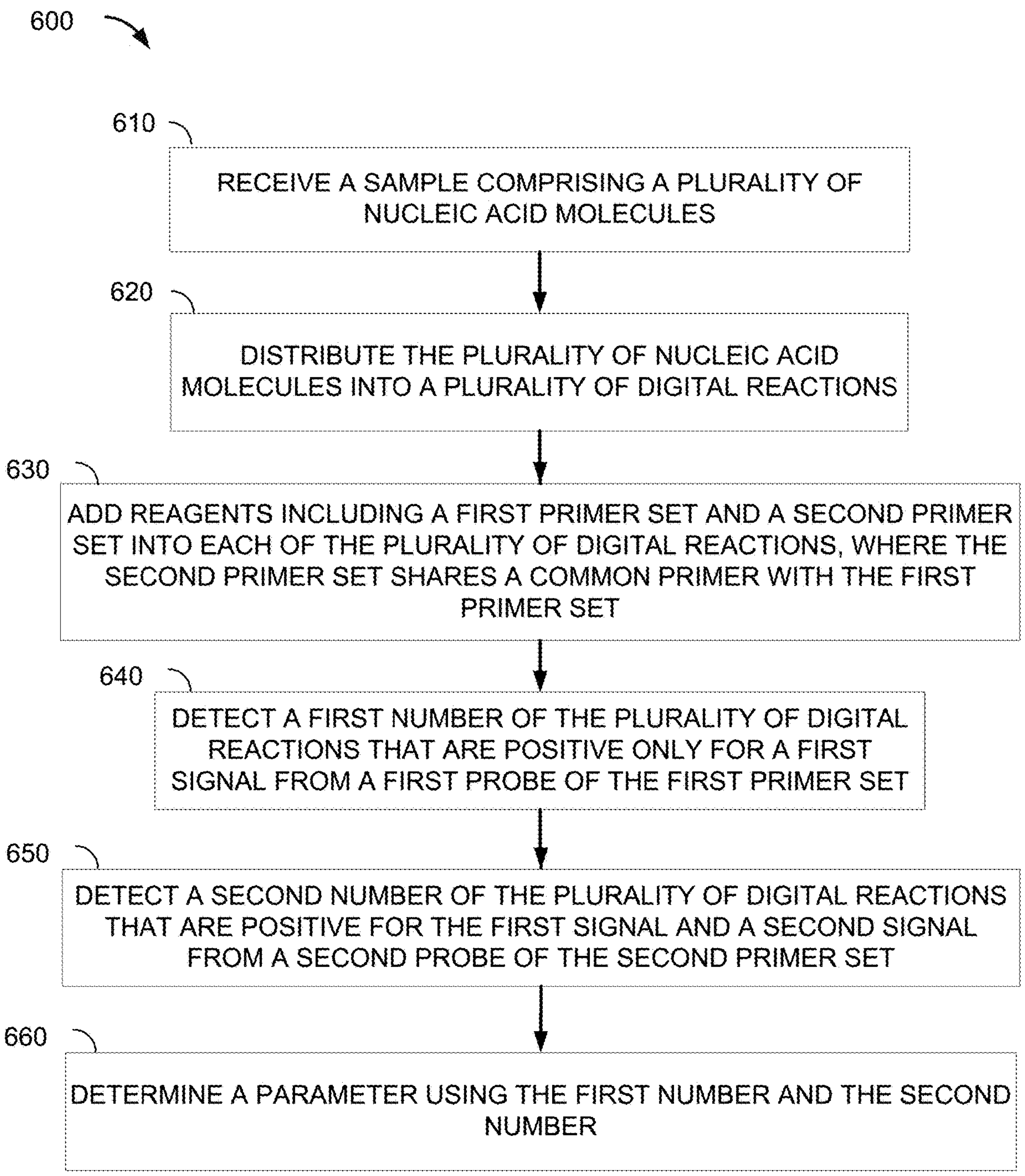
FIG. 6 presents a flowchart of a method for determining nucleic acid fragment sizes using digital amplification reactions with shared primers in accordance with a provided embodiment.

FIG. 6 presents a flowchart of a method 600 for analyzing a biological sample from a subject to measure the size of nucleic acid molecules in the sample using shared primers according to embodiments of the present disclosure. Various examples of method 600 are described above. Method 600 can be performed partially or entirely using a computer system.

At block 610, a sample comprising a plurality of nucleic acid molecules is received. Block 610 can be performed in a similar manner to block 310. As with block 310, in some embodiments, the sample is a biological sample taken from a subject. In some embodiments, the plurality of nucleic acid molecules includes or consists of a plurality of DNA molecules. In some embodiments, the plurality of nucleic acid molecules includes or consists of a plurality of RNA molecules. In some embodiments, the plurality of nucleic acid molecules includes or consists of a plurality of cell-free nucleic acid molecules, e.g., a plurality of cell-free DNA molecules. As with block 310, in some embodiments, the plurality of nucleic acid molecules consists of between about 100 nucleic acid molecules and about 500,000 nucleic acid molecules, e.g., any of the numbers of nucleic acid molecules described in relation to block 310.

At block 620, the plurality of nucleic acid molecules is distributed into a plurality of digital reactions. Block 620 can be performed in a similar manner to block 320. As with block 320, in some embodiments, each of the plurality of digital reactions is a digital polymerase chain reaction. In some embodiments, each of the plurality of digital reactions is a droplet digital polymerase chain reaction. In some embodiments, the distribution of the plurality of nucleic acid molecules into the plurality of digital reactions results in the plurality of digital reactions having an average of one nucleic acid molecule per digital reaction.

At block 630, reagents are added into each of the plurality of digital reactions. The reagents for each of the plurality of reactions include a first primer set targeting a first region of a reference sequence, and a second primer set targeting a second region of the reference sequence. At least a portion of the plurality of nucleic acid molecules include at least a portion of the reference sequence, or at least a portion of a sequence complementary to the reference sequence. The second region is larger than the first region and includes the first region. The first primer set includes a first forward primer, a first reverse primer, and a first probe. The second primer set includes a second probe and a second primer that is either a second forward primer or a second reverse primer. The second primer set shares a common primer with the first primer set. For example, if the second primer set includes a second forward primer, then the second primer set shares the first reverse primer of the first primer set as a common primer with the first primer set. Alternatively, if the second primer set includes a second reverse primer, then the second primer set shares the first forward primer of the first primer set as a common primer with the first primer set. The shorter first region targeted by the first primer set can have any of the shorter first region sizes disclosed herein. For example, in some embodiments, the shorter first region has a length that is between about 40 bp and about 100 bp. The longer second region targeted by the second primer set can have any of the larger second region sizes disclosed herein. For example, in some embodiments, the longer second region has a length that is between about 100 bp and about 1000 bp.

In some embodiments, the longer second region has a length that is between about 100 bp and about 250 bp.

The first probe and the second probe of block 630 can be any of those disclosed herein and can be similar to the first probe and the second probe described in relation to block 330. As with block 330, in some embodiments, the first probe and the second probe each independently comprise a fluorescent label. As with block 330, in some embodiments, the reagents of block 630 further include a reverse transcriptase enzyme.

In some embodiments, the reagents of block 630 further include a third primer set targeting a third region of the reference sequence. The third region is larger than the first region and includes the first region. Additionally, the second region is larger than the third region and includes the third region. Accordingly, the first region is a subregion of the third region, which is itself a subregion of the second region. The third primer set includes a third probe and a third primer that is either a third forward primer or a third reverse primer. The third primer shares the common primer with the first primer set and the second primer set. For example, if the second primer set includes a second forward primer, then the third primer set includes a third forward primer and the third primer set shares the first reverse primer of the first primer set as a common primer with the first primer set and the second primer set. Alternatively, if the second primer set includes a second reverse primer, then the third primer set includes a third reverse primer and shares the first forward primer of the first primer set as a common primer with the first primer set and the second primer set.

At block 640, a first number of the plurality of digital reactions that are positive for only a first signal from the first probe is detected. The first signal can be any of those disclosed herein. In some embodiments, the first signal comprises a fluorescence emission light, e.g., a fluorescence emission light having a different wavelength than that of fluorescence emission lights of the second signal and the third signal, when present. The first number represents the count of digital reactions containing a nucleic acid molecule, e.g., a relatively short nucleic acid molecule, that includes the entirety of the first targeted region but that does not include the entirety of the second targeted region.

At block 650, a second number of the plurality of digital reactions that are positive for both the first signal and a second signal is detected. The second signal is from the second probe. The second signal can be any of those disclosed herein. In some embodiments, the second signal comprises a fluorescence emission light, e.g., a fluorescence emission light having a different wavelength than that of fluorescence emission lights of the first signal and the third signal, when present. The second number represents the count of digital reactions containing a nucleic acid molecule, e.g., a relatively long nucleic acid molecule, that includes the entirety of the first targeted region and the entirety of the second targeted region.

Method 600 can also include a step for detecting combinations of signals indicating that the template nucleic acid molecule of a reaction is long enough to include the smallest region targeted for amplification, as well as an intermediately sized overlapping targeted region that includes the smallest region, but not long enough to include the largest targeted region which overlaps with and includes both the smallest region and the intermediately sized region. For example, method 600 can include a step for detecting a third number of the plurality of reactions that are not positive for the second signal and that are positive for both the first signal and a third signal. The third signal is from the third probe. The third signal can be any of those disclosed herein. In some embodiments, the third signal comprises a fluorescence emission light, e.g., a fluorescence emission light having a different wavelength than that of fluorescence emission lights of the first signal and the second signal. The third number represents the count of digital reactions containing a nucleic acid molecule that includes the entirety of the first targeted region and the entirety of the third targeted region but that does not include the entirety of the second targeted region.

At block 660, a parameter is determined using the first number and the second number. In some embodiments, the parameter measures a relative amount between the first number and the second number. In some embodiments, the parameter is a separation value between the first number and the second number. As one example, determining the parameter can comprise dividing the first number by the second number or by a sum of the first number and the second number. As another example, determining the parameter can comprise dividing the second number by the first number or by a sum of the first number and the second number. As another example, determining the parameter can comprise subtracting the first number from the second number, and optionally dividing the subtraction result by the first number, by the second number, or by a sum of the first number and the second number. As another example, determining the parameter comprises subtracting the second number from the first number, and optionally dividing the subtraction result by the first number, by the second number, or by a sum of the first number and the second number.

When method 600 includes a step of detecting the third number of digital reactions, method 600 can further include an operation of determining a second parameter using the first number and the third number, where the parameter measures a relative amount between the first number and the third number. The second parameter can be a separation value between the first number and the third number. As an example, determining the second parameter can comprise dividing the first number by the third number. As another example, determining the second parameter can comprise dividing the third number by the first number or by a sum of the first number and the second number. As another example, determining the second parameter can comprise subtracting the first number from the third number, and optionally dividing the subtraction result by the first number, by the third number, or by a sum of the first number and the third number. As another example, determining the second parameter can comprise subtracting the third number from the first number, and optionally dividing the subtraction result by the first number, by the third number, or by a sum of the first number and the third number.

Alternatively, when method 600 includes a step of detecting the third number of digital reactions, method 600 can include an operation of determining a second parameter using the second number and the third number, where the second parameter measures a relative amount between the second number and the third number. The second parameter can be a separation value between the second number and the third number. As one example, determining the second parameter can comprise dividing the second number by the third number. As another example, determining the second parameter can comprise dividing the third number by the second number or by a sum of the first number and the second number. As another example, determining the second parameter can comprise subtracting the second number from the third number, and optionally dividing the subtraction result by the second number, by the third number, or by a sum of the second number and the third number. As another example, determining the second parameter can comprise subtracting the third number from the second number, and optionally dividing the subtraction result by the second number, by the third number, or by a sum of the second number and the third number.

Method 600 can also include an operation of determining a size distribution of the plurality of nucleic acid molecules in the sample. The size distribution can be determined, for example, using the first parameter. The size distribution can alternatively or additionally be determined using the first parameter and the second parameter.

IV. Using Nucleic Acid Molecule Size to Detect Pathology

In some aspects, the present disclosure provides methods for using the measured sizes of nucleic acid molecules, e.g., a plurality of cell-free nucleic acid molecules from a biological sample obtained from a subject, to detect or classify a pathology of the subject. For example, the particular size distribution of certain nucleic acid molecules in a sample can be indicative of the presence, absence, or level of a pathology. The provided methods can therefore be advantageously used for non-invasive investigations of the health status of a subject.

In some embodiments, the plurality of nucleic acid molecules analyzed by a provided method are obtained from a biological sample, such as a maternal plasma sample, of a pregnant mother. DNA molecules (i.e., cell-free DNA fragments) derived from the fetus and present in maternal plasma have a shorter size distribution compared with those derived from the mother (K. C. A. Chan et al., Clin. Chem. 50, (2004): 88; Y. M. D. Lo et al. Sci. Transl. Med. 2, (2010): 61ra91). Hence, the presence of an extra fetal chromosome in fetal trisomy would shorten the size distribution of DNA in maternal plasma derived from that chromosome. A size-based analytical approach can thus detect an increased proportion of short fragments from the aneuploid chromosome in the plasma. This approach allows the detection of multiple types of fetal whole-chromosome aneuploidies, including trisomies 21, 18, 13 and monosomy X, with high accuracy (S. C. Y. Yu et al., Proc. Natl. Acad. Sci. USA 111, (2014): 8583).

Because fetal DNA fragments are generally smaller than maternal DNA fragments, a difference in size can be used to detect a copy number aberration in a fetus. If a fetus has an amplification in a first chromosomal region, then the average size of maternal plasma DNA fragments for that region will be lower than for a second region that does not have an amplification. This results from the extra, smaller fetal DNA in the first region decreasing the average size. Similarly, for a deletion, the fewer fetal fragments for a region will cause the average size to be larger than for normal regions.

As another example, size analysis can be used to differentiate members of a control pregnancy group from patients suffering from preeclampsia toxemia (PET). Single molecule sequencing data results (e.g., using single-molecule real-time (SMRT) sequencing or nanopore sequencing) have demonstrated that PET patients can have a relatively higher concentration of short cell-free DNA than the control group members. Notably, this type of analysis cannot be performed using typical sequencing (e.g., using bridge amplification) because such sequencing prefers sequencing short fragments, e.g., nucleic acid molecules having a length less than 600 bp. Beneficially, the nucleic acid molecule size measurement methods provided herein do not have this drawback.

Apart from applications in noninvasive prenatal diagnosis, embodiments can also be used for measuring the fractional concentration of clinically useful nucleic acid species of different sizes in biological fluids, which can be useful for cancer detection, transplantation, and medical monitoring. Previous studies showed that tumor-derived DNA is typically shorter than the non-cancer-derived DNA in a cancer patient's plasma (F. Diehl et al., Proc. Natl. Acad. Sci. USA 102, (2005): 16368). In the transplantation context, hematopoietic-derived DNA is shorter than non-hematopoietic DNA (Y. W. Zheng et al., Clin. Chem. 58, (2012): 549). For example, if a patient receives a liver from a donor, then the DNA derived from the liver (a nonhematopoietic organ in the adult) will be shorter than hematopoietic-derived DNA in the plasma (Y. W. Zheng et al., Clin. Chem. 58, (2012): 549). Similarly, in a patient with myocardial infarction or stroke, the DNA released by the damaged nonhematopoietic organs (i.e., the heart and brain, respectively) would be expected to result in a shift in the size profile of plasma DNA towards the shorter spectrum. In these cases, it is believed that cancer-related death of cells from a particular tissue can lead to an inordinate about of small nucleic acid molecule fragments derived from that tissue.

In addition to absolute nucleic acid molecule sizes, other related statistical values can be used for detecting or classifying a pathology. These values can include, for example, a cumulative frequency for a given size or various ratios of amount of DNA fragments of different sizes. A cumulative frequency can correspond to a proportion of DNA fragments that are of a given size or smaller. The statistical values provide information about the distribution of the sizes of DNA fragments for comparison against one or more size thresholds for healthy control subjects. One skilled in the art will know how to determine such thresholds or cutoffs.

V. Guiding Assay Design

In other aspects, the present disclosure provides methods for designing assays to measure the size of nucleic acid molecules with multiplexed digital amplification reactions. The methods are particularly useful for designing assays having an improved ability to differentiate between, and/or quantify the absolute and/or relative abundance of, relatively long and short nucleic acid molecules in a sample of a plurality of nucleic acid molecules. To determine what assay parameter selections result in such an improved assay, the provided assay design methods use sequencing data from long amplicons. More specifically, the provided methods use in-silico simulations based on long-read sequencing data to predict and compare simulated results of different multiplexed digital amplification assay designs.

As an example, the provided assay design methods have been used to select parameters for a multiplexed digital amplification assay differentiating the maternal plasma DNA of mothers with healthy pregnancies from the maternal plasma DNA of pregnant mothers with preeclampsia toxemia (PET). As discussed above, a previous study demonstrated, by using single-molecule real-time sequencing technology, that the proportion of long cell-free DNA in plasma is significantly reduced in pregnancies with preeclampsia compared to normal pregnancies (Yu et al., Proc. Natl. Acad. Sci. USA 118, (2020): e2114937118). Technologies such as sequencing platforms that use bridge amplification, however, have inferior discriminatory power for this purpose due to the inability of the technologies to sequence long DNA sequences having lengths greater than 600 base pairs. The provided assay guidance method was used to advantageously develop a digital PCR method capable of effectively comparing the size distributions of DNA in plasma from normal pregnant women and preeclamptic patients.

FIG. 7A illustrates an exemplary workflow for using in-silico simulation analysis to predict digital PCR performance. As shown in FIG. 7A, sequencing data associated with plasma cell-free DNA (cfDNA) from preeclamptic and normal pregnancies were analyzed to compare the size differences between the two groups. For each sample in the group, the molecules located in the potential design region were analyzed. In one example of the assay designs, one forward primer (F1) and two reverse primers (R1 and R2) were used. Sequenced fragments that span the sequences between F1 and R2 primer annealing sites, and that can therefore be amplified by F1 and R2 primers, are called digital PCR (dPCR) long fragments. Those sequenced fragments that span the sequences from F1 to R1, but do not span the R2 primer annealing site, are regarded as dPCR short fragments. FIG. 7A illustrates this PCR design. The three fragments 710 from among the sequences SMRT-seq fragments each cover both the first forward primer (F1) and the last reverse primer (R2). As a result, relatively long amplicons can be produced from these fragments in a digital amplification reaction, and these three fragments will be designated as long fragments. The two fragments 720 each cover the first forward primer (F1) and the first reverse primer (R1), but not the last reverse primer (R2). As a result, only relatively short amplicons can be produced from these fragments in a digital amplification reaction, and these two fragments will be designated as short fragments.

After determining which fragments from the long-read sequencing data will be designated as long or short fragments according to the above operations, the percentage of long cfDNA (denoted as L %) can be calculated based on the number of long dPCR fragments in relation to the number of short dPCR fragments in the in-silico dPCR analysis. To determine improved parameter values for the dPCR assay design, the in-silico simulation analysis is repeated for a series of different parameter values. In each simulation, the L % of each sample in each group is calculated. L % values are then compared between the two groups to determine which simulated parameter value provided the strongest discriminatory power. In some embodiments, the discriminatory power is measured using the area under the curve (AUC) calculated using a receiver operating characteristic (ROC) analysis.

Figure 7B:
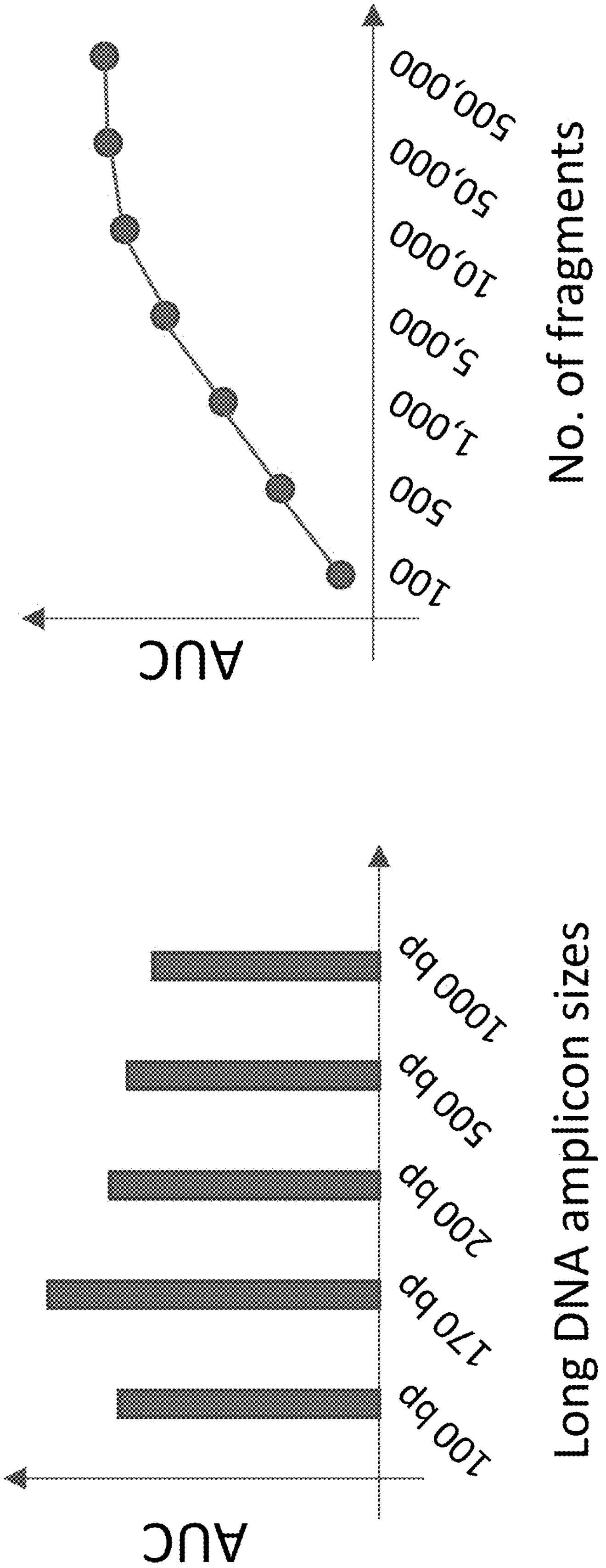
FIG. 7B presents graphs plotting results from the exemplary simulation of FIG. 7A.

For example, the left graph of FIG. 7B plots AUC results for different long DNA amplicon sizes, i.e., amplicons targeted by the F1 and R2 primers, as tested in different in silico simulations. The right graph of FIG. 7B plots AUC results for different simulated numbers of fragments in the plurality of nucleic acid molecules used in simulated digital amplification reactions. In both graphs, the plotted data can be used to identify which parameters, e.g., long DNA amplicon size or number of DNA fragments, result in desired high AUC values indicative of strong discriminatory power in distinguishing the PET and control test groups.

A. Determining Amplicon Sizes

Among the parameters considered in the design of the dPCR assay are the sizes of the relatively long and relatively short overlapping amplicons targeted by the primer sets added to the plurality of multiplexed digital amplification reactions. The provided in-silico dPCR simulation method can be used to evaluate the performance of assays using different sizes of long and short amplicons, thereby identifying which sizes provided improved differentiation ability.

In general, it can be preferable to design the multiplexed digital amplification assay such that the relatively shorter region targeted for amplification has as short a length as possible. A shorter length not only can increase the efficiency of amplification, e.g., PCR amplification, but also can ensure that the difference in size between the short and long amplicons is maximized. Each region target for amplification in the assay is targeted by a pair of forward and reverse primers, and a probe. The typical length of each PCR primer is approximately 25 bp, and the typical length of the probe is approximately 20 bp. Accordingly, in some embodiments, the minimal length of the shorter amplicon is approximately 70 bp (25-bp primer+25-bp primer+20-bp probe). In other embodiments, the length of the shorter amplicon is between about 40 bp and about 100 bp, e.g., between about 40 bp and about 76 bp, between about 46 bp and about 82 bp, between about 52 bp and about 88 bp, between about 58 bp and about 94 bp, or between about 64 bp and about 100 bp. In terms of upper limits, the shorter amplicon can have a size that is, for example, less than about 100 bp, e.g., less than about 94 bp, less than about 88 bp, less than about 82 bp, less than about 76 bp, less than about 70 bp, less than about 64 bp, less than about 58 bp, less than about 52 bp, or less than about 46 bp. In terms of lower limits, the shorter amplicon can have a size that is, for example, greater than about 40 bp, e.g., greater than about 46 bp, greater than about 52 bp, greater than about 58 bp, greater than about 64 bp, greater than about 70 bp, greater than about 76 bp, greater than about 82 bp, greater than about 88 bp, or greater than about 94 bp. Larger short region sizes, e.g., greater than 100 bp, and smaller short region sizes, e.g., less than about 40 bp, are also contemplated.

The multiplexed digital amplification assay can be designed such that the relatively longer region targeted for amplification has as a length suitably balancing amplification efficiency and discriminatory power. As discussed above, a shorter length for the relatively longer amplicon can increase the efficiency of amplification, e.g., PCR amplification, of this amplicon. A longer length for the relatively longer amplicon can, however, be beneficial for increasing the difference in sizes between the longer and shorter amplicons of the assay. To balance these competing considerations, the longer amplicon can have a length that is, for example, between about 100 bp and about 1000 bp, e.g., between about 100 bp and about 640 bp, between about 190 bp and about 730 bp, between about 280 bp and about 820 bp, between about 370 bp and about 910 bp, or between about 460 bp and about 1000 bp. The relatively longer amplicon can have a size that is, for example, between about 100 bp and about 250 bp, e.g., between about 100 bp and about 190 bp, between about 115 bp and about 205 bp, between about 130 bp and about 220 bp, between about 145 bp and about 235 bp, or between about 160 bp and about 250 bp. In terms of upper limits, the longer amplicon can have a size that is, for example, less than about 1000 bp, e.g., less than about 910 bp, less than about 820 bp, less than about 730 bp, less than about 640 bp, less than about 550 bp, less than about 460 bp, less than about 370 bp, less than about 280 bp, less than about 250 bp, less than about 235 bp, less than about 220 bp, less than about 205 bp, less than about 190 bp, less than about 175 bp, less than about 160 bp, less than about 145 bp, less than about 130 bp, or less than about 115 bp. In terms of lower limits, the longer amplicon can have a size that is, for example, greater than about 100 bp, e.g., greater than about 115 bp, greater than about 130 bp, greater than about 145 bp, greater than about 160 bp, greater than about 175 bp, greater than about 190 bp, greater than about 205 bp, greater than about 220 bp, greater than about 235 bp, greater than about 250 bp, greater than about 280 bp, greater than about 370 bp, greater than about 460 bp, greater than about 550 bp, greater than about 640 bp, greater than about 730 bp, greater than about 820 bp, or greater than about 910 bp. Larger sizes, e.g., greater than about 1000 bp, and smaller sizes, e.g., less than about 100 bp, are also contemplated.

Figure 8:
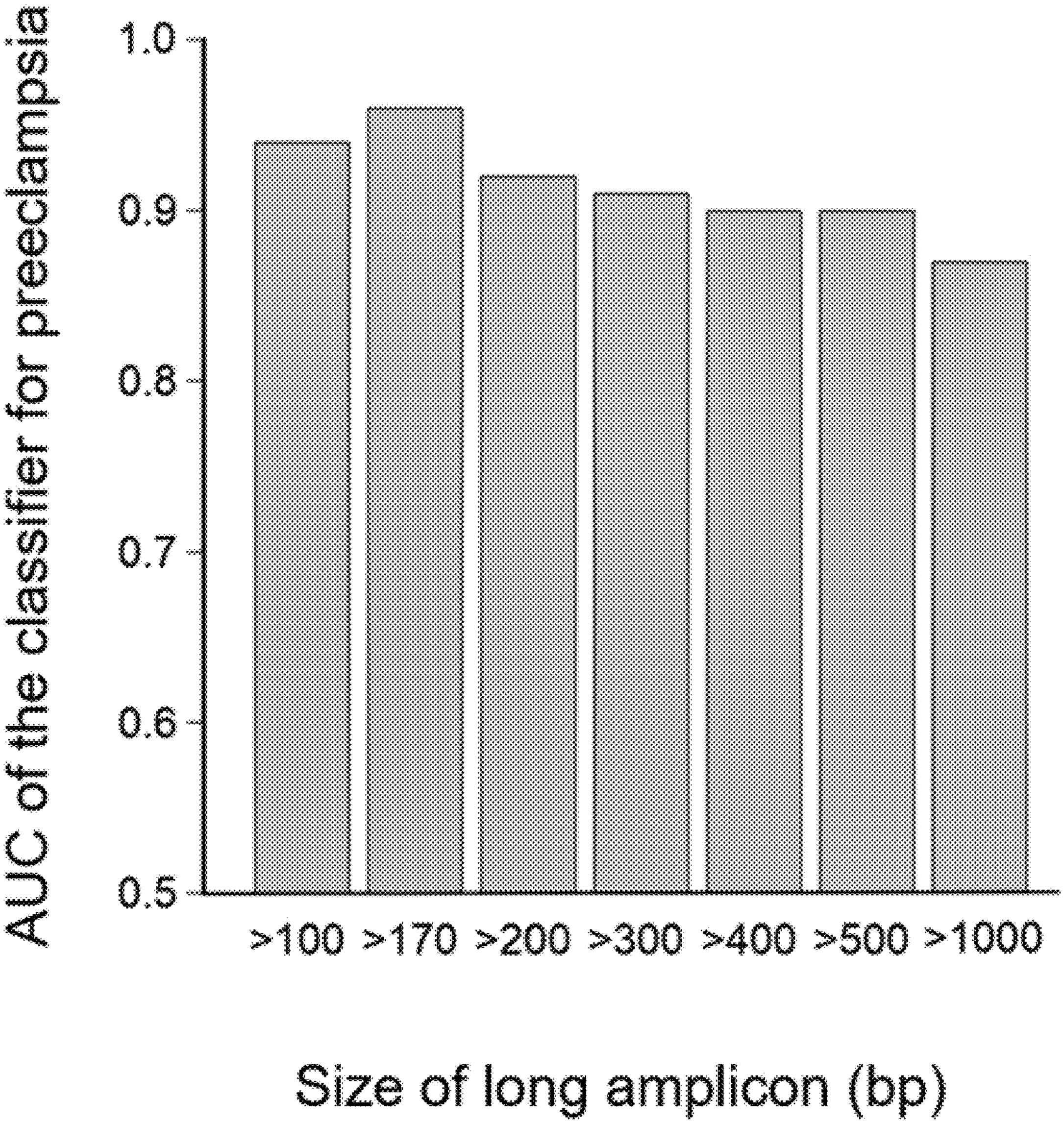
FIG. 8 presents a graph plotting the area under the curve (AUC) for the receiver operating characteristic (ROC) of differentiating preeclampsia toxemia (PET) from control subjects using simulations of digital amplification reactions with different long amplicon sizes.

FIG. 8 presents a graph plotting results from in-silico dPCR simulations based on SMRT sequencing data from 10 preeclamptic and 10 normal pregnancies reported previously (Yu et al., Proc. Natl. Acad. Sci. USA 118, (2020): e2114937118). The simulations evaluated the best sizes for the short and long amplicons of the multiplexed digital amplification reactions. The short amplicon of the simulations was configured to amplify as much cfDNA within the design region as possible in order to represent the total number of plasma cfDNA molecules. Accordingly, the size of the short amplicon was set at 70 bp, roughly equal to the sum of the lengths of two primers (25 bp×2) and a probe (20 bp). To determine the optimal size of the long amplicon, simulations were performed using the following sizes for the relatively longer amplicon: 100 bp, 170 bp, 200 bp, 300 bp, 400 bp, 500 bp, and 1000 bp. As the sequencing depth of the samples is shallow, with an average depth of approximately 0.5-fold, fragments from different locations of the genome were pooled. Approximately 5000 fragments were pooled from different locations for each simulation.

FIG. 8 shows the AUC results of simulations involving long amplicon sizes ranging from 100 to 1000 bp and a fixed short amplicon size of 70 bp. The long amplicon size of 170 bp provides the highest AUC among the simulated sizes. Therefore, an optimal size range for long amplicons (nucleic acid molecules, such as DNA and/or RNA) can be 100-200 bp, and more specifically can be between any of the following numbers: 110 bp, 120 bp, 130 bp, 140 bp, 150 bp, 160, 170 bp, 180 bp, and 190 bp, for short amplicons being 70 bp (or more broadly 70-100 bp, 70-90 bp, or 70-80 bp) as the optimal sizes for the long and short amplicons, respectively, for this multiplexed digital amplification assay.

B. Determining Fragment Count

Another parameter considered in the design of a dPCR assay is the minimum number of nucleic acid molecules, e.g., DNA fragments, necessary to achieve optimal discriminatory power in the multiplexed digital amplification assay. While performing the assay with a smaller number of nucleic acid molecules can simplify and streamline the assay, this benefit must be weighed against the improved reliability and accuracy of the assay resulting from the use of a larger number of nucleic acid molecules.

The number of nucleic acid molecules used in the assay can be, for example, between about 100 nucleic acid molecules and about 500,000 nucleic acid molecules, e.g., between about 100 nucleic acid molecules and about 17,000 nucleic acid molecules, between about 230 nucleic acid molecules and about 39,000 nucleic acid molecules, between about 550 nucleic acid molecules and about 91,000 nucleic acid molecules, between about 1300 nucleic acid molecules and about 210,000 nucleic acid molecules, or between 3000 nucleic acid molecules and about 500,000 nucleic acid molecules. In terms of upper limits, the number of nucleic acid molecules can be, for example, less than about 500,000 nucleic acid molecules, e.g., less than about 210,000 nucleic acid molecules, less than about 91,000 nucleic acid molecules, less than about 39,000 nucleic acid molecules, less than about 17,000 nucleic acid molecules, less than about 7000 nucleic acid molecules, less than about 3000 nucleic acid molecules, less than about 1300 nucleic acid molecules, less than about 550 nucleic acid molecules, or less than about 230 nucleic acid molecules. In terms of lower limits, the number of nucleic acid molecules can be, for example, greater than about 100 nucleic acid molecules, e.g., greater than about 230 nucleic acid molecules, greater than about 550 nucleic acid molecules, greater than about 1300 nucleic acid molecules, greater than about 3000 nucleic acid molecules, greater than about 7000 nucleic acid molecules, greater than about 17,000 nucleic acid molecules, greater than about 39,000 nucleic acid molecules, greater than about 91,000 nucleic acid molecules, or greater than about 210,000 nucleic acid molecules. Larger numbers of nucleic acid molecules, e.g., greater than 500,000 nucleic acid molecules, and smaller numbers of nucleic acid molecules, e.g., less than 100 nucleic acid molecules, are also contemplated.

Figure 9:
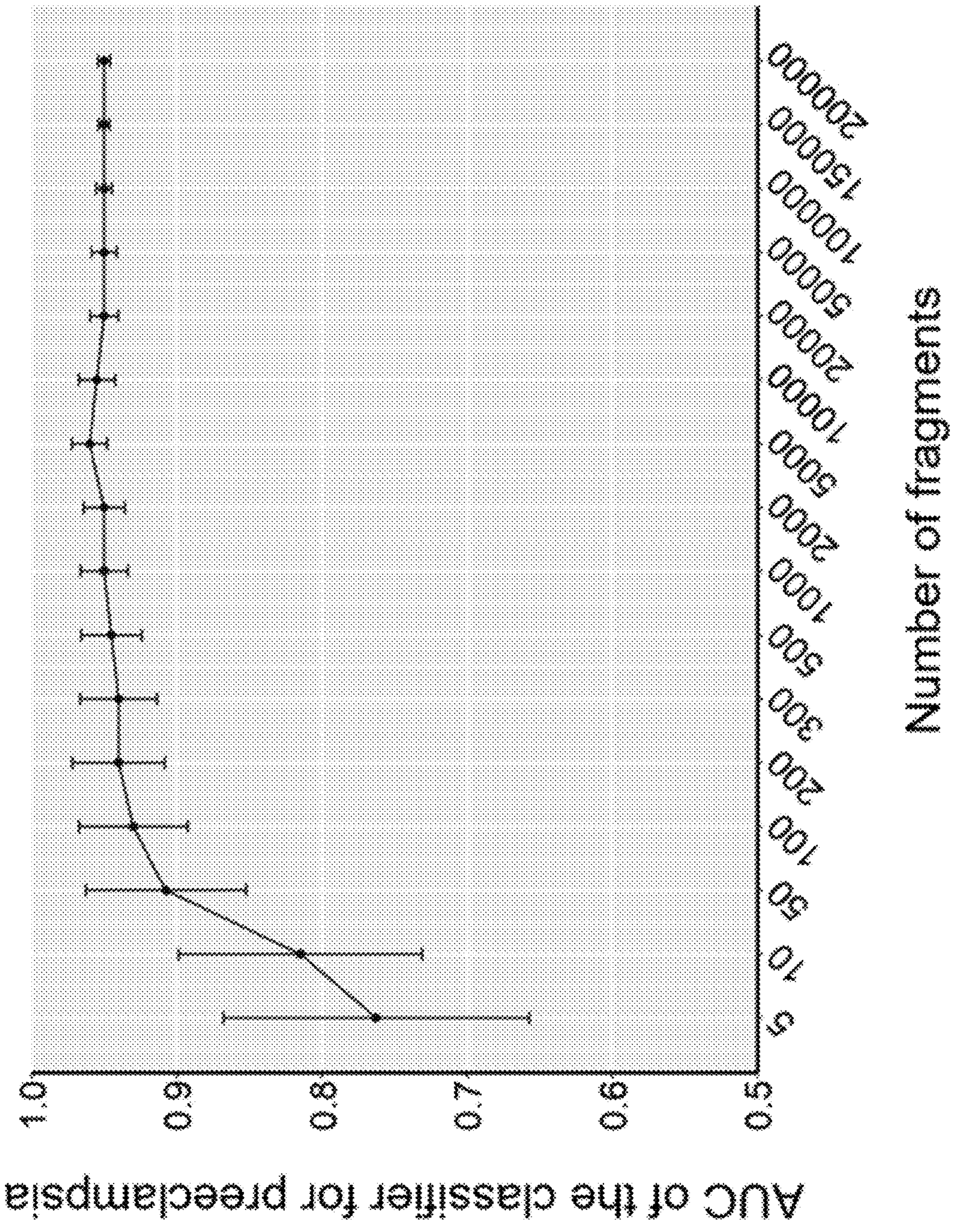
FIG. 9 presents a graph plotting the area under the curve (AUC) for the receiver operating characteristic (ROC) of differentiating preeclampsia toxemia (PET) from control subjects using simulations of digital amplification reactions with different numbers of nucleic acid fragments.

FIG. 9 presents a graph plotting results from in-silico dPCR simulations based using different numbers of sequenced fragments, ranging from 500000 to 5 fragments. For each tested number of sequenced fragments, the simulation was run 50 times with random sampling of the fragments. The median and standard deviation (SD) of the AUC values obtained from 50 simulations were then calculated. As shown in FIG. 9, the AUC plateaued when more than 5000 fragments were used, with a very small standard deviation (less than 0.015). Therefore, the in-silico PCR indicated that at least 5000 molecules were required to achieve robust discriminatory power for this multiplexed digital amplification assay.

C. Determining Target Regions for Amplification-Single Copy and Repeats

Another parameter considered in the design of a dPCR assay is the identity of the regions or sequences targeted for amplification to achieve optimal discriminatory power in the multiplexed digital amplification assay. For example, the targeted regions or sequences could be those for which there is a single copy or multiple copies (i.e., a repeated sequence) in a human genome. Targeting repeated sequences within the genome can advantageously improve the analytical sensitivity of the method for quantifying molecules of different sizes since the increased number of molecules to be analyzed can reduce sampling variation. Accordingly, using repeated sequences can provide more amplicons to be analyzed, potentially providing improved dPCR results.

Figure 10A:
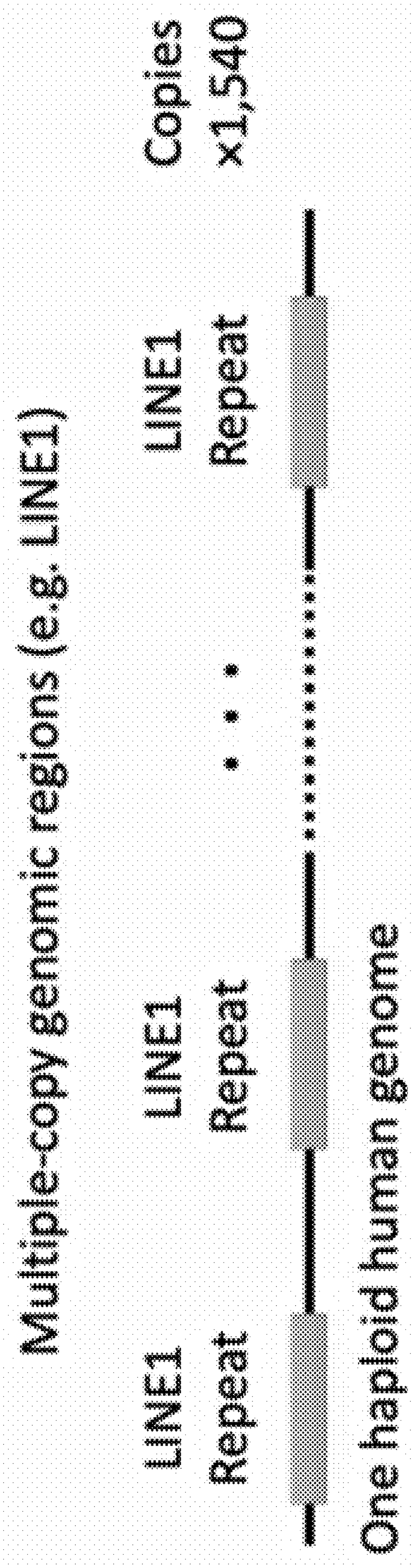
FIG. 10A presents a schematic illustration of a multicopy repeated region of a genome.
Figure 10B:
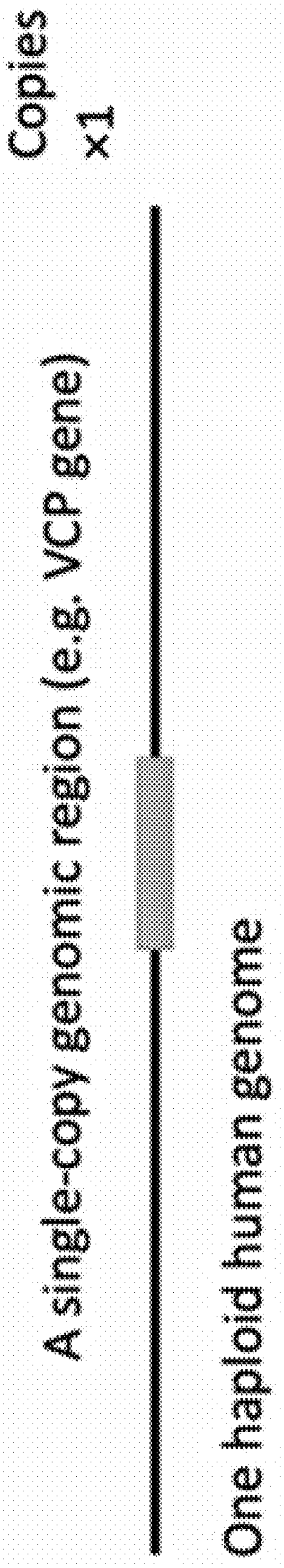
FIG. 10B presents a schematic illustration of a single-copy region of a genome.

As an example, the LINE1 repetitive element can be targeted for amplification. As illustrated in FIG. 10A, by designing a size-based digital PCR assay based on the LINE1 repetitive element, then for one haplotype human genome, multiple signals can be produced since LINE1 has approximately 1540 genomic copies. Alternatively, and as illustrated in FIG. 10B, if the size assay is alternatively designed based on a single-copy genomic region, such as the VCP gene, then one signal can be produced for one haplotype human genome.

Notably, the benefits of using repeated multi-copy regions for the provided multiplexed digital amplification assays can be more generally applicable to the shared primer assay exemplified in FIGS. 4-6 than to the separate primer assay exemplified in FIGS. 1-3. This is because the separate primer assay depends on observing two or more probes associated with two or more independent amplicons in a compartment or partition, e.g., droplet, of the digital assay. If signals from multiple probes are detected from a single compartment, then that compartment is identified as containing a relatively long nucleic acid including multiple targeted regions targeted for amplification. If, however, nucleic acid molecules with repeat regions are used, then there can be an increased likelihood that a compartment may include multiple short nucleic acid molecules, each having a different targeted amplicon of the repeat region. In this case, multiple signals could be detected from the compartment, even though the compartment does not include a relative long nucleic acid molecule including multiple targeted amplicons. This potential confounding factor leading to false positives is not an issue if the plurality of nucleic acid molecules is diluted such that no compartment includes more than one nucleic acid molecule template. This potential for false positives is also not an issue for the shared primer assay of FIGS. 4-6, regardless of the extent of dilution of the plurality of nucleic acid molecules.

In one embodiment, the target regions for the analysis of the size distribution of nucleic acids using digital PCR could be one copy or multiple copies (i.e., repeated sequences) in a human genome. Targeting repeated sequences within the genome may improve the analytical sensitivity of the method for quantifying molecules of different sizes as the increased number of molecules to be analyzed would reduce the sampling variation. The configurations presented in FIGS. 1 and 2 make use of the co-presence of signals from each short PCR amplicon to determine the presence of a long DNA molecule in a compartment, which overcome the compromised amplification efficiency associated with long PCR amplicons. Such an approach can be complicated when targeting repetitive regions, since the double positive signal may originate from the same long molecule or from two repeat molecules co-located in one compartment. To overcome this problem, dilution should be performed so that on average no more than one molecule is present in one compartment. Alternatively, the configuration shown in FIGS. 4A and 4B is readily adaptable to a design based on repetitive elements.

D. Results

Application of multiplexed digital amplification assays designed with guidance from in silico simulations confirmed the ability of the assays to differentiate preeclamptic from control subjects. Effective discrimination was achieved with assays using shared primer pairs to amplify repeat regions of the genome, and assays using separate primer pairs to amplify single-copy regions.

1. Shared Primer Assay with Repeat Regions

Based on the in-silico dPCR results, an assay was developed to differentiate preeclamptic from control subjects with multiplexed digital amplification reactions using shared primers. A size of 170 bp was selected for the long amplicon and a size of 70 bp for the short amplicon. To increase the number of usable molecules from limited plasma DNA, the size assay was designed based on repetitive regions, in this case, the LINE1 region. This design used the principles described in FIGS. 4A and 4B, and included three primers, LINE1 Forward Primer 1, LINE1 Reverse Primer 1, and LINE1 Reverse Primer 2, as well as two probes, LINE1_70 bp Probe, and LINE1_170 bp Probe. The LINE1 Forward Primer 1/LINE1 Reverse Primer 1 pair is used to produce PCR products of 70 bp, and the LINE1 Forward Primer 1/LINE1 Reverse Primer 2 pair is used to produce PCR products of 170 bp. The sequences for PCR primers and probes are shown in Table 1 below:

TABLE 1

Primer and probe sequences for shared primer assay with repeat regions. Table discloses SEQ ID NOS 1-2, 1, and 3-4, respectively, in order of appearance.

| | |
|---|---|
| LINE1 Forward Primer 1 | 5'-CTCTGAGCTACGGGAGGACATT-3' |
| LINE1 Reverse Primer 1 | 5'-TTCTTCTAAATTTTTTTCAAAGTTTTCAAC-3' |
| LINE1 Reverse Primer 2 | 5'-CTCTGAGCTACGGGAGGACATT-3' |
| LINE1_70 bp Probe | 5'-Cy5-CTTTGCCTTTGGTTTG-MGB-3' |
| LINE1_170 bp Probe | 5'-FAM-AGCCTTGGTTTTCAG-MGB-3' |

The designed LINE1 assay targeted approximately 1600 regions repeated across the human genome. An in-silico dPCR analysis of these targeted regions was performed using the PacBio sequencing data of the 10 preeclamptic and 10 control subjects. As shown in the graph FIG. 12A, preeclamptic subjects have a significantly lower L % than control subjects (median, 64% vs. 75%, P value=0.0002). FIG. 12B plots data from an ROC analysis of the LINE1 assay, showing that the AUC for differentiating between the two groups is 0.95. In an experimental analysis, these values would be expected.

The assay was tested using genomic DNA (gDNA) extracted from buffy coats. The extracted buffy coat gDNA with a size predominantly around 30 kb can be used as a control sample of longer DNA. Additionally, shorter gDNA was generated by sonicating the buffy coat gDNA to a size peaking at 178 bp using an ultrasonicator. The LINE1 assay was performed with both sonicated and non-sonicated samples of gDNA. In this example, a droplet digital PCR platform was used to compartmentalize DNA into droplets, perform PCR, and read the results. The PCR reactions were prepared in a volume of 20 μL, each including 10 μg of template DNA, 10 μL of 2×ddPCR Supermix for Probes (Bio-Rad), a final concentration of 900 μmol/L of each primer, and a final concentration of 250 nmol/L of each probe. The droplet generation and PCR reaction were performed using the QX ONE Droplet Digital PCR (ddPCR) System (Bio-Rad). The thermal profile of the assay involved initiation at 37° C. for 30 minutes, then holding at 95° C. for 10 minutes, followed by 45 cycles of 94° C. for 30 seconds and 60° C. for 1 minute, and a final incubation at 98° C. for 10 minutes.

The number of long DNA molecules was determined by using droplets containing both the 170 bp and 70 bp amplicons. The total number of DNA molecules was represented by the number of droplets containing the 70 bp amplicon. The non-sonicated gDNA sample contained 811 copies of long DNA molecules >170 bases in a total of 1059 total DNA molecules, giving a percentage of long DNA molecules of 76.6%. In comparison, the sonicated gDNA sample contained only nine long DNA molecules out of 1119 total DNA molecules, giving a L % of 0.8%. These results confirm that the LINE1 digital PCR assay performs well for analyzing the size distributions of DNA molecules.

2. Separate Primer Assay with Single Copy Regions

Another assay was developed assay to differentiate preeclamptic from control subjects with multiplexed digital amplification reactions using separate primers. This design used the principles illustrated in FIG. 1 to target the single-copy VCP gene and profile nucleic acids longer than 1001 bp or 533 bp. In the assay for detecting fragments longer than 1001 bp, two pairs of primers, VCP_0 Forward Primer/VCP_0 Reverse primer and VCP_1001 Forward Primer/VCP_1001 Reverse Primer, were used to amplify two regions (namely, VCP 0 region, and VCP 1001 region) separated by 1001 bp. Two probes, VCP_0 Probe and VCP_1001 Probe, were used to detect the two amplicons. Similarly, the assay for detecting fragments longer than 533 bp used two pairs of primers (VCP_0 Forward Primer/VCP_0 Reverse primer and VCP_533 Forward Primer/VCP_533 Reverse Primer) for amplifying two regions separated by 533 bp, and two probes (VCP_0 Probe and VCP_533 Probe) to detect amplification of the two regions. The amplicon size of the VCP_0 Forward Primer/VCP_0 Reverse primer is 73 bp. Droplets containing this amplicon were used to determine the total number of template DNA molecules in the sample. The sequences for PCR primers and probes are shown in Table 2 below.

TABLE 2

Primer and probe sequences for separate primer assay with single-copy regions. Table discloses SEQ ID NOS 5-13, respectively, in order of appearance.

| | |
|---|---|
| VCP_0 Forward Primer | 5'-CCTGATTCTAGATTATCTTGATATCCTCA-3' |
| VCP_0 Reverse Primer | 5'-ATTCCACTGGGGTTAGGGTTG-3' |
| VCP_0 Probe | 5'-Cy5-ATTCTACCTTCCCTTTAGAC-MGB-3' |
| VCP_1001 Forward Primer | 5'-GGGAGGTCTGTGGACCCTATC-3' |
| VCP_1001 Reverse Primer | 5'-TGAGCTGAGATGAGACTCATATACTTATC-3' |
| VCP_1001 Probe | 5'-FAM-CTTCCCCAACCATCAG-MGB-3' |
| VCP_533 Forward Primer | 5'-TCTTCTCGGCCTTATTCCAAATT-3' |
| VCP_533 Reverse Primer | 5'-GAATTTTAATAGGGCATCAAAGATAAAGA-3' |
| VCP_533 Probe | 5'-VIC-AATGGATTCACCTCAGC-MGB-3' |

In this example, the Bio-Rad droplet digital PCR platform was used to compartmentalize the DNA into droplets, perform PCR, and read the results. The PCR settings for the 1001-bp assay and the 533-bp assay were the same, as described below. The reactions were each prepared in a volume of 20 μL, each including 3 ng of template DNA, 10 μL of 2× ddPCR Supermix for Probes (Bio-Rad), a final concentration of 900 μmol/L of each primer, and a final concentration of 250 nmol/L of each probe. The droplet generation and PCR reaction were performed using the QX ONE Droplet Digital PCR (ddPCR) System (Bio-Rad). The thermal profile of the assay involved initiation at 37° C. for 30 minutes, then holding at 95° C. for 10 minutes, followed by 45 cycles of 94° C. for 30 seconds and 57° C. for 1 minute, and a final incubation at 98° C. for 10 minutes.

Genomic DNA (gDNA) extracted from buffy coats was used to test the assay. The extracted buffy coat gDNA with a size predominantly around 30 kb can be used as a control sample of longer DNA. Additionally, shorter gDNA was generated by sonicating the buffy coat gDNA to a size peaking at 280 bp using a Covaris ultrasonicator. The two assays were performed using both sonicated and non-sonicated samples of gDNA. The results are shown in Table 3 and Table 4 below.

TABLE 3

Results from 1001-bp assay.

| | Total droplet number (M) | Number of droplets with positive signals of VCP0 only (X) | VCP1001 only (Y) | both VCP0 and VCP1001 (Z) | Deduced number of droplets with coincidental colocalization of VCP0 and VCP1001 (c) | Deduced number of droplets with long DNA molecules of >1001 bp (L = Z − c) | Percentage of long DNA molecules of >1001 bp [L % = L/(X + Z) × 100%] |
|---|---|---|---|---|---|---|---|
| Non-sonicated buffy coat gDNA | 39661 | 226 | 197 | 1720 | 1 | 1719 | 88.4% |

TABLE 3-continued

Results from 1001-bp assay.

| | Total droplet number (M) | Number of droplets with positive signals of VCP0 only (X) | VCP1001 only (Y) | both VCP0 and VCP1001 (Z) | Deduced number of droplets with coincidental colocalization of VCP0 and VCP1001 (c) | Deduced number of droplets with long DNA molecules of >1001 bp (L = Z − c) | Percentage of long DNA molecules of >1001 bp [L % = L/(X + Z) × 100%] |
|---|---|---|---|---|---|---|---|
| Sonicated buffy coat gDNA (size peak = 280 bp) | 44618 | 1970 | 2271 | 137 | 63 | 111 | 1.2% |

TABLE 4

Results from 533-bp assay.

| | Total droplet number (M) | Number of droplets with positive signals of VCP0 only (X) | VCP533 only (Y) | both VCP0 and VCP533 (Z) | Deduced number of droplets with coincidental colocalization of VCP0 and VCP533 (c) | Deduced number of droplets with long DNA molecules of >533 bp (L = Z − c) | Percentage of long DNA molecules of >533 bp [L % = L/(X + Z) × 100%] |
|---|---|---|---|---|---|---|---|
| Non-sonicated buffy coat gDNA | 43950 | 115 | 105 | 1828 | 1 | 1827 | 94.1% |
| Sonicated buffy coat gDNA (size peak = 280 bp) | 44122 | 1888 | 2121 | 169 | 100 | 69 | 3.4% |

The results of the 1001 bp assay (Table 3) show that the non-sonicated buffy coat gDNA primarily consisted of DNA molecules with a length of at least 1001 bp, since most of the positive droplets displayed both VCP0 and VCP1001 signals. For the sonicated buffy coat gDNA, a small proportion of positive droplets had dual positive signals of both VCP0 and VCP1001, indicating a smaller proportion of long molecules of >1001 bp. Among the droplets that display dual positive signals, a portion may be caused by coincidental colocalization of the short DNA molecules from both VCP0 and VCP1001 regions. In one embodiment, the number of droplets with coincidental colocalization of one short DNA molecule spanning only the VCP0 region and one short DNA molecule spanning only the VCP1000 region (denoted as c) can be calculated as follows:

$$c = \left(\frac{X+c}{M}\right)\left(\frac{Y+c}{M}\right)M,$$

where M represents the total number of droplets, X represents the number of droplets that only contained the VCP0 signal, and Y represents the number of droplets that only emit the VCP1001 signal. Thus, the number of positive droplets containing long DNA molecules of >1001 bp (L) can be calculated as L=Z−c, where Z represents the number of droplets that emit both VCP0 and VCP1001 signals. Accordingly, the percentage of long DNA molecules of >1001 bp (L %) can be calculated by dividing the number of positive droplets containing long DNA molecules of >1001 bp by the total number of droplets emitting the VCP0 signal (including both the number of droplets that only emit the VCP0 signal and the number of droplets that emit both VCP0 and VCP1001 signals) (L %=L/(X+Z)×100%). The same calculations can be applied to calculate the percentage of molecules greater than 533 bp when using the 533 bp assay (Table 4).

As shown in Table 3 and Table 4, the percentage of long DNA molecules longer than 1001 bp was 88.4% and 1.2% in non-sonicated and sonicated buffy coat DNA, respectively. The percentage of long DNA molecules longer than 533 bp was 94.1% and 3.4% in non-sonicated and sonicated buffy coat DNA, respectively. These results demonstrate that the digital PCR assay based on two separate primer pairs spanning a target molecule in a reaction partition can be used to determine the presence of long DNA molecules.

E. Method

Figure 11:
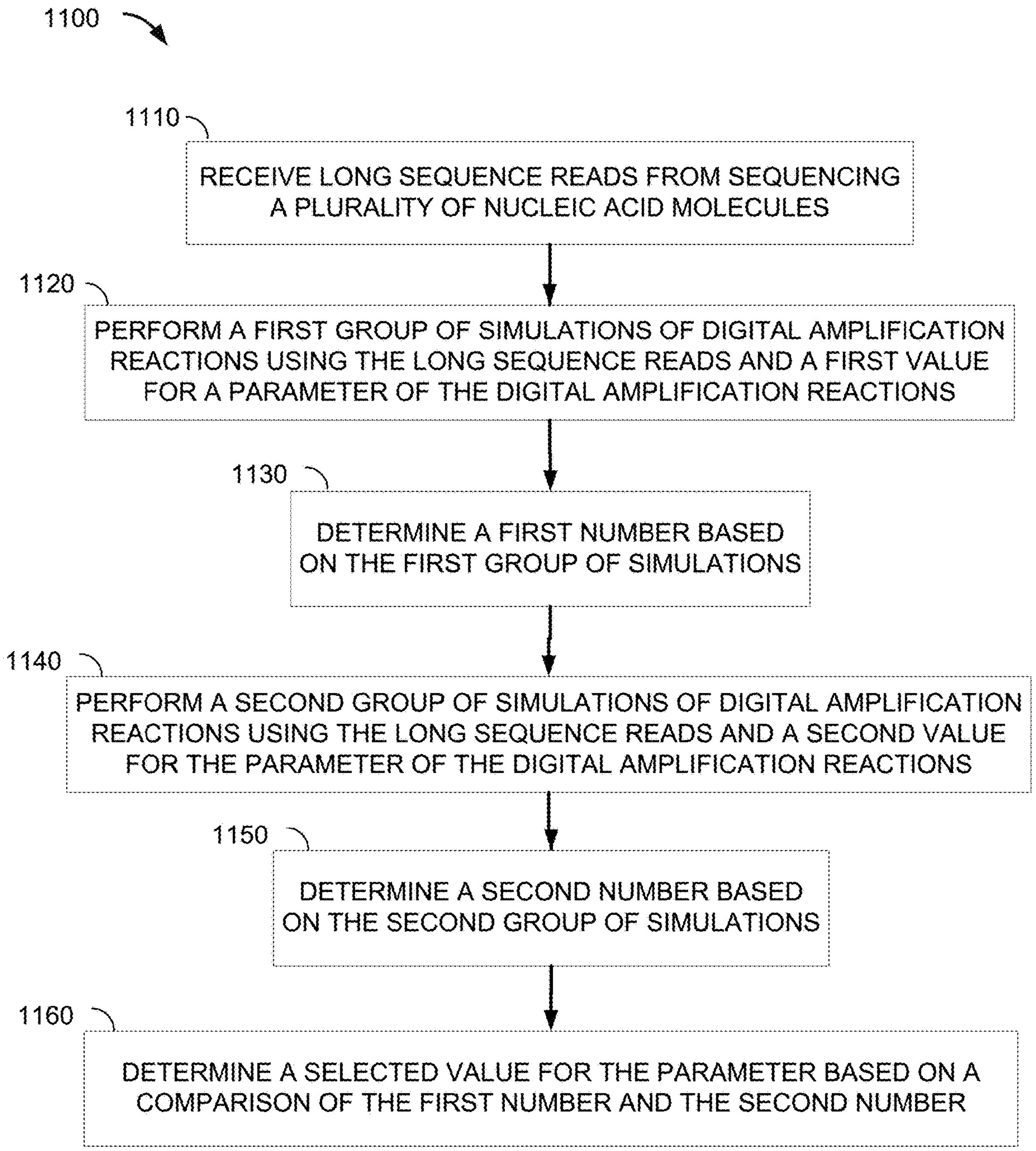
FIG. 11 presents a flowchart of a method for using long DNA sequencing data to guide digital amplification reaction design in accordance with a provided embodiment.

FIG. 11 presents a flowchart of a method 1100 for selecting an assay parameter, based on simulations using long sequence read data, for a multiplexed digital amplification assay measuring the sizes of a plurality of nucleic acid molecules according to embodiments of the present disclosure. Various examples of method 1100 are described above. Method 1100 can be performed partially or entirely using a computer system.

At block 1110, long sequence reads from sequencing a plurality of nucleic acid molecules are received. In some embodiments, the plurality of nucleic acid molecules are nucleic acid molecules originating from a sample. In some embodiments, the sample is a biological sample taken from a subject. In some embodiments, the plurality of nucleic acid molecules includes or consists of a plurality of DNA molecules. In some embodiments, the plurality of nucleic acid molecules includes or consists of a plurality of RNA molecules. In some embodiments, the plurality of nucleic acid molecules includes or consists of a plurality of cell-free nucleic molecules, e.g., a plurality of cell-free DNA molecules. In some embodiments, the long sequence reads can have an average length that is greater than 500 bp, e.g., greater than 630 bp, greater than 790 bp, greater than 1000 bp, greater than 1300 bp, greater than 1600 bp, greater than 2000 bp, greater than 2500 bp, greater than 3200 bp, greater than 4000 bp, or greater than 5000 bp.

At block 1120, a first group of simulations of digital amplification reactions are performed using the long sequence reads and a first value for a tested parameter of the simulated digital amplification reactions. The simulated digital amplification reactions can be any of those disclosed herein. For example, in some embodiments, the simulated digital amplification reactions are in silico multiplexed digital amplification assays using shared primers as exemplified in FIGS. 4-6. In some embodiments, the simulated digital amplification reactions are in silico multiplexed digital amplification assays using separate primers as exemplified in FIGS. 1-3. The tested reaction parameter of the simulated digital amplification reaction can be any of those disclosed herein. In some embodiments, the parameter is a size of a region targeted for amplification by primers of the digital amplification reactions. In some embodiments, the parameter is the identity of the region targeted for amplification by primers of the digital amplification reactions. In some embodiments, the parameter is the number of different nucleic acid molecules, as represented by the long sequence reads, used as templates in the digital amplification reactions.

At block 1130, a first number is determined based on the results of the first group of simulations. In some embodiments, the first number represents a percentage (L %) of relatively long nucleic acid molecules associated with the long sequence reads, where the percentage is calculated based on a number of relatively long nucleic acid molecules in relation to a number of relatively short nucleic acid molecules as identified by the simulations of the first group. For example, when the simulated digital amplification reactions are in silico multiplexed digital amplification assays using shared primers as exemplified in FIGS. 4-6, then the first number can represent a percentage of the in silico digital assays for which an amplification product corresponding to the larger targeted region is produced. When the simulated digital amplification reactions are in silico multiplexed digital amplification assays using separate primers as exemplified in FIGS. 1-3, then the first number can represent a percentage of the in silico digital assays for which amplification products corresponding to all targeted regions are produced. In some embodiments, the first number relates to an area under a curve (AUC) as calculated using a receiver operating characteristic (ROC) analysis.

At block 1140, a second group of simulations of digital amplification reactions are performed using the long sequence reads and a second value for the tested parameter of the simulated digital amplification reactions. The second group of simulations are performed similarly to the first group of simulations of block 1120. In some embodiments, the second value of the tested parameter is greater than the first value of the tested parameter. In some embodiments, the second value is less than the first value. In some embodiments, method 1100 further includes an operation of performing a third group of simulations of digital amplification reactions performed using the long sequence reads and a third value for the tested parameter of the simulated digital amplification reactions. Method 1100 can also include additional operations of performing additional groups of simulations, each using a different value for the tested parameter. The number of different groups of simulations performed to test different parameter values can be, for example, at least 2, e.g., at least 3, at least 4, at least 6, at least 10, at least 15, at least 20, at least 30, at least 45, at least 65, or at least 100.

At block 1150, a second number is determined based on the second group of simulations. The second number is determined similarly to the first number of block 1130. For example, in some embodiments, the second number represents a percentage (L %) of relatively long nucleic acid molecules associated with the long sequence reads, where the percentage is calculated based on a number of relatively long nucleic acid molecules in relation to a number of relatively short nucleic acid molecules as identified by the simulations of the second group. In some embodiments, the second number relates to an area under a curve (AUC) as calculated using a receiver operating characteristic (ROC) analysis. In some embodiments, method 1100 further includes an operation of determining a third number based on a third group of simulations. Method 1100 can also include additional operations of determining additional numbers based on additional groups of simulations, each using a different value for the tested parameter.

At block 1160, a value for the tested parameter is selected based on a comparison of the first number and the second number. In some embodiments, a value for the tested parameter is selected based on a comparison of all numbers determined for all groups of performed simulations. The comparison can include determining which of the numbers is maximum. The comparison can include determining which of the numbers is a minimum. The comparison can include predicting a maximum or minimum based on interpolations and/or extrapolations using the numbers. In some embodiments, the parameter value is selected to maximize a corresponding predicted L % value. In some embodiments, the parameter value is selected to maximize a corresponding predicted AUC value.

VI. Comparison of Simulated PCR Results for Repeat and Single Copy

Figure 12A:
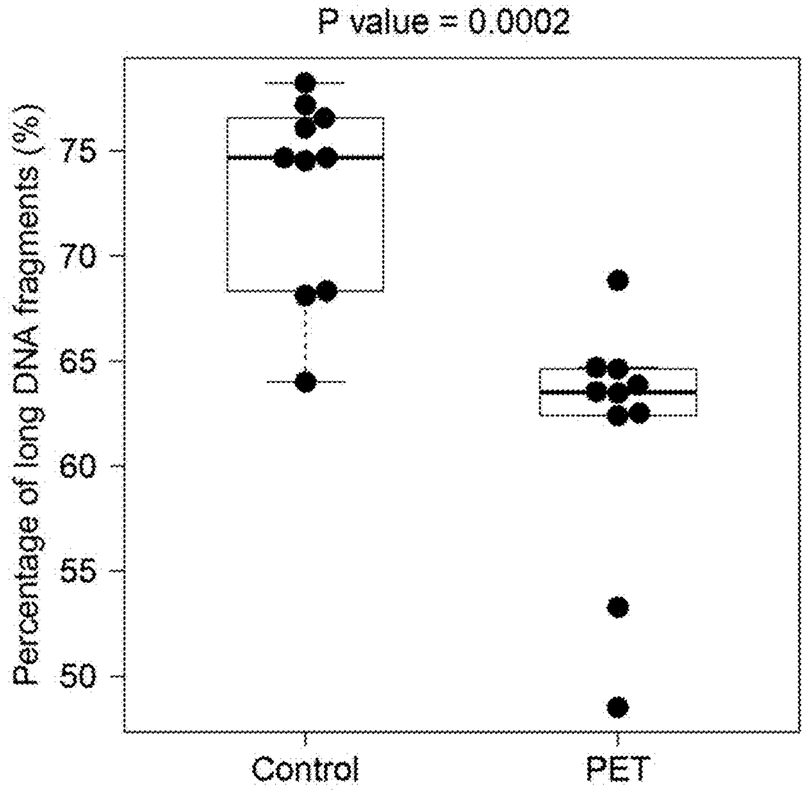
FIG. 12A presents a box plot showing percentages of long DNA fragments for preeclamptic and control pregnancies as determined using simulations of digital amplification of LINE1 repeat genomic sequences in accordance with a provided embodiment.
Figure 12B:
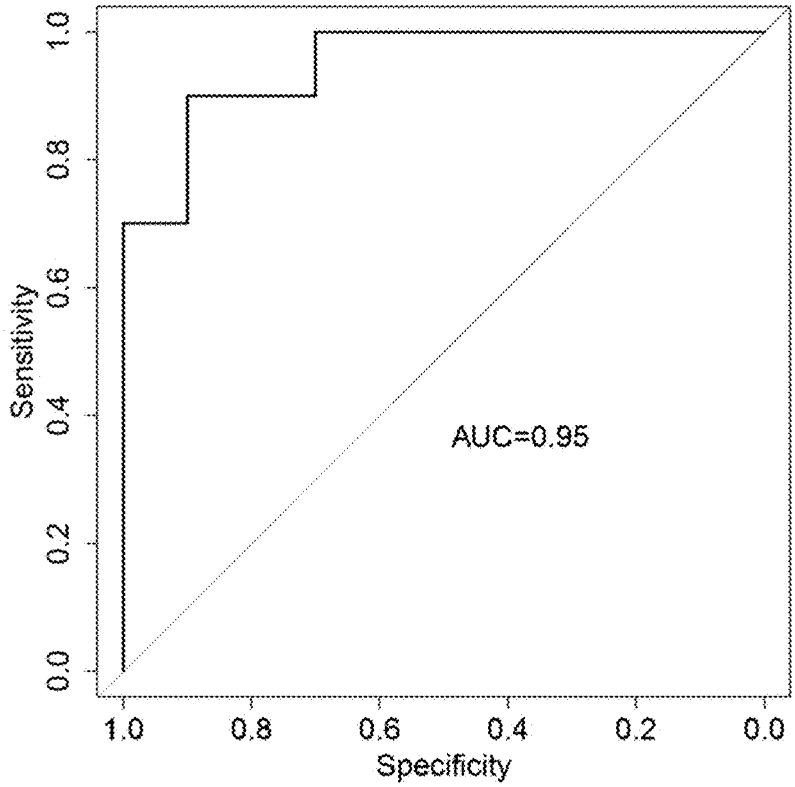
FIG. 12B presents a graph showing a ROC analysis for differentiating the groups measured in the simulation of FIG. 12A.

FIGS. 12A-12F present graphs plotting simulated results for differentiating control and PET samples using different multiplexed digital amplification assay procedures with targeting amplification of repeated or single-copy regions. FIGS. 12A and 12B show results from a simulated digital amplification assay using shared primers targeting regions of the LINE1 repeat sequence. As described in Section V.D.1. above, the longer region targeted for amplification in this assay had a length of 170 bp, and the shorter subregion targeted for amplification in the assay had a length of 70 bp. The data of FIGS. 12A and 12B show that the ability of the assay to differentiate the control and PET samples from one another was very high, with a P value of 0.001 and an AUC greater than 0.9.

Figure 12C:
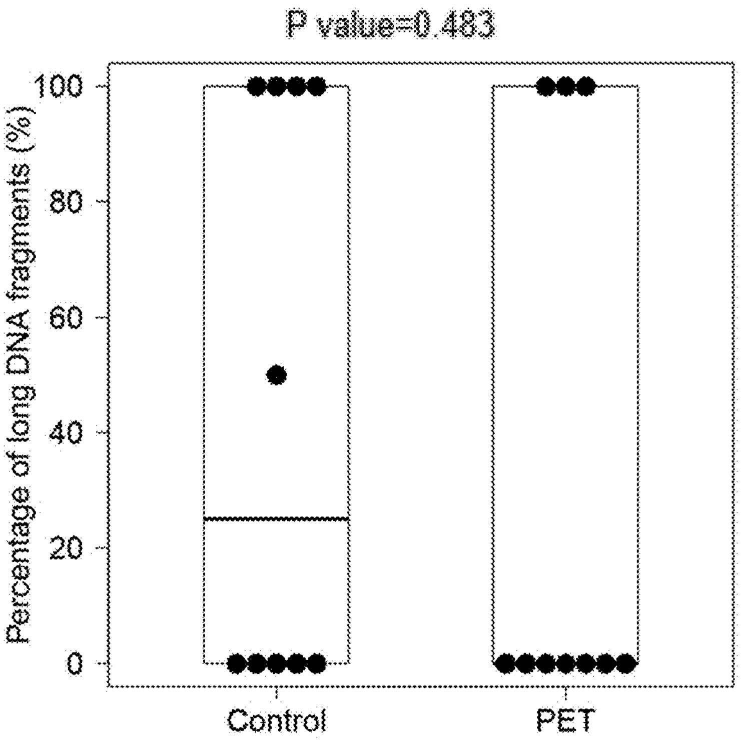
FIG. 12C presents a box plot showing percentages of long DNA fragments for preeclamptic and control pregnancies as determined using simulations of digital amplification of 533-bp and 73-bp regions of a VCP single-copy genomic sequence in accordance with a provided embodiment.
Figure 12D:
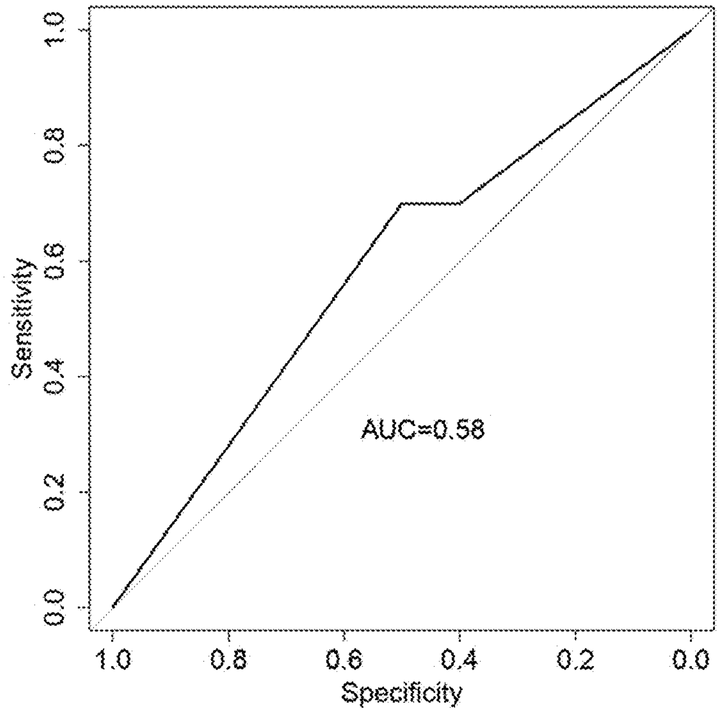
FIG. 12D presents a graph showing a ROC analysis for differentiating the groups measured in the simulation of FIG. 12C.
Figure 12E:
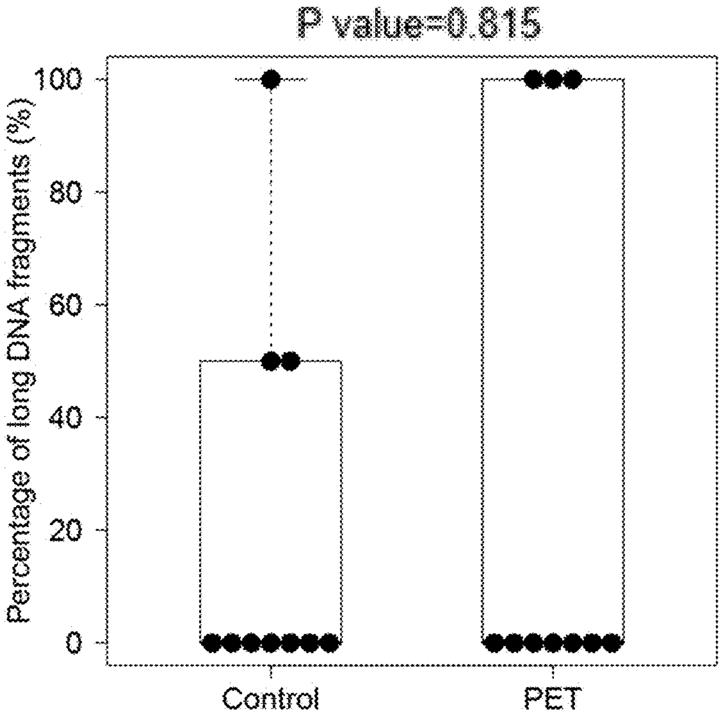
FIG. 12E presents a box plot showing percentages of long DNA fragments for preeclamptic and control pregnancies as determined using simulations of digital amplification of 1001-bp and 73-bp regions of a VCP single-copy genomic sequence in accordance with a provided embodiment.
Figure 12F:
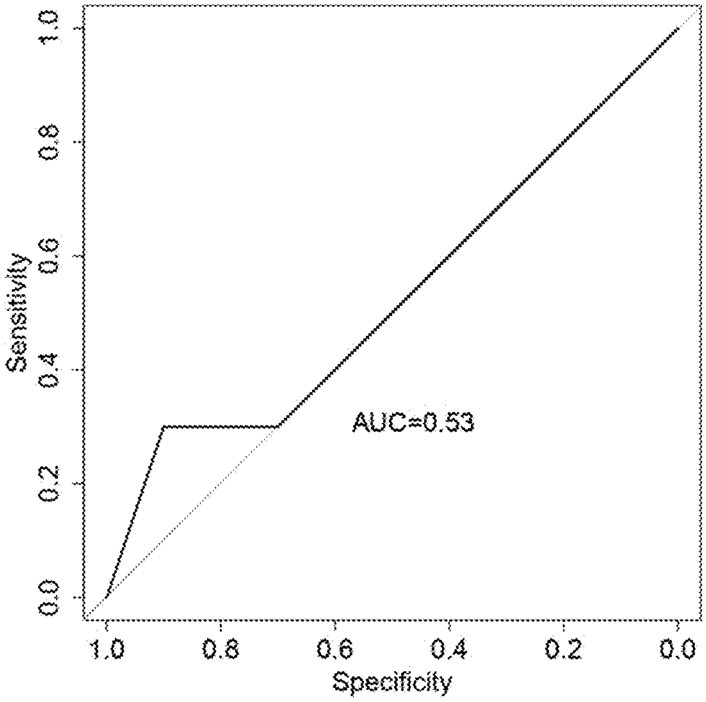
FIG. 12F presents a graph showing a ROC analysis for differentiating the groups measured in the simulation of FIG. 12E.

FIGS. 12C and 12D show results from a simulated digital amplification assay using separate primers targeting regions of the VCP single-copy gene. As described in Section V.D.2. above, the regions targeted for amplification in this assay were separated from one another by a distance of 533 bp. FIGS. 12E and 12F show results from another simulated digital amplification assay using separate primers targeting regions of the VCP single-copy gene. In this simulation, and as also described in Section V.D.2, the regions targeted for amplification were separated from one another by a distance of 1001 bp. The data of FIGS. 12C-12F show that the ability of these assays to differentiate the control and PET samples from one another was not as high as seen with the assay of FIGS. 12A and 12B.

While this difference between the performances of the different simulated assays may result in part from differences in sizes of the amplicons of the different assays, the primary driver of the higher discriminatory power of the FIGS. 12A and 12B assay is the use of the LINE1 repeat sequence. Because the PacBio data of the simulations does not have a very high coverage, the benefits of using a repeated sequence are particularly noticeable. Specifically, with the repeated sequence, one coverage of the genome can produce over 1000 signals, where the single-copy sequence can produce only either one or zero signals. This increase in the number of potential signals can significantly enhance the predictive specificity of the multiplexed digital amplification assay, as shown in FIGS. 12A-12F.

VII. Methods for Determining Pathology

In certain aspects, the present disclosure provides methods for determining the presence or classification of a pathology in a subject. These methods rely in part on the provided multiplexed digital amplification assays for measuring sizes of a plurality of nucleic acid molecules, e.g., cell-free DNA fragments in a biological sample, from the subject. As discussed above, various parameters can provide a statistical measure of a size profile of DNA fragments in the biological sample. A parameter can be defined using the sizes of all of the DNA fragments analyzed, or just a portion. In one embodiment, a parameter provides a relative abundance of short and long DNA fragments, where the short and long DNA may correspond to specific sizes or ranges of sizes.

A. Results

As an example, the provided methods for determining a pathology were used to determine a classification of preeclampsia based on the size of DNA in plasma from normal pregnant women and patients with preeclampsia. Sixteen control pregnancies and ten preeclamptic subjects were recruited. Plasma samples were obtained from each subject, and DNA was extracted using a QIAamp Circulating Nucleic Acid Kit (Qiagen) and quantified using a Qubit 3.0 (Invitrogen). Plasma DNA sizes were determined using three provided multiplexed digital amplification assays described in more detail above: the LINE1 repetitive assay (170 bp/70 bp), the VCP single-copy gene assay (533 bp/73 bp), and the VCP single-copy gene assay (1001 bp/73 bp). The dPCR profiles and the calculation of relative long cfDNA percentages were performed as those described in the simulations described above.

Figure 13A:
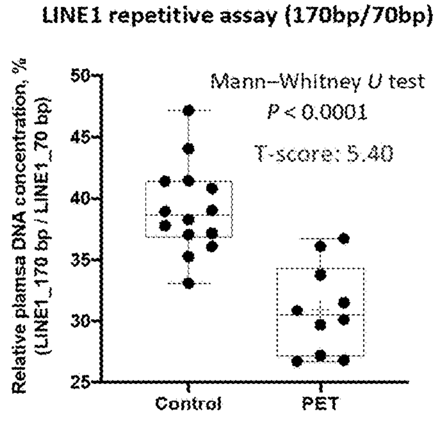
FIG. 13A presents a box plot showing percentages of long DNA fragments for preeclamptic and control pregnancies as determined using digital amplification of LINE1 sequences in accordance with a provided embodiment.
Figure 13B:
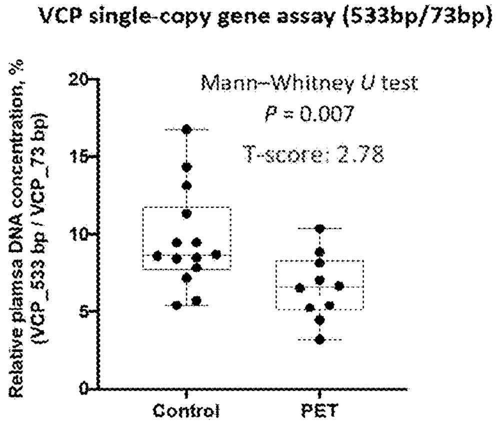
FIG. 13B presents a box plot showing percentages of long DNA fragments for preeclamptic and control pregnancies as determined using digital amplification of 533-bp and 73-bp sequences from a single-copy gene in accordance with a provided embodiment.
Figure 13C:
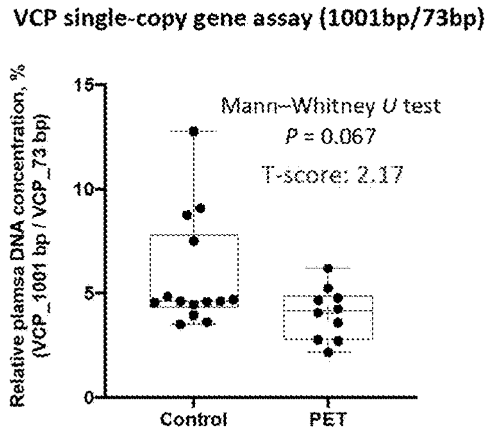
FIG. 13C presents a box plot showing percentages of long DNA fragments for preeclamptic and control pregnancies as determined using digital amplification of 1001-bp and 73-bp sequences from a single-copy gene in accordance with a provided embodiment.
Figure 13D:
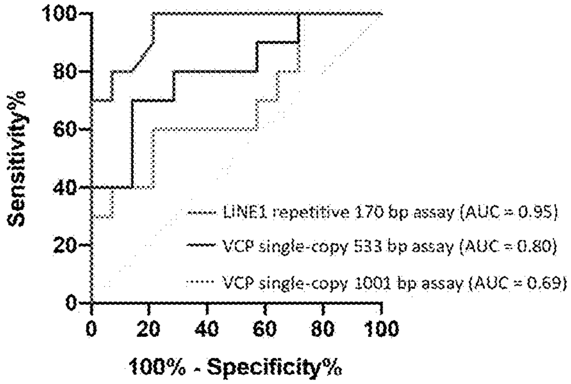
FIG. 13D presents a graph showing an ROC analysis of the digital amplification assays of FIGS. 13A-C.

Using the LINE1 assay, the preeclamptic group was shown to have a significantly lower percentage of long cfDNA of >170 bp (median, 30.5%; range, 26.7% to 36.8%) compared to the control group (median, 38.6%; range, 33.1% to 47.2%) (Mann-Whitney U test, P<0.0001) (FIG. 13A). The percentage of long cfDNA >533 bp measured by the VCP 533 bp assay was also significantly lower in the preeclamptic group (median, 6.6%; range, 3.2% to 10.4%) than in the control group (median, 8.7%; range, 5.4% to 16.8%) (Mann-Whitney U test, P=0.013) (FIG. 13B). With the VCP 1001 bp assay, the percentage of long cfDNA >1001 bp was lower in the preeclamptic groups (median, 4.1%; range, 2.2% to 6.2%) than in the control group (median, 4.6%; range, 3.5% to 12.8%), but the difference was not statistically significant (Mann-Whitney U test, P=0.138) (FIG. 13C).

The T-score was also calculated for each of the three assays, where the T-score is the absolute mean difference between the two groups divided by the pooled standard deviations between the two groups. The T-score therefore provides a parameter for evaluation of the discrimination power of the assays. As shown in FIGS. 13A-13C, the T-score is highest for the LINE1 assay (5.73) compared to the VCP 553 (2.83) and VCP 1001 assays (2.1738

An ROC curve analysis was used to determine which marker would be the most useful for differentiating the preeclamptic and control subjects (FIG. 14D). The AUCs for the LINE1 assay, VCP 533 bp assay, and VCP 1001 bp assay were 0.96, 0.79, and 0.69, respectively. There was a statistically significant difference between AUCs for LINE1 and VCP 1001 bp assays (P=0.012, Delong test), and for LINE1 and VCP 533 bp assays (P=0.039, Delong test), but not for VCP 1001 bp and VCP 533 bp assays (P=0.131, Delong test).

The results demonstrate the ability of the provided digital amplification assay-based approach to analyze the size distribution of cfDNA in plasma for differentiating pregnant women with and without preeclampsia. In this example, the LINE1 assay provides the best performance, which is consistent with the in-silico dPCR simulation results. These results also therefore demonstrate that the provided in-silico dPCR simulations are a useful predictive tool for guiding the design of the assay.

B. Methods

1. Separate Primers

Figure 14:
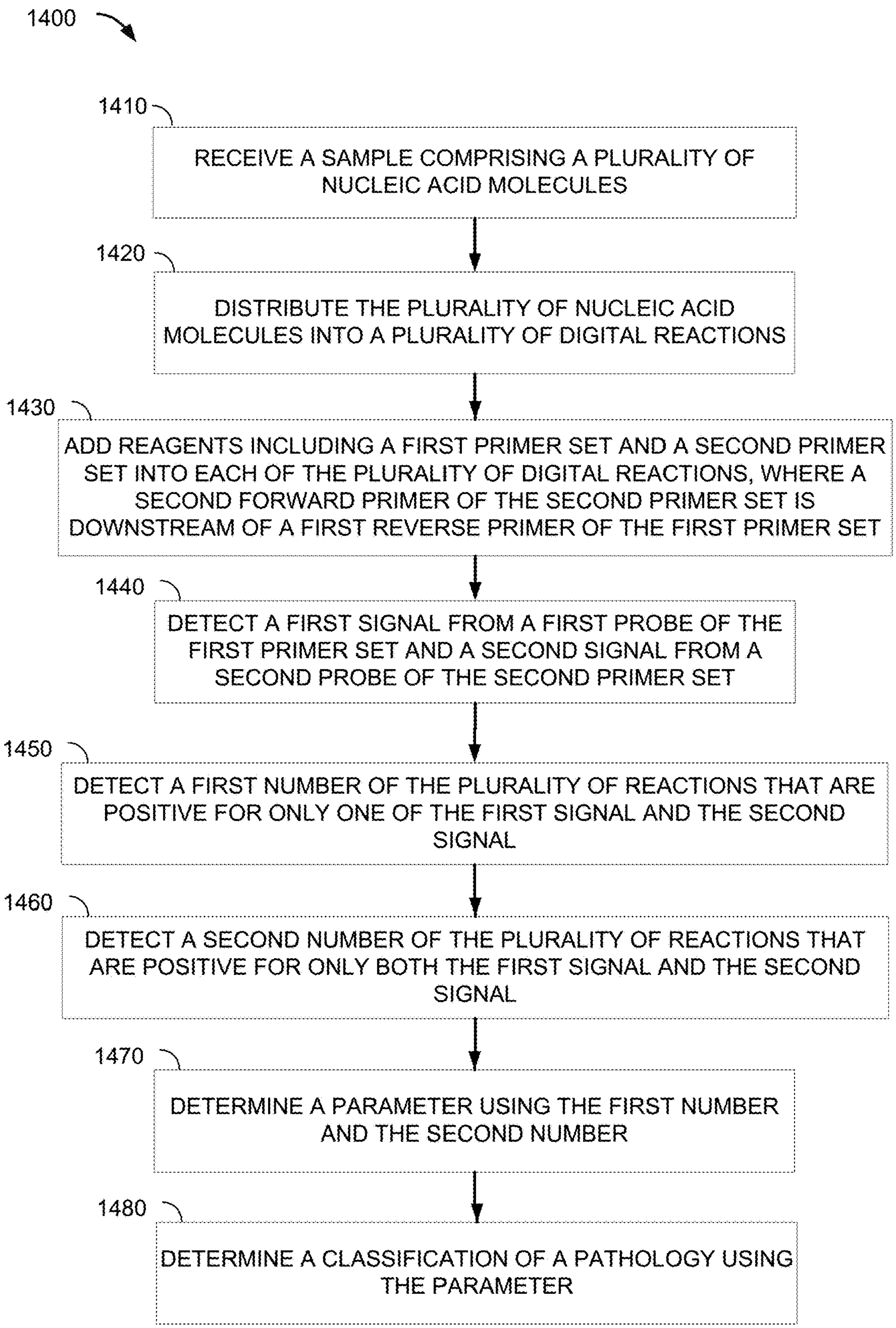
FIG. 14 presents a flowchart of a method for determining a pathology classification using digital amplification reactions with separate primers in accordance with a provided embodiment.

FIG. 14 presents a flowchart of a method 1400 for determining a classification of pathology in a subject by analyzing a biological sample from the subject to measure the size of nucleic acid molecules in the sample using separate primer sets according to embodiments of the present disclosure. Various examples of method 1400 are described above. Method 1400 can be performed partially or entirely using a computer system.

At block 1410, a sample comprising a plurality of nucleic acid molecules is received. Block 1410 can be performed in a similar manner to block 310. As with block 310, in some embodiments, the sample is a biological sample taken from a subject. In some embodiments, the plurality of nucleic acid molecules includes or consists of a plurality of DNA molecules. In some embodiments, the plurality of nucleic acid molecules includes or consists of a plurality of RNA molecules. In some embodiments, the plurality of nucleic acid molecules includes or consists of a plurality of cell-free nucleic acid molecules, e.g., a plurality of cell-free DNA molecules. As with block 310, in some embodiments, the plurality of nucleic acid molecules consists of between about 100 nucleic acid molecules and about 500,000 nucleic acid molecules, e.g., any of the numbers of nucleic acid molecules described in relation to block 310.

At block 1420, the plurality of nucleic acid molecules is distributed into a plurality of digital reactions. Block 1420 can be performed in a similar manner to block 320. As with block 320, in some embodiments, each of the plurality of digital reactions is a digital polymerase chain reaction. In some embodiments, each of the plurality of digital reactions is a droplet digital polymerase chain reaction. In some embodiments, the distribution of the plurality of nucleic acid molecules into the plurality of digital reactions results in the plurality of digital reactions having an average of one nucleic acid molecule per digital reaction.

At block 1430, reagents are added into each of the plurality of digital reactions. Block 1430 can be performed in a similar manner to block 330. As with block 330, the reagents for each of the plurality of reactions include a first primer set targeting a first region of a reference sequence, and a second primer set targeting a second region of the reference sequence. At least a portion of the plurality of nucleic acid molecules include at least a portion of the reference sequence, or at least a portion of a sequence complementary to the reference sequence. The second region is within a specified number of bases from the first region in the reference sequence. The specified number of bases can be any of those disclosed herein. For example, in some embodiments, the specified number of bases is about 5 kilobases or less. In some embodiments, the specified number of bases is about 500 bases or more. The first primer set includes a first forward primer, a first reverse primer, and a first probe. The second primer set includes a second forward primer, a second reverse primer, and a second probe. The second forward primer and the second reverse primer are each downstream from the first reverse primer in the reference sequence. The first region and the second region can each independently have any of the sizes disclosed herein. For example, in some embodiments, the first region and the second region each independently have a length that is less than about 500 bp.

The first probe and the second probe can be any of those disclosed herein. In some embodiments, the first probe and the second probe each independently comprise a fluorescent label. In some embodiments, the reagents for each of the plurality of digital reactions further include a reverse transcriptase enzyme.

In some embodiments, the reagents for each of the plurality of reactions further include a third primer set targeting a third region of the reference sequence. The third primer set includes a third forward primer, a third reverse primer, and a third probe. In some embodiments, the third region is located between the first region and the second region in the reference sequence, such that the third forward primer and the third reverse primer are each downstream from the first reverse primer in the reference sequence, and the third forward primer and the third reverse primer are each upstream from the second forward primer in the reference sequence.

At block 1440, a first signal from the first probe is detected for a first digital reaction of the plurality of digital reactions, and a second signal from the second probe is also detected for the first digital reaction. In some embodiments, method 1400 further includes an operation of detecting a third signal from the third probe, when present, in the first digital reaction. The signals can be any of those disclosed herein. Block 1440 can be performed in a similar manner to block 340. As with block 340, in some embodiments, the signals each independently comprise a fluorescence emission light having a different wavelength from that of the other signals.

At block 1450, a first number of the plurality of reactions that are positive for only one of the first signal and the second signal are detected. This first number therefore represents the count of digital reactions containing a nucleic acid molecule, e.g., a relatively short nucleic acid molecule, that includes only one of the first targeted region and the second targeted region.

At block 1460, a second number of the plurality of digital reactions that are positive for both of the first signal and the second signal are detected. This second number therefore represents the count of digital reactions containing a nucleic acid molecule, e.g., a relatively long nucleic acid molecule, that includes both the first targeted region and the second targeted region.

At block 1470, a parameter is determined using the first number and the second number. The parameter measures a relative amount between the first number and the second number. In some embodiments, the parameter is a separation value between the first number and the second number. As one example, determining the parameter can comprise dividing the first number by the second number or by a sum of the first number and the second number. As another example, determining the parameter can comprise dividing the second number by the first number or by a sum of the first number and the second number. As another example, determining the parameter can comprise subtracting the first number from the second number, and optionally dividing the subtraction result by the first number, by the second number, or by a sum of the first number and the second number. As another example, determining the parameter can comprise subtracting the second number from the first number, and optionally dividing the subtraction result by the first number, by the second number, or by a sum of the first number and the second number. In some embodiments, the parameter provides a statistical measure of a size profile (e.g., a histogram) of DNA fragments in the biological sample. The parameter may be referred to as a size parameter since it is determined from the sizes of the plurality of DNA fragments.

In some embodiments, method 1400 further includes detecting a third number of the plurality of digital reactions that are positive for the third signal from the third probe, when present in the digital reactions, and that also are positive for only one of the first signal and the second signal. This third number therefore represents the count of digital reactions containing a nucleic acid molecule that includes either the first region and the adjacent third region, or the second region and the adjacent third region.

In some embodiments, method 1400 further includes an operation of determining a second parameter using the first number and the third number, where the parameter measures a relative amount between the first number and the third number. In some embodiments, the second parameter is a separation value between the first number and the third number. As one example, determining the second parameter can comprise dividing the first number by the third number. As another example, determining the second parameter can comprise dividing the third number by the first number or by a sum of the first number and the second number. As another example, determining the second parameter can comprise subtracting the first number from the third number, and optionally dividing the subtraction result by the first number, by the third number, or by a sum of the first number and the third number. As another example, determining the second parameter comprises subtracting the third number from the first number, and optionally dividing the subtraction result by the first number, by the third number, or by a sum of the first number and the third number.

In some embodiments, method 1400 further includes an operation of determining a second parameter using the second number and the third number, where the second parameter measures a relative amount between the second number and the third number. In some embodiments, the second parameter is a separation value between the second number and the third number. As one example, determining the second parameter can comprise dividing the second number by the third number. As another example, determining the second parameter can comprise dividing the third number by the second number or by a sum of the first number and the second number. As another example, determining the second parameter can comprise subtracting the second number from the third number, and optionally dividing the subtraction result by the second number, by the third number, or by a sum of the second number and the third number. As another example, determining the second parameter can comprise subtracting the third number from the second number, and optionally dividing the subtraction result by the second number, by the third number, or by a sum of the second number and the third number.

At block 1480, a classification of a pathology is determined using the parameter. In some embodiments, the classification of the pathology is determined using the parameter and the second parameter. In some embodiments, the determination of the pathology classification involves comparing the one or more parameters to one or more reference values. Examples of a reference value include a normal value and a cutoff value that is a specified distance from a normal value (e.g., in units of standard deviation). The reference value may be determined from a different sample from the same organism (e.g., when the organism was known to be healthy). Thus, the reference value may correspond to a value of a parameter determined from a sample when the organism is presumed to have no pathology. In some embodiments, the biological sample is obtained from the organism after treatment and the reference value corresponds to a value of the first parameter determined from a sample taken before treatment. The reference value may also be determined from samples of other healthy organisms.

In some embodiments, the pathology is a cancer. In some embodiments, the pathology is preeclampsia toxemia.

In some embodiments, the classification may be numerical, textual, or any other indicator. The classification can provide a binary result of yes or no as to a pathology, a probability, or other score, which may be absolute or a relative value, e.g., relative to a previous classification of the organism at an earlier time. In some embodiments, the classification is that the organism does not have a pathology or that the level of the pathology has decreased. In other embodiments, the classification is that the organism does have a pathology or that a level of the pathology has increased.

In some embodiments, the classification of a pathology includes the level of the pathology, the existence of the pathology, a stage of the pathology, or a size of a tumor associated with the pathology. For example, whether the one or more parameters exceed (e.g., is greater than or less than, depending on how the first parameter is define) a reference threshold can be used to determine if a pathology exists, or at least a likelihood (e.g., a percentage likelihood). The extent above the threshold can provide an increasing likelihood, which can lead to the use of multiple thresholds. Additionally, the extent above can correspond to a different level of the pathology, e.g., more tumors or larger tumors. Thus, embodiments can diagnose, stage, prognosticate, or monitor progress of a level of a pathology in the subject organism.

2. Shared Primers

Figure 15:
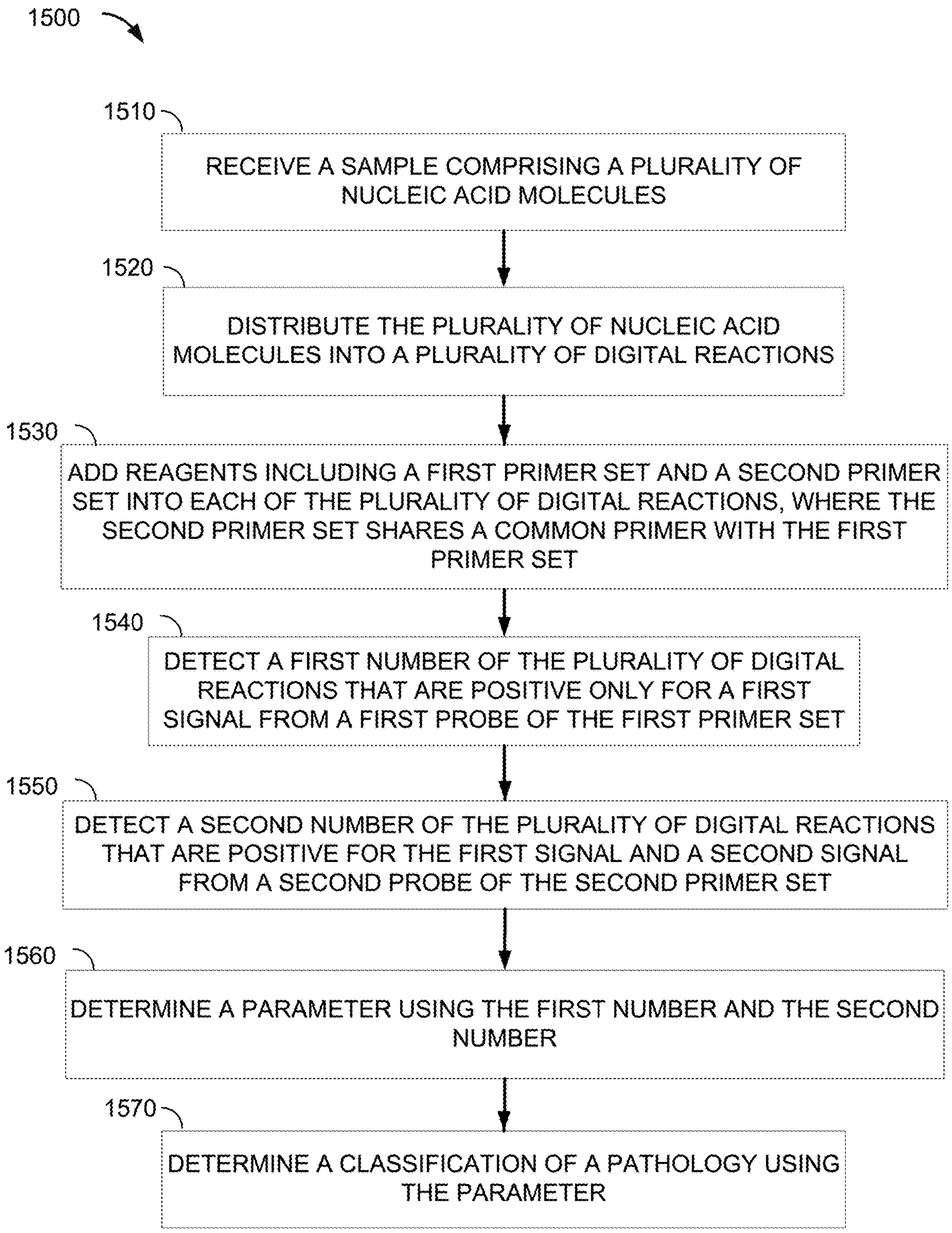
FIG. 15 presents a flowchart of a method for determining a pathology classification using digital amplification reactions with shared primers in accordance with a provided embodiment.

FIG. 15 presents a flowchart of a method 1500 for determining a classification of pathology in a subject by analyzing a biological sample from the subject to measure the size of nucleic acid molecules in the sample using shared primer sets according to embodiments of the present disclosure. Various examples of method 1500 are described above. Method 1500 can be performed partially or entirely using a computer system.

At block 1510, a sample comprising a plurality of nucleic acid molecules is received. Block 1510 can be performed in a similar manner to block 310. As with block 310, in some embodiments, the sample is a biological sample taken from a subject. In some embodiments, the plurality of nucleic acid molecules includes or consists of a plurality of DNA molecules. In some embodiments, the plurality of nucleic acid molecules includes or consists of a plurality of RNA molecules. In some embodiments, the plurality of nucleic acid molecules includes or consists of a plurality of cell-free nucleic acid molecules, e.g., a plurality of cell-free DNA molecules. As with block 310, in some embodiments, the plurality of nucleic acid molecules consists of between about 100 nucleic acid molecules and about 500,000 nucleic acid molecules, e.g., any of the numbers of nucleic acid molecules described in relation to block 310.

At block 1520, the plurality of nucleic acid molecules is distributed into a plurality of digital reactions. Block 1520 can be performed in a similar manner to block 320. As with block 320, in some embodiments, each of the plurality of digital reactions is a digital polymerase chain reaction. In some embodiments, each of the plurality of digital reactions is a droplet digital polymerase chain reaction. In some embodiments, the distribution of the plurality of nucleic acid molecules into the plurality of digital reactions results in the plurality of digital reactions having an average of one nucleic acid molecule per digital reaction.

At block 1530, reagents are added into each of the plurality of digital reactions. Block 1530 can be performed in a similar manner to block 530. As with block 530, the reagents for each of the plurality of reactions include a first primer set targeting a first region of a reference sequence, and a second primer set targeting a second region of the reference sequence. At least a portion of the plurality of nucleic acid molecules include at least a portion of the reference sequence, or at least a portion of a sequence complementary to the reference sequence. The second region is larger than the first region and includes the first region. The first primer set includes a first forward primer, a first reverse primer, and a first probe. The second primer set includes a second probe and a second primer that is either a second forward primer or a second reverse primer. The second primer set shares a common primer with the first primer set. For example, if the second primer set includes a second forward primer, then the second primer set shares the first reverse primer of the first primer set as a common primer with the first primer set. Alternatively, if the second primer set includes a second reverse primer, then the second primer set shares the first forward primer of the first primer set as a common primer with the first primer set. The shorter first region targeted by the first primer set can have any of the shorter first region sizes disclosed herein. For example, in some embodiments, the shorter first region has a length that is between about 40 bp and about 100 bp. The longer second region targeted by the second primer set can have any of the larger second region sizes disclosed herein. For example, in some embodiments, the longer second region has a length that is between about 100 bp and about 1000 bp. In some embodiments, the longer second region has a length that is between about 100 bp and about 250 bp.

The first probe and the second probe of block 1530 can be any of those disclosed herein and can be similar to the first probe and the second probe described in relation to block 330. As with block 330, in some embodiments, the first probe and the second probe each independently comprise a fluorescent label. As with block 330, in some embodiments, the reagents of block 1530 further include a reverse transcriptase enzyme.

In some embodiments, the reagents of block 1530 further include a third primer set targeting a third region of the reference sequence. The third region is larger than the first region and includes the first region. Additionally, the second region is larger than the third region and includes the third region. Accordingly, the first region is a subregion of the third region, which is itself a subregion of the second region.

The third primer set includes a third probe and a third primer that is either a third forward primer or a third reverse primer. The third primer shares the common primer with the first primer set and the second primer set. For example, if the second primer set includes a second forward primer, then the third primer set includes a third forward primer and the third primer set shares the first reverse primer of the first primer set as a common primer with the first primer set and the second primer set. Alternatively, if the second primer set includes a second reverse primer, then the third primer set includes a third reverse primer and shares the first forward primer of the first primer set as a common primer with the first primer set and the second primer set.

At block 1540, a first number of the plurality of reactions that are positive for only a first signal from the first probe is detected. The first signal can be any of those disclosed herein. Block 1540 can be performed in a similar manner to block 540. As with block 540, in some embodiments, the first signal comprises a fluorescence emission light, e.g., a fluorescence emission light having a different wavelength than that of fluorescence emission lights of the second signal and the third signal, when present. The first number represents the count of digital reactions containing a nucleic acid molecule, e.g., a relatively short nucleic acid molecule, that includes the entirety of the first targeted region but that does not include the entirety of the second targeted region.

At block 1550, a second number of the plurality of digital reactions that are positive for both the first signal and a second signal is detected. The second signal is from the second probe. The second signal can be any of those disclosed herein. Block 1550 can be performed in a similar manner to block 550. As with block 550, in some embodiments, the second signal comprises a fluorescence emission light, e.g., a fluorescence emission light having a different wavelength than that of fluorescence emission lights of the first signal and the third signal, when present. The second number represents the count of digital reactions containing a nucleic acid molecule, e.g., a relatively long nucleic acid molecule, that includes the entirety of the first targeted region and the entirety of the second targeted region.

In some embodiments, method 1500 further includes detecting a third number of the plurality of reactions that are not positive for the second signal and that are positive for both the first signal and a third signal. The third signal is from the third probe. The third signal can be any of those disclosed herein. In some embodiments, the third signal comprises a fluorescence emission light, e.g., a fluorescence emission light having a different wavelength than that of fluorescence emission lights of the first signal and the second signal. The third number represents the count of digital reactions containing a nucleic acid molecule that includes the entirety of the first targeted region and the entirety of the third targeted region but that does not include the entirety of the second targeted region.

At block 1560, a parameter is determined using the first number and the second number. Block 1560 can be performed in a similar manner to block 560. As with block 560, in some embodiments, the parameter measures a relative amount between the first number and the second number. In some embodiments, the parameter is a separation value between the first number and the second number. As one example, determining the parameter can comprise dividing the first number by the second number or by a sum of the first number and the second number. As another example, determining the parameter can comprise dividing the second number by the first number or by a sum of the first number and the second number. As another example, determining the parameter can comprise subtracting the first number from the second number, and optionally dividing the subtraction result by the first number, by the second number, or by a sum of the first number and the second number. As another example, determining the parameter can comprise subtracting the second number from the first number, and optionally dividing the subtraction result by the first number, by the second number, or by a sum of the first number and the second number.

In some embodiments, method 1500 further includes an operation of determining a second parameter using the first number and the third number, where the parameter measures a relative amount between the first number and the third number. In some embodiments, the second parameter is a separation value between the first number and the third number. As one example, determining the second parameter can comprise dividing the first number by the third number. As another example, determining the second parameter can comprise dividing the third number by the first number or by a sum of the first number and the second number. As another example, determining the second parameter can comprise subtracting the first number from the third number, and optionally dividing the subtraction result by the first number, by the third number, or by a sum of the first number and the third number. As another example, determining the second parameter can comprise subtracting the third number from the first number, and optionally dividing the subtraction result by the first number, by the third number, or by a sum of the first number and the third number.

In some embodiments, method 1500 further includes an operation of determining a second parameter using the second number and the third number, where the second parameter measures a relative amount between the second number and the third number. In some embodiments, the second parameter is a separation value between the second number and the third number. As one example, determining the second parameter can comprise dividing the second number by the third number. As another example, determining the second parameter can comprise dividing the third number by the second number or by a sum of the first number and the second number. As another example, determining the second parameter can comprise subtracting the second number from the third number, and optionally dividing the subtraction result by the second number, by the third number, or by a sum of the second number and the third number. In some embodiments, determining the second parameter comprises subtracting the third number from the second number, and optionally dividing the subtraction result by the second number, by the third number, or by a sum of the second number and the third number.

At block 1570, a classification of a pathology is determined using the parameter. In some embodiments, the classification of the pathology is determined using the parameter and the second parameter. In some embodiments, the determination of the pathology classification involves comparing the one or more parameters to one or more reference values. Examples of a reference value include a normal value and a cutoff value that is a specified distance from a normal value (e.g., in units of standard deviation). The reference value may be determined from a different sample from the same organism (e.g., when the organism was known to be healthy). Thus, the reference value may correspond to a value of a parameter determined from a sample when the organism is presumed to have no pathology. In some embodiments, the biological sample is obtained from the organism after treatment and the reference value corresponds to a value of the first parameter determined from a sample taken before treatment. The reference value may also be determined from samples of other healthy organisms.

In some embodiments, the pathology is a cancer. In some embodiments, the pathology is preeclampsia toxemia.

In some embodiments, the classification may be numerical, textual, or any other indicator. The classification can provide a binary result of yes or no as to a pathology, a probability, or other score, which may be absolute or a relative value, e.g., relative to a previous classification of the organism at an earlier time. In some embodiments, the classification is that the organism does not have a pathology or that the level of the pathology has decreased. In other embodiments, the classification is that the organism does have a pathology or that a level of the pathology has increased.

In some embodiments, the classification of a pathology includes the level of the pathology, the existence of the pathology, a stage of the pathology, or a size of a tumor associated with the pathology. For example, whether the one or more parameters exceed (e.g., is greater than or less than, depending on how the first parameter is define) a reference threshold can be used to determine if a pathology exists, or at least a likelihood (e.g., a percentage likelihood). The extent above the threshold can provide an increasing likelihood, which can lead to the use of multiple thresholds. Additionally, the extent above can correspond to a different level of the pathology, e.g., more tumors or larger tumors. Thus, embodiments can diagnose, stage, prognosticate, or monitor progress of a level of a pathology in the subject organism.

VIII. Systems

In another aspect, the present disclosure provides various systems, e.g., measurement systems and/or computer systems, for performing the methods described herein, or individual or combined operations of those methods.

Figure 16:
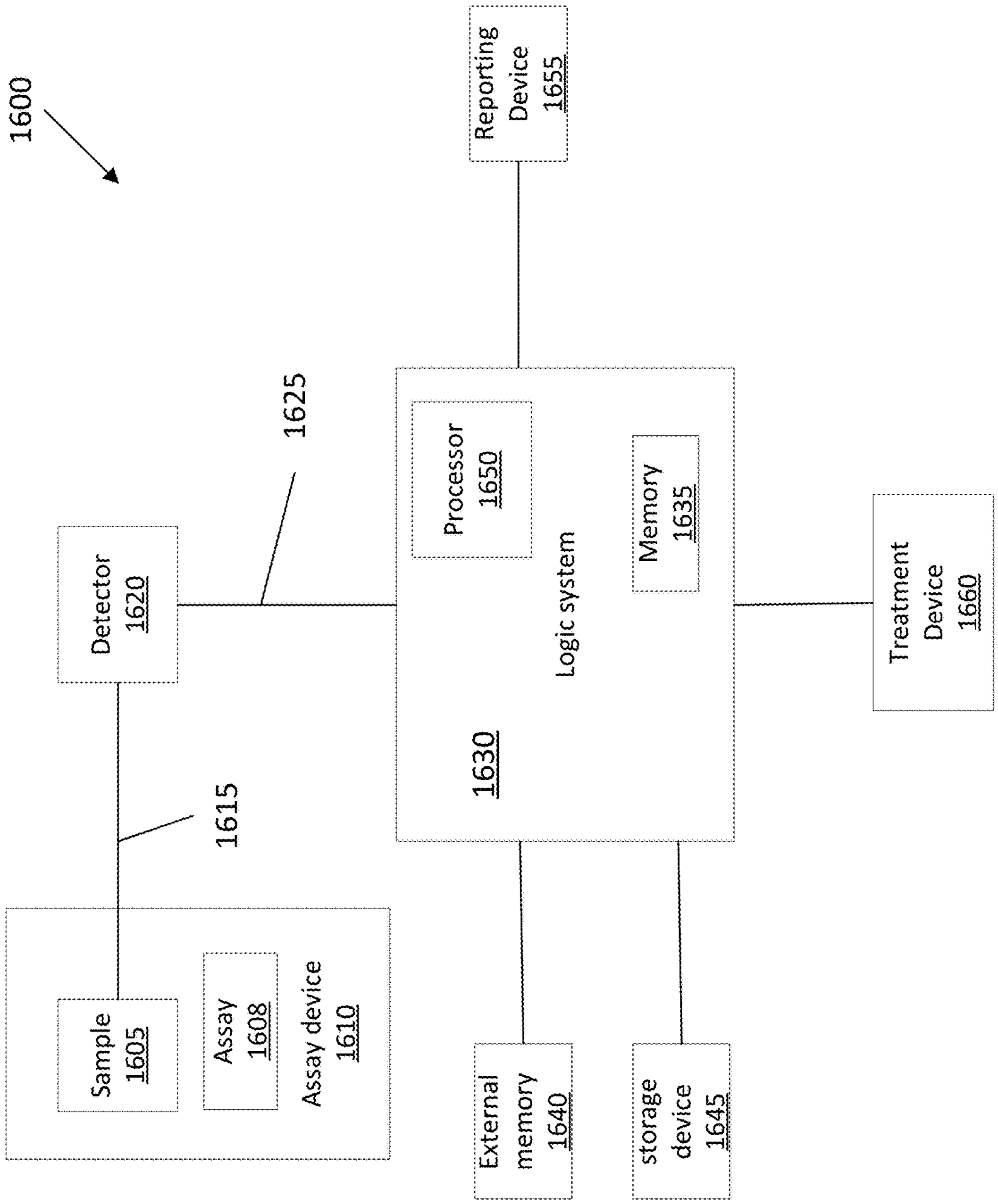
FIG. 16 presents a block diagram of an exemplary measurement system in accordance with a provided embodiment.

FIG. 16 illustrates a measurement system 1600 according to an embodiment of the present disclosure. The system as shown includes a sample 1605, such as cell-free DNA molecules within an assay device 1610, where an assay 1608 can be performed on sample 1605. For example, sample 1605 can be contacted with reagents of assay 1608 to provide a signal of a physical characteristic 1615 (e.g., multiplexed digital amplification information using a cell-free DNA molecule). An example of an assay device can be a flow cell that includes probes and/or primers of an assay or a tube through which a droplet moves (with the droplet including the assay). Physical characteristic 1615 (e.g., a fluorescence intensity, a voltage, or a current), from the sample is detected by detector 1620. Detector 1620 can take a measurement at intervals (e.g., periodic intervals) to obtain data points that make up a data signal. In one embodiment, an analog-to-digital converter converts an analog signal from the detector into digital form at a plurality of times. Assay device 1610 and detector 1620 can form an assay system, e.g., a digital PCR system that performs multiplexed digital amplification reactions according to embodiments described herein. A data signal 1625 is sent from detector 1620 to logic system 1630. As an example, data signal 1625 can be used to determine the production of targeted amplicons. Data signal 1625 can include various measurements made at a same time, e.g., different colors of fluorescent dyes or different electrical signals for a different molecule of sample 1605, and thus data signal 1625 can correspond to multiple signals. Data signal 1625 may be stored in a local memory 1635, an external memory 1640, or a storage device 1645.

Logic system 1630 may be, or may include, a computer system, ASIC, microprocessor, graphics processing unit (GPU), etc. It may also include or be coupled with a display (e.g., monitor, LED display, etc.) and a user input device (e.g., mouse, keyboard, buttons, etc.). Logic system 1630 and the other components may be part of a stand-alone or network connected computer system, or they may be directly attached to or incorporated in a device (e.g., a digital PCR device) that includes detector 1620 and/or assay device 1610. Logic system 1630 may also include software that executes in a processor 1650. Logic system 1630 may include a computer readable medium storing instructions for controlling measurement system 1600 to perform any of the methods described herein. For example, logic system 1630 can provide commands to a system that includes assay device 1610 such that partitioning, amplification or other physical operations are performed. Such physical operations can be performed in a particular order, e.g., with reagents being added and removed in a particular order. Such physical operations may be performed by a robotics system, e.g., including a robotic arm, as may be used to obtain a sample and perform an assay.

Measurement system 1600 may also include a reporting device 1655, which can present results of any of the methods describe herein, e.g., as determined using the measurement system. Reporting device 1655 can be in communication with a reporting module within logic system 1630 that can aggregate, format, and send a report to reporting device 1655. Reporting device 1655 can present information indicating, for example, the presence of a relatively long DNA molecule in sample 1605, where the size of the relatively long DNA molecule is measured or estimated without requiring sequencing of the DNA molecule. The reporting module can present information from any one or more of the detecting and/or determining steps in methods 300, 600, 1100, 1400, and/or 1500, as described in Sections II.C, III.B, V.E, VII.B(1), and VII.B(2), respectively. The information can be presented by reporting device 1655 in any format that can be recognized and interpreted by a user of the measurement system 1600. For example, the information can be presented by reporting device 1655 in a displayed, printed, or transmitted format, or any combination thereof.

Measurement system 1600 may also include a treatment device 1660, which can provide a treatment to the subject. Treatment device 1660 can determine a treatment and/or be used to perform a treatment. Examples of such treatment can include surgery, radiation therapy, chemotherapy, immunotherapy, targeted therapy, hormone therapy, and stem cell transplant. Logic system 1630 may be connected to treatment device 1660, e.g., to provide results of a method described herein. The treatment device may receive inputs from other devices, such as an imaging device and user inputs (e.g., to control the treatment, such as controls over a robotic system).

Figure 17:
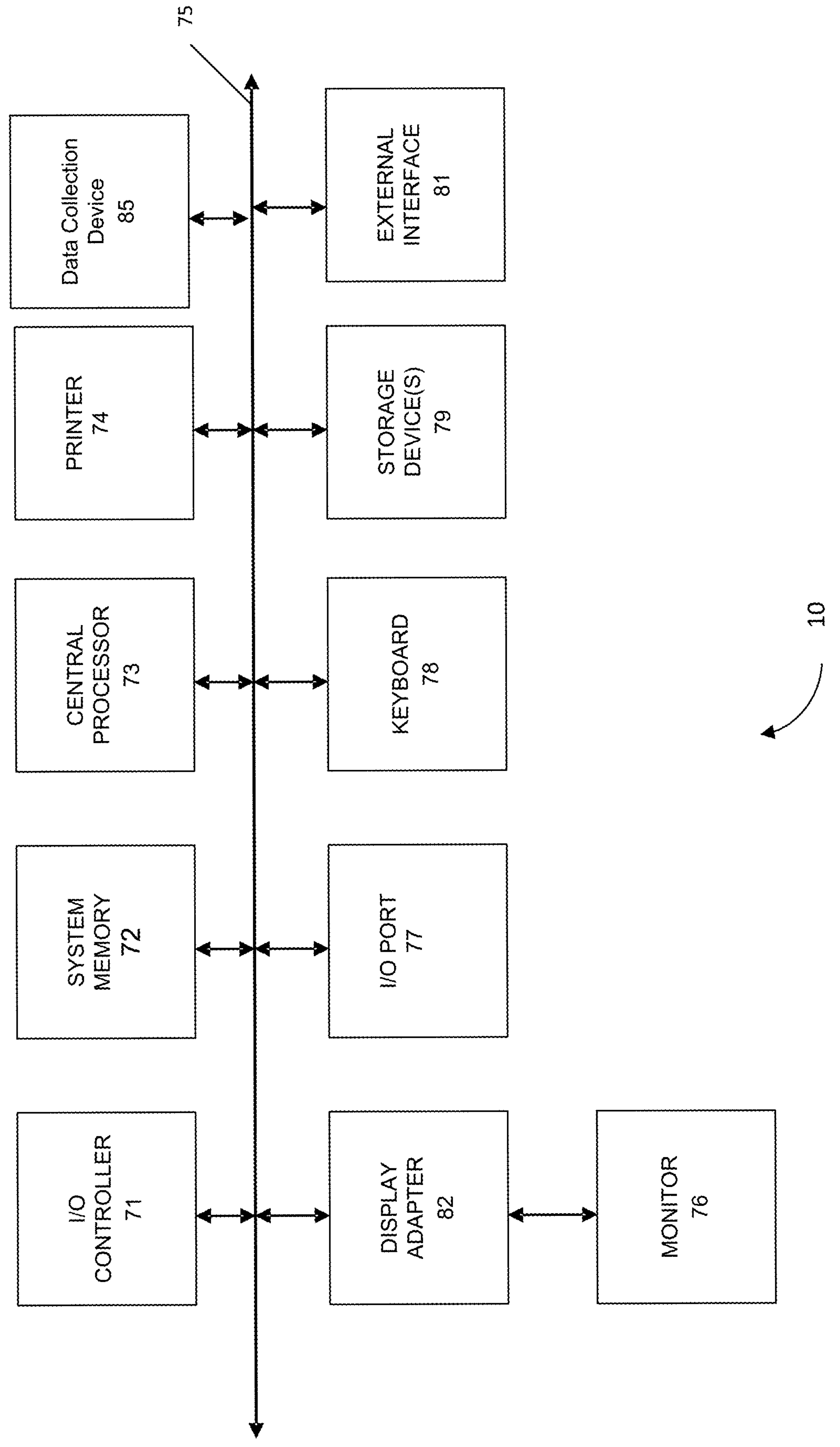
FIG. 17 presents a block diagram of an exemplary computer system in accordance with a provided embodiment.

Any of the computer systems mentioned herein may utilize any suitable number of subsystems. Examples of such subsystems are shown in FIG. 17 in computer system 10. In some embodiments, a computer system includes a single computer apparatus, where the subsystems can be the components of the computer apparatus. In other embodiments, a computer system can include multiple computer apparatuses, each being a subsystem, with internal components. A computer system can include desktop and laptop computers, tablets, mobile phones and other mobile devices.

The subsystems shown in FIG. 17 are interconnected via a system bus 75. Additional subsystems such as a printer 74, keyboard 78, storage device(s) 79, monitor 76 (e.g., a display screen, such as an LED), which is coupled to display adapter 82, and others are shown. Peripherals and input/output (I/O) devices, which couple to I/O controller 71, can be connected to the computer system by any number of means known in the art such as input/output (I/O) port 77 (e.g., USB, FIREWIRE®). For example, I/O port 77 or external interface 81 (e.g., Ethernet, Wi-Fi, etc.) can be used to connect computer system 10 to a wide area network such as the Internet, a mouse input device, or a scanner. The interconnection via system bus 75 allows the central processor 73 to communicate with each subsystem and to control the execution of a plurality of instructions from system memory 72 or the storage device(s) 79 (e.g., a fixed disk, such as a hard drive, or optical disk), as well as the exchange of information between subsystems. The system memory 72 and/or the storage device(s) 79 may embody a computer readable medium. Another subsystem is a data collection device 85, such as a camera, microphone, accelerometer, and the like. Any of the data mentioned herein can be output from one component to another component and can be output to the user.

A computer system can include a plurality of the same components or subsystems, e.g., connected together by external interface 81, by an internal interface, or via removable storage devices that can be connected and removed from one component to another component. In some embodiments, computer systems, subsystem, or apparatuses can communicate over a network. In such instances, one computer can be considered a client and another computer a server, where each can be part of a same computer system. A client and a server can each include multiple systems, subsystems, or components. In various embodiments, methods may involve various numbers of clients and/or servers, including at least 10, 20, 50, 100, 200, 500, 1,000, or 10,000 devices. Methods can include various numbers of communications between devices, including at least 100, 200, 500, 1,000, 10,000, 50,000, 100,000, 500,00, or one million communications. Such communications can involve at least 1 MB, 10 MB, 100 MB, 1 GB, 10 GB, or 100 GB of data.

Aspects of embodiments can be implemented in the form of control logic using hardware circuitry (e.g., an application specific integrated circuit or field programmable gate array) and/or using computer software stored in a memory with a generally programmable processor in a modular or integrated manner, and thus a processor can include memory storing software instructions that configure hardware circuitry, as well as an FPGA with configuration instructions or an ASIC. As used herein, a processor can include a single-core processor, multi-core processor on a same integrated chip, or multiple processing units on a single circuit board or networked, as well as dedicated hardware. Based on the disclosure and teachings provided herein, a person of ordinary skill in the art will know and appreciate other ways and/or methods to implement embodiments of the present disclosure using hardware and a combination of hardware and software.

Any of the software components or functions described in this application may be implemented as software code to be executed by a processor using any suitable computer language such as, for example, Java, C, C++, C#, Objective-C, Swift, or scripting language such as Perl or Python using, for example, conventional or object-oriented techniques. The software code may be stored as a series of instructions or commands on a computer readable medium for storage and/or transmission. A suitable non-transitory computer readable medium can include random access memory (RAM), a read only memory (ROM), a magnetic medium such as a hard-drive or a floppy disk, or an optical medium such as a compact disk (CD) or DVD (digital versatile disk) or Blu-ray disk, flash memory, and the like. The computer readable medium may be any combination of such devices. In addition, the order of operations may be re-arranged. A process can be terminated when its operations are completed, but could have additional steps not included in a figure. A process may correspond to a method, a function, a procedure, a subroutine, a subprogram, etc. When a process corresponds to a function, its termination may correspond to a return of the function to the calling function or the main function.

Such programs may also be encoded and transmitted using carrier signals adapted for transmission via wired, optical, and/or wireless networks conforming to a variety of protocols, including the Internet. As such, a computer readable medium may be created using a data signal encoded with such programs. Computer readable media encoded with the program code may be packaged with a compatible device or provided separately from other devices (e.g., via Internet download). Any such computer readable medium may reside on or within a single computer product (e.g., a hard drive, a CD, or an entire computer system), and may be present on or within different computer products within a system or network. A computer system may include a monitor, printer, or other suitable display for providing any of the results mentioned herein to a user.

Any of the methods described herein may be totally or partially performed with a computer system including one or more processors, which can be configured to perform the steps. Any operations performed with a processor may be performed in real-time. The term "real-time" may refer to computing operations or processes that are completed within a certain time constraint. As examples, a time constraint may be 30 seconds, 1 minute, 10 minutes, 30 minutes, 1 hour, 4 hours, 1 day, or 7 days. Thus, embodiments can be directed to computer systems configured to perform the steps of any of the methods described herein, potentially with different components performing a respective step or a respective group of steps. Although presented as numbered steps, steps of methods herein can be performed at a same time or at different times or in a different order. Additionally, portions of these steps may be used with portions of other steps from other methods. Also, all or portions of a step may be optional. Additionally, any of the steps of any of the methods can be performed with modules, units, circuits, or other means of a system for performing these steps.

The specific details of particular embodiments may be combined in any suitable manner without departing from the spirit and scope of embodiments of the disclosure. However, other embodiments of the disclosure may be directed to specific embodiments relating to each individual aspect, or specific combinations of these individual aspects.

The above description of example embodiments of the present disclosure has been presented for the purposes of illustration and description. It is not intended to be exhaustive or to limit the disclosure to the precise form described, and many modifications and variations are possible in light of the teaching above.

A recitation of "a," "an," or "the" is intended to mean "one or more" unless specifically indicated to the contrary. The use of "or" is intended to mean an "inclusive or," and not an "exclusive or" unless specifically indicated to the contrary. Reference to a "first" component does not necessarily require that a second component be provided. Moreover, reference to a "first" or a "second" component does not limit the referenced component to a particular location or order unless expressly stated. The term "based on" is intended to mean "based at least in part on."

The claims may be drafted to exclude any element which may be optional. As such, this statement is intended to serve as antecedent basis for use of such exclusive terminology as "solely", "only", and the like in connection with the recitation of claim elements, or the use of a "negative" limitation.

All patents, patent applications, publications, and descriptions mentioned herein are incorporated by reference in their entirety for all purposes. None is admitted as being prior art. Where a conflict exists between the instant application and a reference provided herein, the instant application shall dominate.

What is claimed is:

1. A method for analyzing a biological sample from a subject, the method comprising:

receiving the biological sample comprising a plurality of cell-free nucleic acid molecules;

distributing the plurality of cell-free nucleic acid molecules into a plurality of digital reactions;

adding reagents into each of the plurality of digital reactions, wherein:

the reagents for each of the plurality of digital reactions include a first primer set targeting a first region of a reference sequence, and a second primer set targeting a second region that is a specified number of bases from the first region in the reference sequence, the specified number of bases being 5 kilobases or less;

the first primer set includes a first forward primer, a first reverse primer, and a first probe that generates a first signal associated with amplification of the first region using the first forward and reverse primers; and the second primer set includes a second forward primer, a second reverse primer, and a second probe that generates a second signal associated with amplification of the second region using the second forward and reverse primers, wherein the second forward primer is downstream from the first reverse primer in the reference sequence;

for a first digital reaction of the plurality of digital reactions, detecting the first signal from the first probe and the second signal from the second probe; and based on detecting both the first signal and the second signal generated by the first probe and the second probe in the first digital reaction, determining that the first digital reaction includes a cell-free nucleic acid molecule of the plurality of the cell-free nucleic acid molecules (1) that covers the first region and the second region and (2) that has a length that is at least as long as the combined lengths of the first region, the second region, and the specified number of bases separating the first region and the second region.

2. The method of claim 1, wherein the specified number of bases is 500 bases or more.

3. The method of claim 1, further comprising:

detecting a first number of the plurality of digital reactions that are positive for only one of the first signal and the second signal, wherein, based on being positive for only one of the first signal and the second signal, each digital reaction of the first number of the plurality of digital reactions independently includes a cell-free nucleic acid molecule of the plurality of the cell-free nucleic acid molecules that covers the first region or the second region, and that has a length that is at least as long as the first region or the second region;

detecting a second number of the plurality of digital reactions that are positive for both of the first signal and the second signal, wherein, based on being positive for both the first signal and the second signal, each digital reaction of the second number of the plurality of digital reactions independently includes a cell-free nucleic acid molecule of the plurality of the cell-free nucleic acid molecules that covers the first region and the second region, and that has a length that is at least as long as the combined lengths of the first region, the second region, and the specified number of bases separating the first region and the second region; and determining a first parameter using the first number and the second number, the first parameter measuring a relative amount between the first number and the second number.

4. The method of claim 3, further comprising:

determining a size distribution of the plurality of cell-free nucleic acid molecules using the first parameter.

5. The method of claim 3, further comprising:

determining a classification of a pathology for the subject by comparing the first parameter to a threshold and assigning the subject to the classification of the pathology based on the comparison.

6. The method of claim 3, wherein the reagents for each of the plurality of digital reactions further include a third primer set targeting a third region of the reference sequence, the third primer set including a third forward primer, a third reverse primer, and a third probe that generates a third signal associated with amplification of the third region using the third forward and reverse primers, wherein the third forward primer is downstream from the first reverse primer in the reference sequence, wherein the second forward primer is downstream from the third reverse primer in the reference sequence, and wherein the method further comprises:

for each digital reaction of the plurality of digital reactions, detecting the first signal, the second signal, and the third signal.

7. The method of claim 6, wherein the method further comprises:

detecting a third number of the plurality of digital reactions that are positive for the third signal and only one of the first signal and the second signal; and determining a second parameter using the first number and the third number, the second parameter measuring a relative amount between the first number and the third number.

8. The method of claim 6, wherein the method further comprises:

detecting a third number of the plurality of digital reactions that are positive for the third signal and only one of the first signal and the second signal; and determining a second parameter using the second number and the third number, the second parameter measuring a relative amount between the second number and the third number.

9. The method of claim 7, further comprising:

determining a size distribution of the plurality of cell-free nucleic acid molecules using the first parameter and the second parameter.

10. The method of claim 7, further comprising:

determining a classification of a pathology for the subject using the first parameter and the second parameter.

11. The method of claim 1, wherein the first region and the second region each independently have a length that is less than 500 bp.

12. The method of claim 1, wherein the plurality of cell-free nucleic acid molecules consists of between 100 cell-free nucleic acid molecules and 500,000 cell-free nucleic acid molecules.

13. The method of claim 1, wherein the reagents for each of the plurality of digital reactions further include a third primer set targeting a third region and a fourth primer set targeting a fourth region that is larger than the third region and includes the third region, the third primer set including a third forward primer, a third reverse primer, and a third probe, the fourth primer set including a fourth probe and a fourth primer that is a fourth forward primer or a fourth reverse primer, wherein the fourth primer set shares a common primer with the third primer set, and wherein the fourth probe recognizes a portion of the fourth region that is not within the third region; and wherein the method further comprises:

detecting a first number of the plurality of digital reactions that are positive for only a third signal from the third probe;

detecting a second number of the plurality of digital reactions that are positive for both the third signal and a fourth signal, wherein the fourth signal is from the fourth probe;

determining a parameter using the first number and the second number, the parameter measuring a relative amount between the first number and the second number; and determining a classification of a preeclampsia for the subject using the parameter.

14. The method of claim 13, wherein the third and fourth regions are each a part of a same repeat region that occurs at least 10 times in a reference human genome.

15. The method of claim 13, wherein the third region has a length between 40 bp and 100 bp.

16. The method of claim 13, wherein the fourth region has a length between 100 bp and 1000 bp.

17. The method of claim 13, wherein the reagents for each of the plurality of digital reactions further include a fifth primer set targeting a fifth region that is larger than the third region and includes the third region, the fifth primer set including a fifth forward primer, a fifth reverse primer, and a fifth probe, wherein the fifth primer set shares the common primer with the third primer set, wherein the fourth region includes the fifth region, and wherein the method further comprises:

detecting a third number of the plurality of digital reactions that are not positive for the fourth signal and that are positive for both the third signal and a fifth signal, wherein the fifth signal is from the fifth probe.

18. The method of claim 17, further comprising:

determining a second parameter using the first number and the third number, the second parameter measuring a relative amount between the first number and the third number, wherein the determining of the classification of the preeclampsia further uses the second parameter.

19. The method of claim 17, further comprising:

determining a third parameter using the second number and the third number, the third parameter measuring a relative amount between the second number and the third number, wherein the determining of the classification of the preeclampsia further uses the third parameter.

* * * * *

SEQUENCE LISTING

```
Sequence total quantity: 13
SEQ ID NO: 1            moltype = DNA  length = 22
FEATURE                 Location/Qualifiers
source                  1..22
                        mol_type = other DNA
                        organism = synthetic construct
SEQUENCE: 1
ctctgagcta cgggaggaca tt                                             22

SEQ ID NO: 2            moltype = DNA  length = 30
FEATURE                 Location/Qualifiers
source                  1..30
                        mol_type = other DNA
                        organism = synthetic construct
SEQUENCE: 2
ttcttctaaa tttttttcaa agttttcaac                                     30

SEQ ID NO: 3            moltype = DNA  length = 16
FEATURE                 Location/Qualifiers
source                  1..16
                        mol_type = other DNA
                        organism = synthetic construct
SEQUENCE: 3
ctttgccttt ggtttg                                                    16

SEQ ID NO: 4            moltype = DNA  length = 15
FEATURE                 Location/Qualifiers
source                  1..15
                        mol_type = other DNA
                        organism = synthetic construct
SEQUENCE: 4
agccttggtt ttcag                                                     15

SEQ ID NO: 5            moltype = DNA  length = 29
FEATURE                 Location/Qualifiers
source                  1..29
                        mol_type = other DNA
                        organism = synthetic construct
SEQUENCE: 5
cctgattcta gattatcttg atatcctca                                      29

SEQ ID NO: 6            moltype = DNA  length = 21
FEATURE                 Location/Qualifiers
source                  1..21
                        mol_type = other DNA
                        organism = synthetic construct
SEQUENCE: 6
attccactgg ggttagggtt g                                              21

SEQ ID NO: 7            moltype = DNA  length = 20
FEATURE                 Location/Qualifiers
source                  1..20
                        mol_type = other DNA
                        organism = synthetic construct
SEQUENCE: 7
attctacctt ccctttagac                                                20

SEQ ID NO: 8            moltype = DNA  length = 21
FEATURE                 Location/Qualifiers
source                  1..21
                        mol_type = other DNA
                        organism = synthetic construct
SEQUENCE: 8
gggaggtctg tggaccctat c                                              21

SEQ ID NO: 9            moltype = DNA  length = 29
FEATURE                 Location/Qualifiers
```

-continued

```
source                  1..29
                        mol_type = other DNA
                        organism = synthetic construct
SEQUENCE: 9
tgagctgaga tgagactcat atacttatc                                         29

SEQ ID NO: 10           moltype = DNA  length = 16
FEATURE                 Location/Qualifiers
source                  1..16
                        mol_type = other DNA
                        organism = synthetic construct
SEQUENCE: 10
cttccccaac catcag                                                       16

SEQ ID NO: 11           moltype = DNA  length = 23
FEATURE                 Location/Qualifiers
source                  1..23
                        mol_type = other DNA
                        organism = synthetic construct
SEQUENCE: 11
tcttctcggc cttattccaa att                                               23

SEQ ID NO: 12           moltype = DNA  length = 29
FEATURE                 Location/Qualifiers
source                  1..29
                        mol_type = other DNA
                        organism = synthetic construct
SEQUENCE: 12
gaattttaat agggcatcaa agataaaga                                         29

SEQ ID NO: 13           moltype = DNA  length = 17
FEATURE                 Location/Qualifiers
source                  1..17
                        mol_type = other DNA
                        organism = synthetic construct
SEQUENCE: 13
aatggattca cctcagc                                                      17
```